(12) United States Patent
Kensch et al.

(10) Patent No.: US 7,846,705 B2
(45) Date of Patent: Dec. 7, 2010

(54) MANNANASES

(75) Inventors: Oliver Kensch, Cologne (DE); Wayne M. Coco, Cologne (DE); Andreas Scheidig, Cologne (DE); Ute Beister, Cologne (DE); Birgitta Leuthner, Cologne (DE); Nadine Koch, Cologne (DE); Markus Rarbach, Cologne (DE); Ulrich Kettling, Cologne (DE); Ulrich Haupts, Cologne (DE)

(73) Assignee: Direvo Industrial Biotechnology GmbH, Cologne (DE)

( * ) Notice: Subject to any disclaimer, the term of this patent is extended or adjusted under 35 U.S.C. 154(b) by 655 days.

(21) Appl. No.: 11/778,690

(22) Filed: Jul. 17, 2007

(65) Prior Publication Data

US 2008/0064064 A1    Mar. 13, 2008

Related U.S. Application Data

(60) Provisional application No. 60/831,629, filed on Jul. 18, 2006.

(51) Int. Cl.
    *C12N 9/24* (2006.01)
(52) U.S. Cl. ..................................... 435/200
(58) Field of Classification Search ........................ None
    See application file for complete search history.

(56) References Cited

FOREIGN PATENT DOCUMENTS

| WO | 91/18974 | 12/1991 |
|---|---|---|
| WO | 94/25576 | 11/1994 |
| WO | 03/012110 | 2/2003 |

OTHER PUBLICATIONS

Sabini, Elisabetta et al: "The three-dimensional structure of a *Trichoderma reesei* β-mannanase from glycoside hydrolase family 5"; Acta Crystallographica Section D., Biological Crystallography; Jan. 2000; vol. 56, No. 1; pp. 3-13; XP002408250; ISSN: 0907-4449.

Politz, O. et al: "A highly thermostable endo-(1,4)-β-mannanase from the marine bacterium *Rhodothermus marinus*"; Applied Microbiology and Biotechnology; Jun. 2000; vol. 53, No. 6; pp. 715-721; XP002408251; ISSN: 0175-7598.

Arisan-Atac, Inci et al: "Purification, and characterization of a β-mannanase of *Trichoderma reesei* C-30"; Applied Microbiology and Biotechnology; 1993; vol. 39, No. 1; pp. 58-62; XP009075158; ISSN: 0175-7598.

(Continued)

*Primary Examiner*—Nashaat T Nashed
(74) *Attorney, Agent, or Firm*—Rankin, Hill & Clark LLP

(57) ABSTRACT

The present invention provides an insertion, deletion and/or substitution mutein of wild-type *Trichoderma reesei* β-mannanase having enhanced thermostability, proteolytic stability, specific activity and/or stability at low pH, a nucleic acid molecule encoding said mannanase mutein, a composition comprising said mannanase mutein; a method for its preparation, and its use for food and feed processing, for coffee extraction and the processing of coffee waste, as a supplement to food and feed, for enzyme aided bleaching of paper pulps, as bleaching and/or desizing agent in textile industry, for oil and gas well stimulation by hydraulic fracturing, as detergent, for removal of biofilms and in delivery systems, or for the processing of renewable resources intended for the production of biological fuels.

19 Claims, 9 Drawing Sheets

A

B

OTHER PUBLICATIONS

Hägglund et al.; "A cellulose-binding module of the *Trichoderma reesei* β-mannanase Man5A increases the mannan-hydrolysis of complex substrates"; Journal of Biotechnology; 2003; 37.

Biely, P. et al.; "Enzymology of hemicellulose degradation"; 1998; pp. 25-47; Harman and Kubiceck (ed) *Trichoderma* and *Gliocladium*, vol. 2, Taylor and Francis Ltd. London.

Stalbrand, Henrik et al.; "Cloning and Expression in *Saccharomyces cerevisiae* of a *Trichoderma reesei* β- Mannanase Gene Containing a Cellulose Binding Domain"; Appl. Environ. Microbiol.; 1995; vol. 61; pp. 1090-1097.

Berezovsky, Igor N. et al.; Physics and evolution of thermophilic adaptation. Proc. Natl. Acad. Sci. USA; 2005; vol. 102; pp. 12742-12747.

Braithwaite, Kerynne L. et al.; (1995) A non-modular endo-β-1,4-mannanase from *Pseudomonas fluorescens* subspecies *cellulosa*. Biochem. J.; 1995; vol. 305; pp. 1005-1010.

Tamaru, Yutaka et al.; Purification and Characterisation of an Extracellular β-1,4-Mannanase from a Marine Bacterium *Vibrio* sp. Strain MA-138; Appl. Environ. Microbiol.; 1995; vol. 61; pp. 4454-4458.

Duffaud Guy D. et al.; Purification and Characterization of Extremely Thermostable β-Mannanase, βMannosidase, and α-Galactosidase from the Hyperthermophilic Eubacterium *Thermotoga neapolitana* 5068; Appl. Environ. Microbiol.; 1997; vol. 64; pp. 4428-4432.

Gibbs, Moreland D. et al.; Sequencing, cloning and expression of a α-1,4-mannanase gene, manA, from the extremely thermophilic anaerobic bacterium, *Caldicellulosiruptor* Rt8B.4; FEMS Microbiol. Lett.; 1996; vol. 141; pp. 37-43.

Bicho, Paul A. et al.; "The characterization of a thermostable endo-β-mannanase cloned from *Caldocellum saccharolyticum*"; Appl. Microbiol. Biotechnol. 1991; vol. 36; pp. 337-343.

Parker, Kimberley N. et al.; "Galactomannanases Man2 and Man5 from *Thermotoga* Species: Growth, Physiology on Galactomannans, Gene Sequence Analysis, and Biochemical Properties of Recombinant Enzymes"; Biotechnol. Bioeng.; 2001; vol. 75; pp. 322-333.

Hägglund, Per; "Mannan-hydrolysis by hemicellulases: Enzyme-polysaccaride interaction of modular β-mannanase"; 2002; Thesis, Lund University, Sweden.

Lee, J.T. et al.; "Effects of Guar Meal By-Product with and Without β-Mannanase Hemicell on Broiler Performance"; Poult.Sci.; 2005; vol. 84; 2005; pp. 1261-1267.

Jackson, M.E. et al.; "Effects of β-mannanase in Corn-Soybean Meal Diets on Laying Hen Performance"; Poult. Sci.; 1999; vol. 78; pp. 1737-1741.

Kim, S.W. et al.; "Use of carbohydrases in corn-soybean meal-based nursery diets"; J. Anim. Sci.; 2003; vol. 81; pp. 2496-2504.

Pettey, L.A. et al.; "Effects of β-mannanase addition to corn-soybean meal diets on growth performance, carcass traits, and nutrient digestibility of weanling and growing-finishing pigs"; J.Anim.Sci.; 2002; vol. 80; pp. 1012-1019.

Suurnäkki, A. et al.; "Hemicellulases in the Bleaching of Chemical Pulps"; Ad v. Biochem. Eng. Biotechnol. 1997; vol. 57; pp. 261-287.

McCutchen, Carol M. et al.; "Characterization of Extremely Thermostable Enzymatic Breakers (α-1,6-Galactosidase and β-1,4-Mannanase) from the Hyperthermophilic Bacterium *Thermotoga-Neapolitana*-5068 for Hydrolysis of Guar Gum"; Biotechnology and Bioengineering; 1996; vol. 52; pp. 332-339.

Livingston, Craig D. et al.; "Protein sequence alignments: a strategy for the hierarchical analysis of residue conservation"; Comput.Appl Biosci.; 1993; vol. 9; pp. 745-756.

Taylor, William Ramsay (1986) "The Classification of Amino Acid Conservation"; J. Theor.Biol.; 1986; vol. 119; pp. 205-218.

"In Vitro Protein Expression Guide" available from Promega Inc (Part# BR053), (2005).

Sunna, Anwar et al.; "A Gene Encoding a Novel Multidomain β-1, 4-Mannanase from *Caldibacillus cellulovorans* and Action of the Recombinant Enzyme on Kraft Pulp"; Applied and Environmental Microbiology; American Society for Microbiology; Feb. 2000; vol. 66, No. 2; pp. 664-670.

Office action issued in corresponding European Patent Application No. 07 787 629.0, dated May 14, 2009.

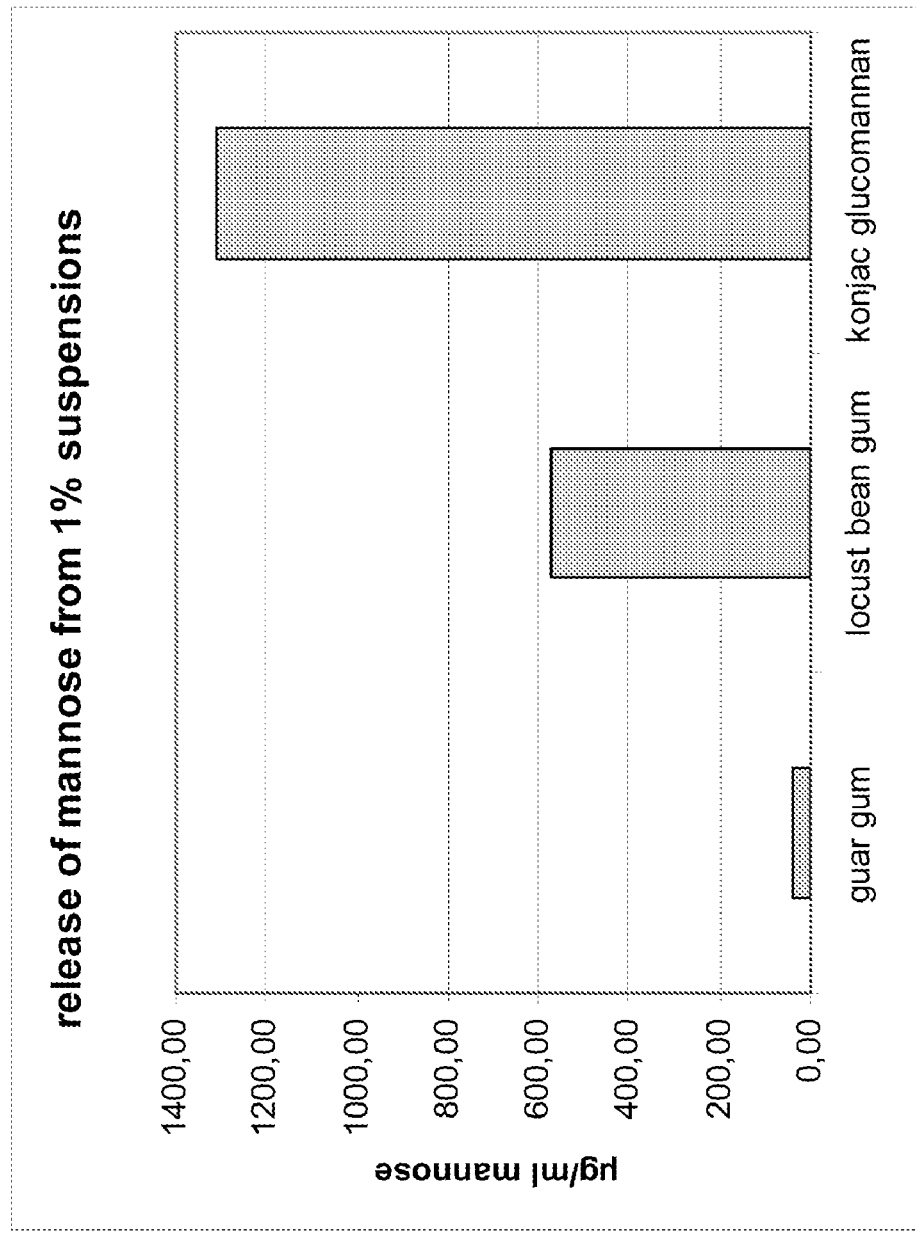

SEQUENCE LISTING

```
<160> NUMBER OF SEQ ID NOS: 13

<210> SEQ ID NO 1
<211> LENGTH: 352
<212> TYPE: PRT
<213> ORGANISM: Trichoderma reesei

<400> SEQUENCE: 1

Ala Ser Ser Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Phe Leu
            20                  25                  30

Thr Asn His Ala Asp Val Asp Ser Thr Phe Ser His Ile Ser Ser Ser
```

-continued

```
            35                  40                  45
Gly Leu Lys Val Val Arg Val Trp Gly Phe Asn Asp Val Asn Thr Gln
 50                  55                  60
Pro Ser Pro Gly Gln Ile Trp Phe Gln Lys Leu Ser Ala Thr Gly Ser
 65                  70                  75                  80
Thr Ile Asn Thr Gly Ala Asp Gly Leu Gln Thr Leu Asp Tyr Val Val
                 85                  90                  95
Gln Ser Ala Glu Gln His Asn Leu Lys Leu Ile Ile Pro Phe Val Asn
                100                 105                 110
Asn Trp Ser Asp Tyr Gly Gly Ile Asn Ala Tyr Val Asn Ala Phe Gly
            115                 120                 125
Gly Asn Ala Thr Thr Trp Tyr Thr Asn Thr Ala Ala Gln Thr Gln Tyr
        130                 135                 140
Arg Lys Tyr Val Gln Ala Val Val Ser Arg Tyr Ala Asn Ser Thr Ala
145                 150                 155                 160
Ile Phe Ala Trp Glu Leu Gly Asn Glu Pro Arg Cys Asn Gly Cys Ser
                165                 170                 175
Thr Asp Val Ile Val Gln Trp Ala Thr Ser Val Ser Gln Tyr Val Lys
            180                 185                 190
Ser Leu Asp Ser Asn His Leu Val Thr Leu Gly Asp Glu Gly Leu Gly
        195                 200                 205
Leu Ser Thr Gly Asp Gly Ala Tyr Pro Tyr Thr Tyr Gly Glu Gly Thr
    210                 215                 220
Asp Phe Ala Lys Asn Val Gln Ile Lys Ser Leu Asp Phe Gly Thr Phe
225                 230                 235                 240
His Leu Tyr Pro Asp Ser Trp Gly Thr Asn Tyr Thr Trp Gly Asn Gly
                245                 250                 255
Trp Ile Gln Thr His Ala Ala Ala Cys Leu Ala Ala Gly Lys Pro Cys
            260                 265                 270
Val Phe Glu Glu Tyr Gly Ala Gln Gln Asn Pro Cys Thr Asn Glu Ala
        275                 280                 285
Pro Trp Gln Thr Thr Ser Leu Thr Thr Arg Gly Met Gly Gly Asp Met
    290                 295                 300
Phe Trp Gln Trp Gly Asp Thr Phe Ala Asn Gly Ala Gln Ser Asn Ser
305                 310                 315                 320
Asp Pro Tyr Thr Val Trp Tyr Asn Ser Ser Asn Trp Gln Cys Leu Val
                325                 330                 335
Lys Asn His Val Asp Ala Ile Asn Gly Gly Thr Thr Thr Pro Pro Pro
            340                 345                 350
```

<210> SEQ ID NO 2
<211> LENGTH: 1029
<212> TYPE: DNA
<213> ORGANISM: Trichoderma reesei

<400> SEQUENCE: 2

```
gcttcgagct tgtaaccat  atccggcacc caattcaaca tcgatggcaa agtaggctac      60
tttgcgggca ccaactgcta ctggtgctcg ttcctgacca ccacgccga  cgttgattcc     120 acctttagcc acatctcttc ctctggcctc aaggtagtcc gtgtatgggg cttcaacgac     180
gtcaacacgc agccctctcc cggccagatc tggttccaga agctgtccgc tacgggtct      240 acgatcaaca cgggagctga tgggctgcag actctcgact acgtagtcca gtcagccgag     300
cagcacaacc tcaagctcat catcccgttc gtcaacaact ggagcgacta cggcgggata     360
```

```
aacgcctatg tcaacgcctt tggcggcaat gcgaccacct ggtacactaa cacggccgcg      420
caaactcagt accgcaagta cgtccaggcc gtcgtcagcc gctacgcaaa ctcgacggcc      480
atctttgcgt gggagctggg caacgagcct cgctgcaacg ggtgcagtac tgatgtgatt      540
gttcagtggg cgacgagtgt gtcccaatat gtcaagtcac ttgattcgaa ccatctcgtg      600
acgcttggag acgaggggct cggtctcagt actggagacg cgcttatcc gtatacttat       660 ggcgagggca ctgattttgc caagaatgta caaatcaagt cgcttgactt tggtactttc      720
cacctctatc cggactcttg gggaacaaac tacacttggg gcaatggctg gattcagact      780
catgccgccg cttgtttagc agcaggcaaa ccttgcgtgt ttgaagaata cggcgcacag      840
caaaacccct gcaccaacga ggcaccctgg caaacaacct ctctcacgac tcgcggcatg      900
ggtggcgaca tgtttggca gtggggagac acttttgcca acggtgccca gtcgaacagt       960
gacccgtaca ccgtctggta caactcatcg aactggcaat gcttggtcaa gaaccacgtt     1020
gatgctatt                                                             1029

<210> SEQ ID NO 3
<211> LENGTH: 27
<212> TYPE: DNA
<213> ORGANISM: artificial
<220> FEATURE:
<223> OTHER INFORMATION: primer mannA forward fishing

<400> SEQUENCE: 3
ccggaattca tgctctcaaa gagtctc                                          27

<210> SEQ ID NO 4
<211> LENGTH: 27
<212> TYPE: DNA
<213> ORGANISM: artificial
<220> FEATURE:
<223> OTHER INFORMATION: primer mannA reverse fishing

<400> SEQUENCE: 4
cccaagcttt catgtattca ggcattg                                          27

<210> SEQ ID NO 5
<211> LENGTH: 267
<212> TYPE: DNA
<213> ORGANISM: Trichoderma reesei

<400> SEQUENCE: 5
atgagatttc cttcaatttt tactgctgtt ttattcgcag catcctccgc attagctgct       60
ccagtcaaca ctacaacaga agatgaaacg gcacaaattc cggctgaagc tgtcatcggt      120
tactcagatt tagaagggga tttcgatgtt gctgttttgc cattttccaa cagcacaaat      180
aacgggttat tgtttataaa tactactatt gccagcattg ctgctaaaga agaaggggta      240
tctttggaga aaagagaggc tgaagct                                          267

<210> SEQ ID NO 6
<211> LENGTH: 267
<212> TYPE: DNA
<213> ORGANISM: artificial
<220> FEATURE:
<223> OTHER INFORMATION: improved leader DNA

<400> SEQUENCE: 6
atgagatttc cttcaatttt tactgctgtt ttattcgcag catcctctgc attagctgct       60
ccagtcaaca ctataacaga agatgaaacg gcacaaattc ctgctgaagc tgtcatcggt      120
```

-continued

```
tactcagatt tagaagggga tttcgatgtt gctgttttgc catttttccaa cagcacaaat      180 aacgggttat tgtttatgaa tactactact gccagcattg ctgctaaaga agaagtggta      240
tctttggaga aaagagaggc tgaagct                                           267
```

<210> SEQ ID NO 7
<211> LENGTH: 89
<212> TYPE: PRT
<213> ORGANISM: artificial
<220> FEATURE:
<223> OTHER INFORMATION: improved leader protein

<400> SEQUENCE: 7

```
Met Arg Phe Pro Ser Ile Phe Thr Ala Val Leu Phe Ala Ala Ser Ser
1               5                   10                  15

Ala Leu Ala Ala Pro Val Asn Thr Ile Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Met Asn Thr Thr Thr Ala Ser Ile Ala Ala Lys Glu Glu Val Val
65                  70                  75                  80

Ser Leu Glu Lys Arg Glu Ala Glu Ala
                85
```

<210> SEQ ID NO 8
<211> LENGTH: 54
<212> TYPE: DNA
<213> ORGANISM: artificial
<220> FEATURE:
<223> OTHER INFORMATION: forward primer for cloning intron-free PIN with
      leader into pYES2

<400> SEQUENCE: 8

```
gaaggttctt tggataaaag agaagcttgc ggtactgcag cctgttccac gtgc            54
```

<210> SEQ ID NO 9
<211> LENGTH: 39
<212> TYPE: DNA
<213> ORGANISM: artificial
<220> FEATURE:
<223> OTHER INFORMATION: reverse primer for cloning intron-free PIN with
      leader into pYES2

<400> SEQUENCE: 9

```
ccctctagtc tcgagtcatg tattcaggca ttgcgagta                              39
```

<210> SEQ ID NO 10
<211> LENGTH: 358
<212> TYPE: PRT
<213> ORGANISM: artificial
<220> FEATURE:
<223> OTHER INFORMATION: variant B mannanase

<400> SEQUENCE: 10

```
Ala Ser Arg Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Phe Leu
                20                  25                  30

Thr Asn His Ala Asp Val Asp Ser Thr Phe Ser His Ile Ser Ser Ser
            35                  40                  45
```

```
Gly Leu Lys Val Val Arg Val Trp Gly Phe Asn Asp Val Asn Thr Gln
     50                  55                  60

Pro Ser Pro Gly Gln Ile Trp Phe Gln Lys Leu Ser Ala Thr Gly Ser
 65                  70                  75                  80

Thr Ile Asn Thr Gly Ala Asp Gly Leu Gln Thr Leu Asp Tyr Val Val
                 85                  90                  95

Gln Ser Ala Glu Gln His Asn Leu Lys Leu Ile Ile Pro Phe Val Asn
            100                 105                 110

Asn Trp Ser Asp Tyr Gly Gly Ile Asn Ala Tyr Val Asn Ala Phe Gly
        115                 120                 125

Gly Asn Ala Thr Thr Trp Tyr Thr Asn Thr Ala Ala Gln Thr Gln Tyr
    130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys Asn Gly Cys Ser
                165                 170                 175

Thr Asp Val Ile Val Gln Trp Ala Thr Ser Val Ser Gln Tyr Val Lys
            180                 185                 190

Ser Leu Asp Ser Asn His Leu Val Thr Leu Gly Asp Glu Gly Phe Gly
        195                 200                 205

Leu Ser Thr Gly Asp Gly Ala Tyr Pro Tyr Thr Tyr Gly Glu Gly Thr
    210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
                245                 250                 255

Trp Ile Gln Thr His Ala Ala Ala Cys Leu Ala Ala Gly Lys Pro Cys
            260                 265                 270

Val Leu Glu Glu Tyr Gly Ala Gln Gln Asn Pro Cys Thr Asn Glu Ala
        275                 280                 285

Pro Trp Gln Thr Thr Ser Leu Thr Thr Arg Gly Met Gly Gly Asp Met
    290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Trp Gln Cys Leu Val
                325                 330                 335

Lys Asn His Val Asp Ala Ile Asn Gly Gly Thr Thr Thr Pro Pro Pro
                340                 345                 350

His His His His His His
            355

<210> SEQ ID NO 11
<211> LENGTH: 358
<212> TYPE: PRT
<213> ORGANISM: artificial
<220> FEATURE:
<223> OTHER INFORMATION: variant C mannanase

<400> SEQUENCE: 11

Ala Ser Arg Phe Val Thr Ile Ser Gly Thr Gln Phe Asn Ile Asp Gly
 1               5                  10                  15

Lys Val Gly Tyr Phe Ala Gly Thr Asn Cys Tyr Trp Cys Ser Phe Leu
                20                  25                  30

Thr Asn His Ala Asp Val Asp Ser Thr Phe Ser His Ile Ser Ser Ser
            35                  40                  45
```

```
Gly Leu Lys Val Val Arg Val Trp Gly Phe Asn Asp Val Asn Thr Gln
 50                  55                  60

Pro Ser Pro Gly Gln Ile Trp Phe Gln Lys Leu Ser Ala Thr Gly Ser
 65                  70                  75                  80

Thr Ile Asn Thr Gly Ala Asp Gly Leu Gln Thr Leu Asp Tyr Val Val
                 85                  90                  95

Gln Ser Ala Glu Gln His Asn Leu Lys Leu Ile Ile Pro Phe Val Asn
            100                 105                 110

Asn Trp Ser Asp Tyr Gly Gly Ile Asn Ala Tyr Val Asn Ala Phe Gly
        115                 120                 125

Gly Asn Ala Thr Thr Trp Tyr Thr Asn Thr Ala Ala Gln Thr Gln Tyr
    130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys Asn Gly Cys Ser
                165                 170                 175

Thr Asp Val Ile Val Gln Trp Ala Thr Ser Val Ser Gln Tyr Val Lys
            180                 185                 190

Ser Leu Asp Ser Asn His Leu Val Ser Leu Gly Asp Glu Gly Leu Gly
        195                 200                 205

Leu Ser Thr Gly Asp Gly Ala Tyr Pro Tyr Thr Tyr Gly Glu Gly Thr
    210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
                245                 250                 255

Trp Ile Gln Thr His Ala Ala Ala Cys Leu Ala Ala Gly Lys Pro Cys
            260                 265                 270

Val Leu Glu Glu Tyr Gly Ala Arg Gln Asn Pro Cys Thr Asn Glu Ala
        275                 280                 285

Pro Trp Gln Thr Thr Ser Leu Thr Thr Arg Gly Met Gly Gly Asp Met
    290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Trp Gln Cys Leu Val
                325                 330                 335

Lys Asn His Val Asp Ala Ile Asn Gly Gly Thr Thr Thr Pro Pro Pro
            340                 345                 350

His His His His His His
        355

<210> SEQ ID NO 12
<211> LENGTH: 358
<212> TYPE: PRT
<213> ORGANISM: artificial
<220> FEATURE:
<223> OTHER INFORMATION: variant 31 mannanase

<400> SEQUENCE: 12

Ala Ser Ser Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Phe Leu
            20                  25                  30

Thr Asn His Ala Asp Val Asp Ser Thr Phe Ser His Ile Ser Ser Ser
        35                  40                  45
```

```
Gly Leu Lys Val Val Arg Val Trp Gly Phe Asn Asp Val Asn Thr Gln
 50                  55                  60
Pro Ser Pro Gly Gln Ile Trp Phe Gln Lys Leu Ser Ala Thr Gly Ser
 65                  70                  75                  80
Thr Ile Asn Thr Gly Ala Asp Gly Leu Gln Thr Leu Asp Tyr Val Val
                 85                  90                  95
Gln Ser Ala Glu Gln His Asn Leu Lys Leu Ile Ile Pro Phe Val Asn
                100                 105                 110
Asn Trp Ser Asp Tyr Gly Gly Ile Asn Ala Tyr Val Asn Ala Phe Gly
                115                 120                 125
Gly Asn Ala Thr Thr Trp Tyr Thr Asn Thr Ala Ala Gln Thr Gln Tyr
        130                 135                 140
Arg Lys Tyr Val Gln Ala Val Val Ser Arg Tyr Ala Asn Ser Thr Ala
145                 150                 155                 160
Ile Phe Ala Trp Glu Leu Gly Asn Glu Pro Arg Cys Asn Gly Cys Ser
                165                 170                 175
Thr Asp Val Ile Val Gln Trp Ala Thr Ser Val Ser Gln Tyr Val Lys
                180                 185                 190
Ser Leu Asp Ser Asn His Leu Val Ser Leu Gly Asp Glu Gly Phe Gly
                195                 200                 205
Leu Ser Thr Gly Asp Gly Ala Tyr Pro Tyr Thr Tyr Gly Glu Gly Thr
        210                 215                 220
Asp Phe Ala Lys Asn Val Gln Ile Lys Ser Leu Asp Phe Gly Thr Phe
225                 230                 235                 240
His Leu Tyr Pro Asp Ser Trp Gly Thr Asn Tyr Thr Trp Gly Asn Gly
                245                 250                 255
Trp Ile Gln Thr His Ala Ala Ala Cys Leu Ala Ala Gly Lys Pro Cys
                260                 265                 270
Val Leu Glu Glu Tyr Gly Ala Gln Gln Asn Pro Cys Thr Asn Glu Ala
                275                 280                 285
Pro Trp Gln Thr Thr Ser Leu Thr Thr Arg Gly Met Gly Gly Asp Met
                290                 295                 300
Phe Trp Gln Trp Gly Asp Thr Phe Ala Asn Gly Ala Gln Ser Asn Ser
305                 310                 315                 320
Asp Pro Tyr Thr Val Trp Tyr Asn Ser Ser Asn Trp Gln Cys Leu Val
                325                 330                 335
Lys Asn His Val Asp Ala Ile Asn Gly Gly Thr Thr Thr Pro Pro Pro
                340                 345                 350
His His His His His His
        355

<210> SEQ ID NO 13
<211> LENGTH: 358
<212> TYPE: PRT
<213> ORGANISM: artificial
<220> FEATURE:
<223> OTHER INFORMATION: variant 16 mannanase

<400> SEQUENCE: 13

Ala Ser Ser Phe Val Thr Ile Ser Gly Thr Gln Phe Asn Ile Asp Gly
 1               5                  10                  15
Lys Val Gly Tyr Phe Ala Gly Thr Asn Cys Tyr Trp Cys Ser Phe Leu
                20                  25                  30
```

-continued

```
Thr Asn His Ala Asp Val Asp Ser Thr Phe Ser His Ile Ser Ser Ser
     35                  40                  45

Gly Leu Lys Val Val Arg Val Trp Gly Phe Asn Asp Val Asn Thr Gln
     50                  55                  60

Pro Ser Pro Gly Gln Ile Trp Phe Gln Lys Leu Ser Ala Thr Gly Ser
 65                  70                  75                  80

Thr Ile Asn Thr Gly Ala Asp Gly Leu Gln Thr Leu Asp Tyr Val Val
                 85                  90                  95

Gln Ser Ala Glu Gln His Asn Leu Lys Leu Ile Ile Pro Phe Val Asn
                100                 105                 110

Asn Trp Ser Asp Tyr Gly Gly Ile Asn Ala Tyr Val Asn Ala Phe Gly
             115                 120                 125

Gly Asn Ala Thr Thr Trp Tyr Thr Asn Thr Ala Ala Gln Thr Gln Tyr
             130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys Asn Gly Cys Ser
             165                 170                 175

Thr Asp Val Ile Val Gln Trp Ala Thr Ser Val Ser Gln Tyr Val Lys
             180                 185                 190

Ser Leu Asp Ser Asn His Leu Val Ser Leu Gly Asp Glu Gly Leu Gly
             195                 200                 205

Leu Ser Thr Gly Asp Gly Ala Tyr Pro Tyr Tyr Gly Glu Gly Thr
210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
             245                 250                 255

Trp Ile Gln Thr His Ala Ala Ala Cys Leu Ala Ala Gly Lys Pro Cys
             260                 265                 270

Val Phe Glu Glu Tyr Gly Ala Gln Gln Asn Pro Cys Thr Asn Glu Ala
             275                 280                 285

Pro Trp Gln Thr Thr Ser Leu Thr Thr Arg Gly Met Gly Gly Asp Met
             290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Asn Trp Gln Cys Leu Val
                 325                 330                 335

Lys Asn His Val Asp Ala Ile Asn Gly Gly Thr Thr Thr Pro Pro Pro
             340                 345                 350

His His His His His
         355
```

MANNANASES

The present application includes a sequence listing, which is hereby incorporated by reference. The sequence listing was submitted using EFS-web as a text file entitled MIH17438SEQ.txt. The file was created on Jul. 5, 2007 at 9:24 a.m. and contains 20 KB of data. The file contents comply with the American Standard Code for Information Interchange (ASCII) and can be viewed using an IBM-PC compatible computer using the MS-Windows operating system.

FIELD OF INVENTION

The present invention provides an insertion, deletion and/or substitution mutein of wild-type *Trichoderma reesei* β-mannanase having enhanced thermostability, proteolytic stability, specific activity and/or stability at low pH, a nucleic acid molecule encoding said mannanase mutein, a composition comprising said mannanase mutein; a method for its preparation, and its use for food and feed processing, for coffee extraction and the processing of coffee waste, as a supplement to food and feed, for enzyme aided bleaching of paper pulps, as bleaching and/or desizing agent in textile industry, for oil and gas well stimulation by hydraulic fracturing, as detergent, for removal of biofilms and in delivery systems, or for the processing of renewable resources intended for the production of biological fuels.

BACKGROUND OF THE INVENTION

Hemicellulose and hemicellulases: Hemicelluloses have a complex chemical structure and are often referred to as mannans, xylans and galactans on the basis of the predominant sugar type in the main chain. A range of mannan-type polysaccharides is synthesised by a wide variety of plants and is found in different types of plant tissue.

The main role of hemicelluloses and galactomannans is to function as structural polysaccharide and/or as reserve energy. Besides amylose and amylopectin which are the most widespread storage polysaccharides in plants, there is a diverse group of mannan-based polysaccharides found in seeds, roots, bulbs and tubers of various plants. These include mannans, galactomannans and glucomannans. Mannans are comprised of linear chains of β-1-4-mannan and are found in the plant seed endosperm of certain plant species. Mannan has been isolated from ivory nut, date or green coffee bean. In most cases the mannans are highly insoluble in water and very dense. Accordingly, it has been suggested that the mannan forms the molecular basis for the hardness which is characteristic for palm kernels, such as ivory nut. Galactomannans are reserve polysaccharides in the seed endosperm of leguminous plants. In contrast to unsubstituted mannans, the galactomannans are water soluble and can store water in the seed. Polysaccharides can be organised in structures ranging from irregular amorphous to highly organised crystalline structures. Crystalline linear β-(1-4)-D-mannan has for example been found in the cell walls of ivory nuts in two morphologies, mannan-I and mannan-II, respectively. The former is of granular morphology, while the latter is fibrillar.

Due to the complex structural composition of the plant cell wall, microorganisms thriving on decaying plant material must possess a number of different enzymes that are able to hydrolyse these highly polymeric and mostly insoluble materials. These enzyme systems often comprise a combination of endo- and exo-acting enzymes. The two major endo-acting enzymes involved in degradation of hemicelluloses are β-mannanase and β-xylanase. In addition, the exo-acting enzymes β-mannosidase, α-galactosidase and β-glucosidase are needed for complete degradation of galactoglucomannan. Often these enzyme have a modular structure in which a catalytic domain is connected through a linker region to a carbohydrate-binding domain (CBD) (Warren (1996) *Microbial hydrolysis of polysaccharides*. Annu. Rev. Microbiol., 50:183-212). However, other domains such as thermostabilising modules have been found in some xylanases.

Mannanases: Endo-β-1,4-D-mannanase (β-mannanase; EC 3.2.1.78) catalyses the random hydrolysis of manno-glycosidic bonds in mannan-based polysaccharides. Most β-mannanases degrade oligosaccharides down to DP4 (Biely and Tenkanen (1998) *Enzymology of hemicellulose degradation*, pages 25-47. In Harman and Kubiceck (ed) *Trichoderma and Gliocladium*, vol. 2, Taylor and Francis Ltd. London), however, residual activity has been demonstrated on mannotriose, indicating at least four subsites for mannose binding on the protein. The main end products of hydrolysis are often mannobiose and mannotriose, although significant amounts of mannose are also produced. Some β-mannanases are able to degrade crystalline mannan. In addition to hydrolysis, several β-mannanases including β-mannanase from *Trichoderma reesei*, have been shown to form transglycosylation products with either mannose or mannobiose as glycosidic bond acceptor.

β-mannanases have been isolated from a wide range of organisms including bacteria, fungi, plants and animals. Although mostly extracellular, some β-mannanases appear to be cell-associated. Their expression is often induced by growth on mannan or galactomannan, however, β-mannanase from *T. reesei* can also be induced by cellulose, while its expression is suppressed by glucose and other monosaccharides. Frequently multiple mannanases with different isoelectric points are found in the same organism, representing products from different genes or different products from the same gene, respectively.

*Trichoderma reesei* produces a potent enzyme system for the degradation of hemicellulase (Biely and Tenkanen (1998) *Enzymology of hemicellulose degradation*, pages 25-47. In Harman and Kubiceck (ed) *Trichoderma and Gliocladium*, vol. 2, Taylor and Francis Ltd. London), including the β-mannanase Man5A, which is transcribed from the gene man1 (Stalbrand et al. (1995) Cloning and expression in *Saccharomyces cerevisiae* of a *Trichoderma reesei* β-mannanase gene containing a cellulose binding domain. *Appl. Environ. Microbiol.* 61:1090-1097). Isoforms with varying isoelectric points are thought to represent different posttranslational modifications such as glycosylation. The mannanase consists of a N-terminal catalytic domain and a C-terminal cellulose-binding domain which are connected via a highly O-glycosylated Thr/Pro-rich linker. The structure of the catalytic domain has been solved and reveals a globular domain, belonging to the (βα)$_8$-barrel structural class (Sabini et al. (2000) The three-dimensional structure of *Trichoderma reesei* β-mannanase from glycoside hydrolase family 5. *Acta Crystallogr. Sect. D: Biol. Crystallogr.* 56:3-13). A shallow substrate binding groove could be identified, and two additional β-sheets which are not conserved in other (βα)$_8$-barrel type proteins.

In general, β-mannanases have moderate temperature optima between 40° C. and 70° C., except some β-mannanases from thermophiles (Politz et al. (2000) A highly thermostable endo-1,4-β-mannanase from the marine bacterium *Rhodothermus marinus*; *Appl. Microbiol. Biotechnol.* 53:715-721). The pH-optimum is in the neutral or acidic region, e.g. pH 5.0 for β-mannanase from *T. reesei* (Arisan-Atac et al. (1993) Purification and characterisation of a β-mannanase of *Trichoderma reesei* C-30; *Appl. Microbiol. Biotechnol.* 39:58-62). The molecular weights of the enzymes range between 30 kD and 80 kD.

Enzyme stability: Stability (incl. thermostability, pH stability and stability against proteolytic digestion) and activity under application conditions is a critical parameter for many industrially applied enzymes, since these enzymes often tend to be insufficiently stable or active under application conditions. For example, high thermostability allows a lower dosage of the enzyme due to longer activity under high temperature process conditions and therefore provides a commercial advantage. Many mesophilic and thermophilic organisms express enzyme variants which are adapted to the respective temperature conditions in which the organisms thrive. While mesophilic species tend to have less thermostable enzymes, thermophilic organisms must possess highly stable enzymes. A comparison of homologous enzymes from meso- and thermophilic organisms reveals two basic mechanisms for the increased stability. One is "structure-based" where the hyperthermophilic enzymes are significantly more compact than their mesophilic counterparts. Stability is enhanced by the sheer number of interactions. In contrast, a so-called "sequence-based" mechanism utilises a small number of apparently strong interactions which are responsible for the high thermal stability (Berezovsky and Shakhnovich (2005) Physics and evolution of thermophilic adaptation. *Proc. Natl. Acad. Sci. USA* 102:12742-12747). β-Mannanases from mesophilic (Braithwaite et Al. (1995) A non-modular endo-β-1,4-mannanase from *Pseudomonas fluorescens* subspecies *cellulosa*. Biochem. J. 305:1005-1010; Tamaru et al. (1995) Purification and characterisation of an extracellular β-1,4-mannanase from a marine bacterium *Vibrio* sp. strain MA-138, Appl. Environ. Microbiol. 61:4454-4458) and thermophilic bacteria (Duffaud et al. (1997) Purification and characterization of extremely thermostable beta-mannanase, beta-mannosidase and alpha-galactosidase from the hyperthermophilic eubacterium *Thermotoga neapolitana* 5068, Appl. Environ. Microbiol. 64:4428-4432; Gibbs et al. (1996) Sequencing, cloning and expression of a beta-1,4-mannanase gene, manA, from the extremely thermophilic anaerobic bacterium *Caldicellulosiruptor* Rt8B.4 *FEMS Microbiol. Lett.* 141:37-43; Bicho et al. (1991) The characterization of a thermostable endo-β-mannanase cloned from *Caldocellum saccharolyticum. Appl. Microbiol. Biotechnol.* 36:337-343) have been described.

Enzymes used in large amounts in technical processes must be produced at relatively low costs to allow a commercially viable process. This entails the availability of an efficient production host which produces and ideally secrets the target enzyme at several grams per litre culture. Heterologous expression of thermostable mannanases has been described in *E. coli* (Parker et al. (2001) Galactomannanases Man2 and Man5 from *Thermotoga* Species: Growth, physiology on galactomannans, gene sequence analysis and biochemical properties of recombinant enzymes. Biotechnol. Bioeng. 75:322-333) and *S. cerevisiae* (Stalbrand et al. (1995) Cloning and expression in *Saccharomyces cerevisiae* of a *Trichoderma reesei* β-mannanase gene containing a cellulose binding domain. *Appl. Environ. Microbiol.* 61:1090-1097) with very low yield. However, *T. reesei* mannanase has been expressed in *Pichia pastoris* at 10 g/l yield (Hägglund (2002) Thesis, Lund University, Sweden). On the other hand, *Trichoderma reesei* is a well known host for the production of a variety of industrial enzymes and homologous overexpression of mannanase or thermostable mannanase variants may result in high yield of a naturally processed enzyme.

Applications of mannanase enzymes: The use of mannanase enzymes is widespread in food & feed applications, the detergent and the pulp & paper industry. The use of mannanase enzymes as feed additives has been shown to provide several beneficial effects. These benefits are seen in combination with feedstuff like guar, copra, alfalfa, palm kernel and soy which contain significant amounts of mannans.

For monogastric animals like poultry and swine mannans are largely indigestible feed components that act as antinutritional factors. Negative effects of mannans reported are reductions in animal growth, feed efficiency and nutritional value of the feed (Lee et al. (2005) Effects of guar meal by-product with and without beta-mannanase Hemicell on broiler performance. *Poult. Sci.* 84:1261-1267).

Conversely, mannanase when added to e.g. corn-soybean meal diets for laying hens increased egg production and egg weight (Jackson et al. (1999) Effects of beta-mannanase in corn-soybean meal diets on laying hen performance. *Poult. Sci.* 78:1737-1741).

Mannanase enzymes are also used in combination with other carbohydrases in animal diets which has been shown to improve growth performance and nutrient digestibility (Kim et al. (2003) Use of carbohydrases in corn-soybean meal-based nursery diets. *J. Anim. Sci.* 81:2496-2504).

Mannanase enzymes added to corn-soybean meal diets for pigs improved the feed efficiency in late-nursery pigs. Furthermore, daily gain and feed efficiency was improved in growing-finishing pigs. Additionally, the mannanase enzyme increased the lean gain of finishing pigs (Pettey et al. (2002) Effects of beta-mannanase addition to corn-soybean meal diets on growth performance, carcass traits, and nutrient digestibility of weanling and growing-finishing pigs. *J. Anim. Sci.* 80:1012-1019).

In the food industry mannanase enzymes are described for the use in the production of instant coffee where the enzyme reduces the viscosity of the coffee extracts due to hydrolysis of the coffee mannan. This leads to reduced energy cost in the drying process involved in instant coffee production.

Mannanases are used to produce specific mannooligomers that are of interest as functional food ingredients. In particular mannooligomers with a prebiotic functionality are of interest in this application. In such applications plant derived mannopolymers are subjected to hydrolysis by mannanases.

Furthermore, mannanase enzymes are used in detergent compositions because of their mannan hydrolytic activity. Here the mannanases facilitate the removal of food and cosmetic derived stains/soils that often comprise mannan containing additives like stabilizers, emulsifiers and thickeners. These additives make up an important part of consumer relevant stains/soils.

For such detergent applications mannanases are also used in combination with other enzymes that are found in detergent formulations like amylases, cellulases, lipases, pectinases, proteases and endoglucanases.

In a more specific cleaning application mannanases are applied to remove biofilms from surfaces or tubings that need to be free from microbials like pharmaceutical equipment. In this application mannanases are often used in combination with detergents and other enzymes like carbohydrases and proteases.

Another application for mannanase enzymes is the enzyme-aided bleaching of paper pulp. Here mannanases can complement the action of xylanases that are traditionally used in enzyme-aided bleaching of pulp. Due to its different activity the mannanase hydrolyses e.g. the glucomannan parts of the pulp fibres that are not hydrolyzed by xylanases.

The effect of enzymatic treatment on pulp bleachability depends on the one hand on the wood species and on the other hand on the type of cooking (e.g. kraft pulp (sulfate cooking) or sulfite method). In this respect mannanase treatment was found to be especially effective in improving the bleachability of pulps produced by modified or continuous pulping methods that generally exhibit a low lignin content (Suurnakki et al. (1997) Hemicellulase in the bleaching of chemical pulps. *Adv. Biochem. Eng. Biotechnol.* 57: 261-287).

Moreover, mannanase enzymes are applied in the process of oil and gas well stimulation by hydraulic fracturing. Here mannanase enzymes reduce the viscosity of a process relevant guar solution that is, mixed with sand, applied in the application and needs to be liquefied in a certain stage of the application. As the process of hydraulic fracturing typically involves high temperatures, thermostable mannanases are desired (McCutchen et al. (1996) Characterization of Extremely Thermostable Enzymatic Breakers (Alpha-1,6-Galactosidase and Beta-1,4-Mannanase) from the Hyperthermophilic Bacterium *Thermotoga-Neapolitana*-5068 for Hydrolysis of Guar Gum. *Biotechnology, and Bioengineering* 52: 332-339).

Another application for mannanases is the controlled release of drugs or other material from matrices that are composed of cross linked galactomannans. It was for example shown that a chemically cross linked galactomannan hydrogel can serve as a colon specific drug delivery system in a way that the release of bacteria that secrete mannanases.

Most of the technical processes detailed above are performed at elevated temperatures, thus enzymes with a high thermal stability are preferable. Although thermostable mannanases have been described, they potentially suffer from poor technical producibility. *Trichoderma reesei* is well established for the high yield production of proteins, in particular homologous proteins, yielding tens of grams per litre culture. Thermostability is also required for feed additives that are incorporated in the feed mixtures prior to a pelleting procedure that comprises high temperatures. Additionally, mannanases applicable as feed additives need to be low-pH- and pepsin-stable and have to be active at low pH in order to be able to work efficiently in the stomach of e.g. monogastric animals.

In USRE38,047 a hemicellulase supplement is disclosed which serves to improve the energy efficiency of hemicellulose-containing animal feed. However, despite being from bacterial origin (Bacillus), the said hemicellulase is a wild type hemicellulase lacking improved properties introduced into the enzyme by design. Above all, the said hemicellulase has only limited thermostability. When treated with a temperature above 60° C., enzyme activity drops significantly. This is a severe disadvantage when it comes to the pre-treatment of animal feed. Here feed pelleting is an important process which improves supply of feed as well as the quality in terms of digestibility and microbial load. Microbial load is significantly reduced at elevated pelleting temperature, e.g. 70° C. Due to the fact that the said mannanase features only limited heat stability, the mannanase has to be added to the feed after pelleting. This is usually accomplished by spraying the said mannanase on the pellets, which however provides large difficulties in terms of precise and reproducible enzyme dosage. Additionally this is an extra process step which is economically not favourable.

SUMMARY OF THE INVENTION

The objective of the present invention is to provide thermostable, pH-stable and pepsin-stable mannanases, active at low pH values as present in the stomach and upper intestine of animals and the crop, stomach and upper intestine of poultry. Furthermore, it is an object of the invention to provide mannanases with a high sequence homology to the *Trichoderma reesei* mannanase, allowing high yield production in that organism. Therefore, the present invention is also directed to a method for the production of mannanases in *Trichoderma reesei*, active at low pH values as present in the stomach and upper intestine of animals and the crop, stomach and upper intestine of poultry. It is yet another object of the present invention to provide a mannanase which can be added to animal feed prior to pelleting, in order to allow a precise and reproducible enzyme dosage, and avoid an additional spraying step in the feed preparation.

It was found that the above objects can be solved by certain modifications of the primary sequence of the mannanase protein. The invention thus provides (1) a modified β-mannanase which is derived from the wild-type *Trichoderma reesei* mannanase shown in SEQ ID NO:1 by insertion, deletion and/or substitution of at least one amino acid residue of said wild-type mannanase and has one or more of the following enhanced phenotypes relative to the wild-type mannanase: increased thermostability, increased proteolytic stability, increased specific activity and improved stability at low pH, or variants, modified forms, homologs, fusion proteins, functional equivalents or fragments thereof;

(2) a nucleic acid molecule encoding the modified mannanase as defined in (1) above or the complement thereof;

(3) a vector comprising the nucleic acid molecule as defined in (2) above;

(4) a host cell being transformed with the vector as defined in (3) above and/or comprising the DNA as defined in (2) above;

(5) a method for preparing the modified mannanase as defined in (1) above, which comprises culturing the host cell as defined in (4) above and isolating the modified mannanase from the culture;

(6) a composition comprising the modified mannanase as defined in (1) above; and (7) the use of the modified mannanase as defined in (1) above for food and feed processing, for coffee extraction and the processing of coffee waste, as a supplement to food and feed, for enzyme aided bleaching of paper pulps, as bleaching and/or desizing agent in textile industry, for oil and gas well stimulation by hydraulic fracturing, as detergent, for removal of biofilms and in delivery systems, or for the processing of renewable resources intended for the production of biological fuels.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications referenced above.

BRIEF DESCRIPTION OF THE FIGURES

FIG. 9: Comparison of the release of mannose from guar gum, locust bean gum and konjac glucomannan, all treated with a mannanase according to the invention.

DEFINITIONS

Figure 1:
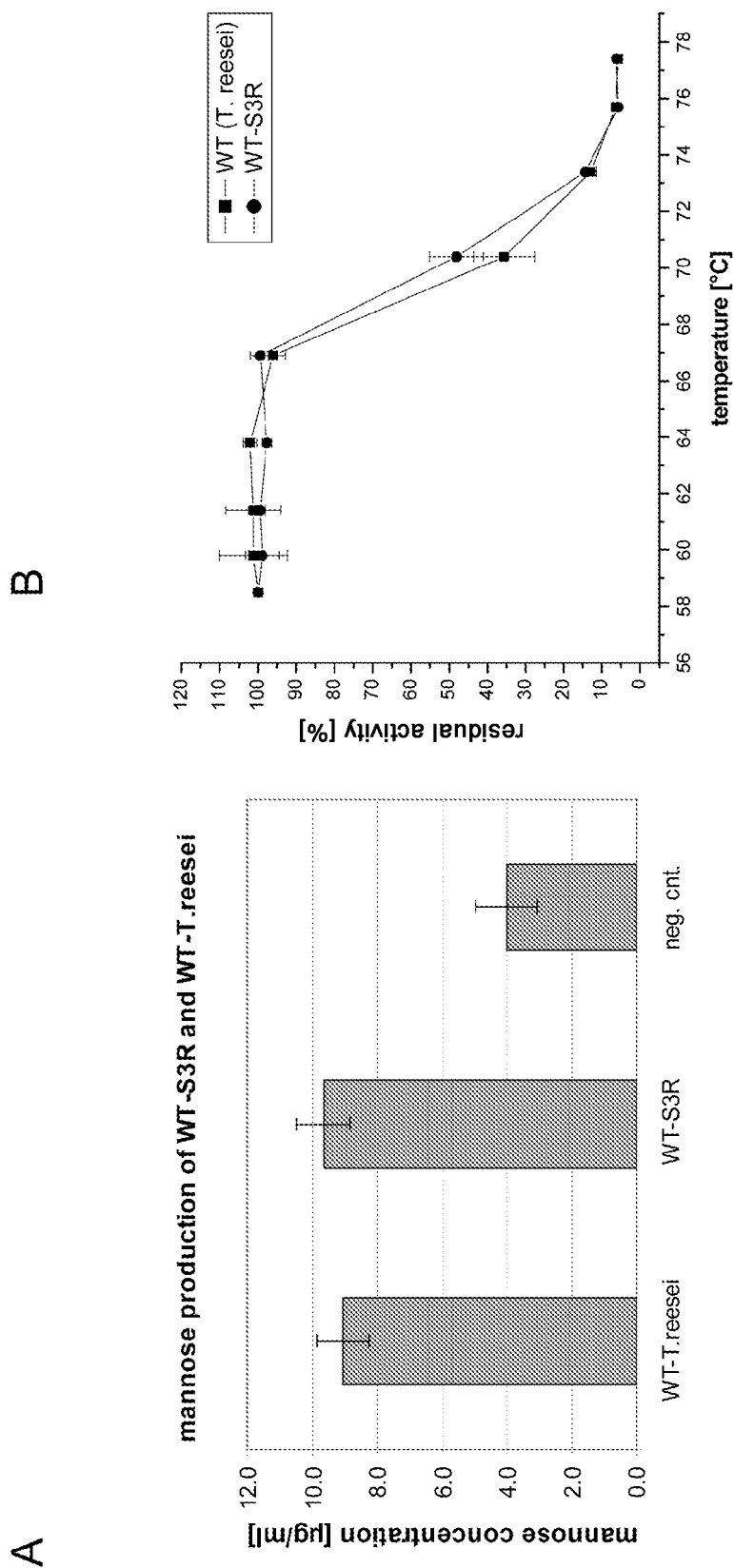
FIG. 1: Comparison of the *Trichoderma reesei* mannanase and the S3R-variant with respect to thermal stability and activity.

The term "mannanase" refers to any enzyme capable of hydrolyzing polyose chains that are composed of mannose units (mannopolymers or polymannoses). "Mannanase" therefore comprises both endomannanases and exomannanases which cleave mannopolymers internally or from the terminal ends of the polymer, respectively.

The term "functional equivalent of a mannanase" or "functional equivalent thereof" means that the enzyme has to have about the same functional characteristics as that of *Trichoderma reesei* mannanase.

The term "modified form" or "variant" means that the enzyme has been modified from its original form (wild-type, wt) but retains the same enzymatic functional characteristics as that of *Trichoderma reesei* mannanase.

The term "fusion proteins" comprises all proteins derived from the parent mannanase or any variant thereof by covalently fusing additional amino-acid sequences at the C- and/or N-terminus. The source and composition of the additional amino-acid sequence is either natural from any living organisms or virus or unnatural.

The term "functional fragment" or "effective fragment" means a fragment or portion of the *Trichoderma reesei* mannanase or derivative thereof that retains about the same enzymatic function or effect.

The term "homologous mannanase" according to the present invention comprises any enzyme with a sequence identity of at least 70% or preferably at least 80%, 85%, 90%, 95%, 97% or 99% to the parent mannanase.

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "position" in a polynucleotide or polypeptide refers to specific single bases or amino acids in the sequence of the polynucleotide or polypeptide, respectively.

The term "polypeptide" comprises proteins such as enzymes, antibodies and the like, medium-length polypeptides such as peptide inhibitors, cytokines and the like, as well as short peptides down to an amino acid sequence length below ten, such as peptidic receptor ligands, peptide hormones, and the like.

The term "mannanase variants" means any mannanase molecule obtained by site-directed or random mutagenesis, insertion, deletion, recombination and/or any other protein engineering method that leads to mannanases that differ in their amino acid sequence from the parent mannanase. The terms "wild type mannanase", "wild type enzyme", or "wild type" in accordance with the invention describe a mannanase enzyme with an amino acid sequence found in nature.

The "parent mannanase" can be either an isolated wild-type mannanase, or one or more mannanase variants selected from a library of mannanases.

The term "mannanase library" describes at least one mannanase variant or a mixture of mannanases in which every single mannanase, resp. every mannanase variant, is encoded by a different polynucleotide sequence.

The term "gene library" indicates a library of polynucleotides that encodes the library of mannanases.

The term "isolated" describes any molecule separated from its natural source.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes. Amino acid residues are abbreviated according to the following Table 1 either in one- or in three-letter code.

TABLE 1

| Amino acid abbreviations | | |
|---|---|---|
| Abbreviations | | Amino acid |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Mutations are described by use of the following nomenclature: amino acid residue in the protein scaffold; position; substituted amino acid residue(s). According to this nomenclature, the substitution of, for instance, an alanine residue for a glycine residue at position 20 is indicated as Ala20Gly or A20G. The deletion of alanine in the same position is shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as Δ(Ala20-Gly21) or Δ(A20-G21). When a sequence contains a deletion in comparison to the parent protein used for numbering, an insertion in such a position (e.g. an alanine in the deleted position 20) is indicated as *20Ala or *20A. Multiple mutations are separated by a plus sign or a slash. For example, two mutations in positions 20 and 21 substituting alanine and glutamic acid for glycine and serine, respectively, are indicated as A20G+E21S or A20G/E21S. When an amino acid residue at a given position is substituted with two or more alternative amino acid residues these residues are separated by a comma or a slash. For example, substitution of alanine at position 30 with either glycine or glutamic acid is indicated as A20G,E or A20G/E, or A20G, A20E. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the Table 2 below, which describes a generally accepted Venn diagram grouping of amino acids.

TABLE 2

Venn diagram grouping amino acids

| Set | | Sub-set | |
|---|---|---|---|
| Hydrophobic | F W Y H K M I L V A C | Aromatic | F W Y H |
| | | Aliphatic | I L V |

TABLE 2-continued

Venn diagram grouping amino acids

| Set | | Sub-set | |
|---|---|---|---|
| Polar | W Y H K R E D C S T N Q | Charged | H K R E D |
| | | Positively charged | H K R |
| | | Negatively charged | E D |
| Small | V C A G S P T N D | Tiny | A G S |

The term "catalytic activity" or "activity" describes quantitatively the conversion of a given substrate under defined reaction conditions. The term "residual activity" is defined as the ratio of the catalytic activity of the enzyme under a certain set of conditions to the catalytic activity under a different set of conditions. Therefore the residual activity $a_i$ is given by $a_i = v_i/v_0$ where v denotes any measure of catalytic activity and $a_i*m100$ is the relative activity in percent. The term "specific activity" describes quantitatively the catalytic activity per amount of enzyme under defined reaction conditions.

The term "thermostability" describes the property of a protein to withstand a limited heat exposure without losing its activity at lower temperatures, e.g. at the temperature where its activity can be measured.

The term "pH-stability" describes the property of a protein to withstand a limited exposure to pH-values significantly deviating from the pH where its stability is optimal, e.g. more than one pH-unit above or below the pH-optimum, without losing its activity under conditions where its activity can be measured.

The term "proteolytic stability" describes the property of a protein to withstand a limited exposure to proteases under conditions where the proteases are active, without losing activity under conditions where its activity can be measured.

The term "plasmid", "vector system" or "expression vector" means a construct capable of in vivo or in vitro expression. In the context of the present invention, these constructs may be used to introduce genes encoding enzymes into host cells.

The term "host cell" in relation to the present invention includes any cell that comprises either the nucleic acid molecule or an expression vector as described above and which is used in the recombinant production of an enzyme having the specific properties as defined herein or in the methods of the present invention.

The "inactivation temperature" is defined as the temperature at which the residual activity of a mannanase enzyme after incubation for a certain duration and subsequent cooling to room temperature is 50% of the residual activity of the same mannanase enzyme incubated for the same duration under the same conditions at room temperature.

The term "renewable resources" refers to biomass substrates which are grown and harvested, like crops, straw, wood and wood products. The term "biological fuels" refers to solid, liquid, or gas fuel consisting of, or derived from biomass, like Biodiesel, Biogas, Vegetable oil, Bioethanol, BioHydrogen, Bio-Dimethyl ether, Biomethanol, BTL ("Biomass to liquid")-Fuel, GTL ("Gas to liquid")-Fuel, and the like.

DETAILED DESCRIPTION OF THE INVENTION

The present invention reveals enzymes with an amino-acid sequence derived from the amino acid sequence shown in SEQ ID NO:1 or variants, modified forms, homologs, fusion proteins, functional equivalents or fragments thereof, or comprising one or more insertions, deletions or mutations or any combination thereof. A homologous mannanase according to the present invention comprises any enzyme with a sequence identity of at least 70% or preferably at least 80%, 85%, 90%, 95%, 97% or 99%, preferably to SEQ ID NO:1.

The term "functional equivalent thereof" means that the enzyme has to have about the same functional characteristics as that of *Trichoderma reesei* mannanase. The term "modified form" or "variant" means that the enzyme has been modified from its original form but retains the same enzymatic functional characteristics as that of *Trichoderma reesei* mannanase. In particular, the terms "variant" or "modified form" encompass mannanase enzymes with an amino acid sequence derived from the amino acid sequence of the parent/wild-type mannanase and having one or more amino acid substitutions, insertions, deletions or any combination thereof, which together are referred to as mutations.

"Fusion proteins" comprise all proteins derived from the parent mannanase or any variant thereof by covalently fusing an additional amino-acid sequence to the C- and/or N-terminus of the parent mannanase.

Modified forms or variants may display altered enzyme characteristics compared to the parent enzyme. Preferably, modified forms or variants have one or more of the following enhanced phenotypes: increased thermostability; and/or an increased proteolytic (for example against pepsin) stability; and/or an increased specific activity and/or improved stability at low pH. The term "functional" or "effective" fragment means a fragment or portion of the *Trichoderma reesei* mannanase that retains about the same enzymatic function or effect.

It is also understood that the present invention comprises all molecules that are derived from the parent mannanase and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These posttranslational modifications may or may not have an influence on the physical or enzymatic properties of the enzymes as explored herein.

Preferably, the said changes lead to improved properties of the enzyme such as:
1. higher thermostability and/or
2. higher specific activity and/or
3. improved stability at low pH and/or
4. higher resistance against proteolytic cleavage by proteases such as pepsin; and/or
5. high residual activity at low pH.

In preferred embodiments of the present invention, the modified mannanase has a substitution at one or more of the positions 4, 7, 11, 13, 31, 41, 66, 70, 74, 97, 101, 113, 132, 146, 148, 170, 173, 181, 182, 185, 186, 187, 189, 201, 207, 215, 216, 220, 252, 255, 259, 274, 280, 281, 282, 313, 316, 317, 325, 331, 341, 345, 351, 352, relative to the numbering of wild-type mannanase given in SEQ ID NO:1. These positions are characterised in that mutagenesis of the enzyme at these positions leads to improvement in the desired enzyme characteristics.

Another preferred embodiment of the invention comprises sequences in which the insertion, deletion or mutation or combination thereof is located in the second half of the molecule, e.g. the amino acid number where changes occur is higher than 200 according to the numbering given in SEQ ID NO:1.

Specifically, the following substitutions represent preferred embodiments of the invention:

In a preferred embodiment of the invention the amino acid N173 is substituted by A, C, D, E, F, G, H, I, K, L, M, P, Q, R, S, T, V, W or Y. In a more preferred embodiment N173 is substituted by A, C, D, G, H, S, P, Q, T or V, and in an even more preferred embodiment N173 is substituted by A, C, H, S, T or V, and in a most preferred embodiment N173 is substituted by H.

In a preferred embodiment of the invention the amino acid V181 is substituted by A, C, D, E, F, G, H, I, K, L, M, N, P, Q, R, S, T, W or Y. In a more preferred embodiment V181 is substituted by A, C, F, G, H, I, L, M, W or Y and in an even more preferred embodiment V181 is substituted by A, I, L or M, and in a most preferred embodiment V181 is substituted by A.

In a preferred embodiment of the invention the amino acid V148 is substituted by A, C, D, E, F, G, H, I, K, L, M, N, P, Q, R, S, T, W or Y. In a more preferred embodiment V148 is substituted by A, C, F, G, H, I, L, M, W or Y and in an even more preferred embodiment by A, I or L, and in a most preferred embodiment V148 is substituted by 1.

In a preferred embodiment of the invention the amino acid V187 is substituted by A, C, D, E, F, G, H, I, K, L, M, N, P, Q, R, S, T, W or Y. In a more preferred embodiment V187 is substituted by A, C, F, G, H, I, L, M, W or Y, and in an even more preferred embodiment V187 is substituted by A, I, L or M, and in a most preferred embodiment V187 is substituted by M.

In a preferred embodiment of the invention the amino acid T201 is substituted by A, C, D, E, F, G, H, I, K, L, M, N, P, Q, R, S, V, W or Y. In a more preferred embodiment T201 is substituted by A, C, H, N, P, Q, S, V or Y, and in an even more preferred embodiment T201 is substituted by A, C, N, Q, S or V, and in a most preferred embodiment T201 is substituted by S.

In a preferred embodiment of the invention the amino acid L207 is substituted by A, C, D, E, F, G, H, I, K, M, N, P, Q, R, S, T, V, W or Y. In a more preferred embodiment L207 is substituted by A, C, F, G, H, I, M, V, W or Y, and in an even more preferred embodiment L207 is substituted by A, F, G, H, I or V, and in a most preferred embodiment L207 is substituted by F.

In a preferred embodiment of the invention the amino acid A215 is substituted by C, D, E, F, G, H, I, K, L, M, N, P, Q, R, S, T, V, W or Y. In a more preferred embodiment A215 is substituted by C, F, G, H, I, L, M, T, V, W or Y, and in an even more preferred embodiment A215 is substituted by C, F, G, H, I, L or T and in a most preferred embodiment A215 is substituted by T.

In a preferred embodiment of the invention the amino acid Y220 is substituted by A, C, D, E, F, G, H, I, K, L, M, N, P, Q, R, S, T, V or W. In a more preferred embodiment Y220 is substituted by A, F, H, I, L, M, N, P, V or W and in an even more preferred embodiment Y220 is substituted by F, H, W or Y, and in a most preferred embodiment Y220 is substituted by F.

In a preferred embodiment of the invention the amino acid F274 is substituted by A, C, G, H, I, L, M, V, W or Y. In a more preferred embodiment F274 is substituted by C, H, I, L, M, V, W or Y, and in an even more preferred embodiment F274 is substituted by L, H, W or Y, and in a most preferred embodiment F274 is substituted by L.

In a preferred embodiment of the invention the amino acid Q280 is substituted by A, C, D, E, F, G, H, I, K, L, M, N, P, R, S, T, V, W or Y. In a more preferred embodiment Q280 is substituted by C, D, E, H, K, N, R, S, T or Y, and in an even more preferred embodiment Q280 is substituted by C, H, N, S or T, and in a most preferred embodiment Q280 is substituted by R.

In a preferred embodiment of the invention the amino acid N282 is substituted by A, C, D, E, F, G, H, I, K, L, M, P, Q, R, S, T, V, W or Y. In a more preferred embodiment N282 is substituted by C, D, E, H, K, Q, R, S, T or Y, and in an even more preferred embodiment N282 is substituted by C, D, H, Q, S or T, and in a most preferred embodiment N282 is substituted by D.

In a preferred embodiment of the invention the amino acid N331 is substituted by A, C, D, E, F, G, H, I, K, L, M, P, Q, R, S, T, V, W or Y. In a more preferred embodiment N331 is substituted by C, D, E, H, K, Q, R, S, T or Y, and in an even more preferred embodiment N331 is substituted by C, H, Q, S or T, and in a most preferred embodiment N331 is substituted by S.

In a preferred embodiment of the invention the mannanase variants are derived from the amino acid sequence given in SEQ ID NO:1 by introducing two or more of the following individual substitutions in any combination: N173H; V181A; V148I; V187M; T201S; L207F; A215T; Y220F; F274L; Q280R; N282D; N331S.

In a particular preferred embodiment of the invention the mannanases are derived from the amino acid sequence given in SEQ ID NO:1 and comprise one or more of the following combinations of substitutions:

1. substitution F274L is combined with A215T
2. substitution F274L is combined with N282D
3. substitution F274L is combined with A215T and N282D
4. substitution F274L is combined with Y220F
5. substitution F274L is combined with V187M
6. substitution F274L is combined with V181A
7. substitution F274L is combined with V148I
8. substitution F274L is combined with N173H
9. substitution F274L is combined with N331S
10. substitution F274L is combined with N173H and N331S
11. substitution F274L is combined with L207F
12. substitution F274L is combined with T201S
13. substitution F274L is combined with Q280R
14. substitution F274L is combined with T201S and Q280R
15. substitution F274L is combined with T201S and L207F In a further preferred embodiment of the invention any one of the combinations 1 to 15 listed above may be combined to yield a mannanase variant.

In another aspect, the invention provides an isolated and/or purified nucleic acid molecule or nucleic acid molecule coding for the enzyme comprising the amino acid sequence corresponding to *Trichoderma reesei* mannanase, or a homolog thereof. Preferably said isolated and/or purified nucleic acid molecule encodes a polypeptide comprising the amino acid sequence as shown in SEQ ID NO:1 or a sequence having at least 75% identity (homology) thereto or to an effective fragment thereof. In one embodiment, the nucleic acid molecule encodes a polypeptide comprising SEQ ID NO:1 and including mutations at the preferred positions listed herein or any of the specific mutations or combinations of mutations listed herein.

Yet basically, several amino-acid substitutions with respect to the wild type mannanase have turned out beneficial in terms of thermostability, both by themselves and/or in combination with others. These substitutions are shown in Table 3A and 3B. Moreover, several amino acid substitutions have as well turned out to be quite beneficial in terms of pH stability and stability against proteases (particularly Pepsin). These substitutions are shown in Table 5.

In yet a further aspect, the invention relates to a nucleic acid molecule and to the use of a nucleic acid molecule selected from the group consisting of (a) a nucleic acid molecule encoding a modified mannanase according to the above description,
(b) a nucleic acid molecule encoding for a derivative of the modified mannanase according to the above description, in which derivative one or more amino acid residues are conservatively substituted;
(c) the nucleic acid molecule presented as SEQ ID NO:2,
(d) a nucleic acid molecule that is a variant, homologue, derivative or fragment of the nucleic acid molecule presented as SEQ ID NO:2;
(e) a nucleic acid molecule that is the complement of the nucleic acid molecule set out in SEQ ID NO:2;
(f) a nucleic acid molecule that is the complement of a variant, homologue, derivative or fragment of the nucleic acid molecule presented as SEQ ID NO:2;
(g) a nucleic acid molecule that is capable of hybridizing to the nucleic acid molecule set out in SEQ ID NO:2;
(h) a nucleic acid molecule that is capable of hybridizing to a variant, homologue, derivative or fragment of the nucleic acid molecule presented as SEQ ID NO:2;
(i) a nucleic acid molecule that is the complement of a nucleic acid molecule that is capable of hybridizing to the nucleic acid molecule set out in SEQ ID NO:2;
(j) a nucleic acid molecule that is the complement of a nucleic acid molecule that is capable of hybridizing to a variant, homologue, derivative or fragment of the nucleic acid molecule presented as SEQ ID NO:2;
(k) a nucleic acid molecule that is capable of hybridizing to the complement of the nucleic acid molecule set out in SEQ ID NO:2;
(l) a nucleic acid molecule that is capable of hybridizing to the complement of a variant, homologue, derivative or fragment of the nucleic acid molecule presented as SEQ ID NO:2.
(m) a nucleic acid molecule having a sequence identity of at least 95% with any of the nucleic acid molecules of a)-l) and encoding for a mannanase,
(n) a nucleic acid molecule having a sequence identity of at least 70% with any of the nucleic acid molecules of a)-b) and encoding for a mannanase, and/or
(o) a fraction or a complement of any of the nucleic acid molecules of a)-n).

A nucleotide is considered to hybridize to one of the above nucleotides if it is capable of hybridizing under conditions of medium stringency, more preferably high stringency, even more preferably under very high stringency conditions.

To prepare a hybridization blot, standard molecular biology protocols for blotting may be used (e.g. Southern blotting for DNA hybridizations). The amount of target DNA depends on the relative abundance of the target sequence. If a pure target sequence is to be used, between 1 and 5 picograms of DNA per kilobase of polynucleotides are preferred. Typically, the detection limit is about 0.5 pg DNA for a radioactive probe with specific activity of $10^9$ dpm/mg which is equivalent to a single-copy gene 500 bp in length in 3.3 mg genomic DNA of a complex genome (e.g. human). In practice one will use approx. 10 mg of genomic DNA—for example to screen for organisms, such as micro-organisms, which contain a mannanase encoding polynucleotide of the invention. If the target DNA is bacterial or a plasmid one will have to dilute the DNA accordingly to avoid overexposure. The target DNA is blotted, e.g. by dot blotting, or via blotting from an electrophoresis gel. Preferred conditions are described in 'Membrane Transfer and Detection Methods, Amersham International plc, UK. —PI/162/85/1). Hybond N+ positively charged nylon membrane is preferably used (Amersham Life Science). The probe is preferably prepared according to Pharmacia's 'Ready to Go DNA™ labeling kit' to prepare a probe of >1×10$^9$ dpm/microgram. The probe is used in hybridization buffer at a concentration of 1×10$^6$ dpm per millilitre hybridization buffer. Blots are preferably prehybridized in hybridization buffer (6×SSC, 5× Reinhardt's solution, and 0.5% SDS, and denatured salmon sperm DNA to 100 mg/ml buffer) for an hour at 65° C., followed by hybridization in hybridization buffer containing the denatured labelled probe with shaking for 12 hours at 65° C. The blot(s) are then washed with a suitable volume wash buffer (typically 50 ml) in 2×SSC, 0.1% SDS for 30 minutes at 65° C., followed by a second wash in a suitable volume wash buffer (typically 50 ml) in either the same wash buffer (2×SSC, 0.1% SDS) for medium stringency washing, or 0.1%×SSC, 0.1% SDS for 10 minutes at 65° C. (high stringency), the second wash can be repeated at 70° C. for very high stringency washing.

The nucleic acid molecule of the present invention may comprise nucleotide sequences that encode for SEQ ID NO:1 or an effective fragment thereof or a variant, modified form, homologue or derivative thereof.

In particular, the invention provides a plasmid or vector system comprising a nucleic acid sequence encoding a mannanase as described herein or a homologue or derivative thereof. Preferably, the plasmid or vector system comprises a nucleic acid sequence coding for the amino acid SEQ ID NO:1 or a sequence that is at least 75% homologous thereto or an effective fragment thereof, or any of the derivatives of SEQ ID NO:1 described herein. Suitably the plasmid or vector system is an expression vector for the expression of any of the enzymes encoded by a nucleic acid sequence as set out in any of SEQ ID NO:2 or a sequence that is at least 75% homologous (identical) thereto in a microorganism. Suitable expression vectors are described herein. In addition, the invention provides a plasmid or vector system for expression of any of the modified enzymes or variants or functional fragments described herein. Suitable expression vectors are described herein.

Improvements in mannanase characteristics according to the present invention are directed to the use in a variety of technical processes such as but not limited to, the use as an additive to food and feed products, for food and feed processing, pulp and paper production, as well as for oil/gas well stimulation by hydraulic fractioning, generation of slow release formulations of drugs or in detergents, in particular in the removal of bacterial biofilms. In particular, improvements are directed to the enzyme stability under conditions of these or other applications and/or to the stability during stomach transit in case of a food or feed additive and/or to the activity or stability in human or animal stomach and/or intestinal tract under the acidic conditions of the upper gastrointestinal tract. Such improvements comprise, among other parameters, the increase in stability at elevated temperatures, preferably at temperatures above 60° C. and/or the increase in stability against proteolytic digestion, preferably against proteases of the digestive tract and/or the increase in stability at low pH and/or the activity at low pH values and/or the general efficiency of releasing mannose and/or oligomannoses from large polymannose containing carbohydrates.

The increase in stability at elevated temperatures is quantified by the inactivation temperature of the enzyme. The inactivation temperature is defined as the temperature at which the residual activity of a mannanase enzyme after incubation for a certain duration and subsequent cooling to room temperature is 50% of the residual activity of the same mannanase enzyme incubated for the same duration under the same conditions at room temperature. Thermostability differences are the differences in ° C. between the inactivation temperatures of two enzymes.

In a preferred embodiment of the invention the mannanase variants are applied in processes at elevated temperatures, making mannanase variants with a higher inactivation temperature desirable.

When compared with wild-type mannanase, mannanases of the invention are characterised by a higher residual activity after a thermal incubation at temperatures above the inactivation temperature of the wild-type mannanase, providing a higher process stability.

Cloning of *T. reesei* mannanase: In addition to the *Trichoderma reesei* mannanase as shown in SEQ ID NO:1 a further *Trichoderma reesei* mannanase has been cloned having the sequence of SEQ ID NO:1 with a substitution of serine to arginine at position 3 (mutation S3R). This mannanase variant was compared to the *Trichoderma reesei* mannanase according to SEQ ID NO:1 with respect to thermal stability and catalytic activity in releasing mannose from a polymannose containing substrate. The results presented in FIG. 1 demonstrate that the S3R substitution has no effect on the properties relevant to the invention and is therefore a neutral mutation. Therefore, in the context of this invention the term "wt" or "wt mannanase" "wild-type mannanase" or "*Trichoderma reesei* mannanase" is understood to comprise the mannanases according to SEQ ID NO:1 and the mannanase according to SEQ ID NO: 1 having in addition the neutral mutation S3R.

The variant termed "Com Man", which is an abbreviation for "common mannanase", is however related to the mannanase according to SEQ ID NO:1, i.e. devoid of said mutation S3R.

Figure 2:
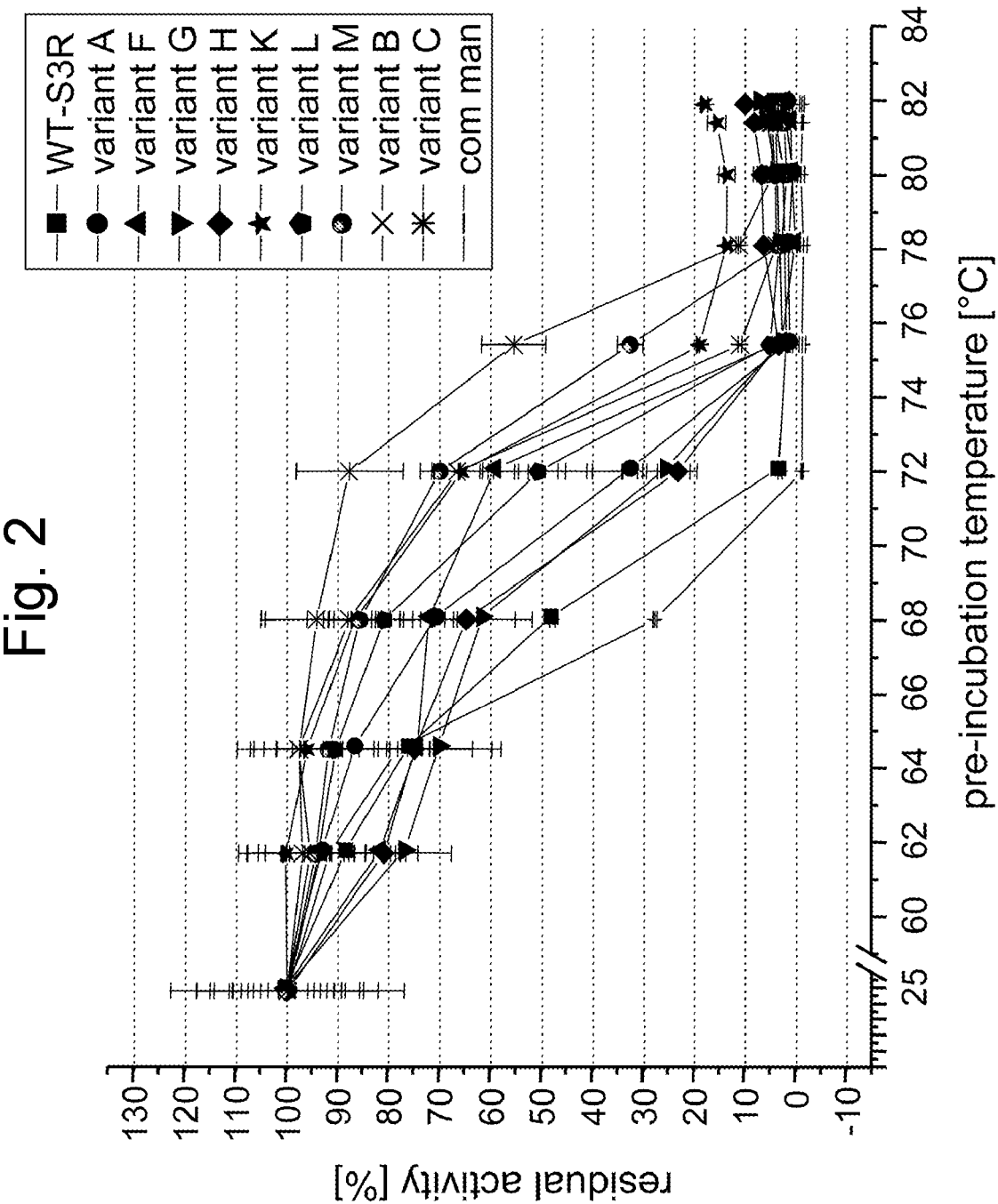
FIG. 2: Thermostability of wild-type and variant mannanases in buffer expressed as residual activity normalised to activity at 25° C.

Thermostability in buffer: In a preferred embodiment of the invention, mannanase variants have an increased residual activity and/or inactivation temperature when incubated at temperatures >60° C. for >30 min. In a more preferred embodiment the increased residual activity and/or inactivation temperature is obtained after incubation in an acetate buffer for 45 min (FIG. 2). Preferably, the inactivation temperature of the mannanase variant is >68° C., more preferably >70° C. or >72° C. or >74° C., or most preferably >76° C. Specific inactivation temperatures are given in Table 3 in conjunction with their respective mutations.

TABLE 3A

Inactivation temperatures (IT 50) for incubation in buffer of several mannanase variants with their respective amino-acid substitutions as compared to wild-type mannanase

| variant | mutation/substitution | IT50 [° C.] |
|---|---|---|
| Com Man | — | 66.7 |
| WT | — | 67.6 |
| variant A | F274L | 70.3 |
| variant B | L207F; F274L | 72.9 |
| variant C | T201S; Q280R; F274L | 75.7 |

TABLE 3A-continued

Inactivation temperatures (IT 50) for incubation in buffer of several mannanase variants with their respective amino-acid substitutions as compared to wild-type mannanase

| variant | mutation/substitution | IT50 [° C.] |
|---|---|---|
| variant F | A215T; F274L; N282D | 72.8 |
| variant G | Y220F; F274L | 68.8 |
| variant H | V187M; F274L | 69.8 |
| variant K | V181A; F274L | 72.6 |
| variant L | V148I; F274L | 72.0 |
| variant M | N173H; F274L; N331S | 74.1 |
| variant 1 | V181H | 68.7 |
| variant 2 | Q146K | 68.9 |
| variant 3 | S66P | 69 |
| variant 4 | Q97R | 69.1 |
| variant 5 | F31Y | 69.3 |
| variant 6 | V181A | 69.4 |
| variant 7 | N113Y | 70 |
| variant 8 | T201G | 70.1 |
| variant 9 | T201A | 70.1 |
| variant 10 | Q280L | 70.3 |
| variant 11 | L207F | 70.4 |
| variant 12 | Q259R | 70.5 |
| variant 13 | F274M | 70.6 |
| variant 14 | Q280R | 70.7 |
| variant 15 | N173H | 70.8 |
| variant 16 | T201S | 74.8 |
| variant 17 | T132S; N173T | 68.8 |
| variant 18 | Q11H; P170L | 69.1 |
| variant 19 | F31Y; D341E | 69.9 |
| variant 20 | N173H; G345C | 70.6 |
| variant 21 | N13D; F274L | 71.2 |
| variant 22 | F274L; Q280L | 71.9 |
| variant 23 | F274L; Q317H | 71.9 |
| variant 24 | S66P; T201S | 72.6 |
| variant 25 | L207F; F274M | 73.1 |
| variant 26 | S66P; V181A; V187L | 70.2 |
| variant 27 | V181A; T252I; N255I | 70.5 |
| variant 28 | F4Y; I70V; F274L | 71.1 |
| variant 29 | Q101R; F274L; Q281H | 72.3 |
| variant 30 | T201G; L207F; F274L | 74.3 |
| variant 31 | T201S; L207F; F274L | 76.3 |
| variant 32 | V181T; L207W; A215T; F274L | 70.7 |
| variant 33 | Q11R; Q189H; T201A; P351L | 71 |
| variant 34 | K74M; F274L; A313T; V325I | 72 |
| variant 35 | N173H; V181H; L207W; F274L | 73.7 |
| variant 36 | T201S; L207Y; F274L; Q280R | 74.2 |
| variant 37 | T201S; L207W; F274L; Q280R | 76.5 |
| variant 38 | T201S; L207R; F274L; Q280R | 76.8 |
| variant 39 | V181T; L207W; F274M; N331S; P352L | 70.4 |
| variant 40 | N173H; L207W; A215T; F274L; Q280R | 71.7 |
| variant 41 | V181H; L207W; A215T; F274L; N282D | 72.2 |
| variant 42 | N173H; V181T; T201S; L207W; F274L | 73.7 |
| variant 43 | N173H; V181H; L207W; A215T; F274L | 74.7 |
| variant 44 | V181H; L207W; A215T; F274L; Q280R; N282D | 72 |
| variant 45 | S66P; N173H; V181H; A215T; F274L; Q280S; N282D | 75 |
| variant 46 | N173H; V181T; L207W; A215T; F274L; Q280R; N282D | 75.2 |

For increased thermostability position T201 seems to be quite important. Other important positions are F274, T290 and L207. This means that all variants carrying a substitution in any of these residues represent preferred embodiments of the present invention.

In contrast thereto, the enzymes disclosed in US RE 38,047 suffer from a significant loss of activity when being treated with temperatures higher than 60° C. (see FIG. 1 of US RE 38,047), which render them unsuitable for industrial feed producing processes in which pellets are treated with the said temperatures.

Basically, several amino-acid substitutions with respect to the wild type mannanase have turned out beneficial in terms of thermostability, both alone and/or in combination with others. These substitutions are shown in Table 3B.

TABLE 3B

Amino-acid substitutions with respect to the wild type mannanase that have turned out beneficial in terms of thermostability, both by themselves and/or in combination with others.

| Wild type residue | Substituted by | Most Preferred |
|---|---|---|
| F4 | A, C, D, E, G, H, I, K, L, M, N, P, Q, R, S, T, V, W or Y | Y |
| I7 | A, C, D, E, F, G, H, K, L, M, N, P, Q, R, S, T, V, W or Y | V |
| Q11 | A, C, D, E, F, G, H, I, K, L, M, N, P, R, S, T, V, W or Y | R, H |
| N13 | A, C, D, E, F, G, H, I, K, L, M, P, Q, R, S, T, V, W or Y | D |
| F31 | A, C, D, E, G, H, I, K, L, M, N, P, Q, R, S, T, V, W or Y | Y |
| T41 | A, C, D, E, F, G, H, I, K, L, M, N, P, Q, R, S, V, W or Y | I |
| S66 | A, C, D, E, F, G, H, I, K, L, M, N, P, Q, R, T, V, W or Y | P |
| I70 | A, C, D, E, F, G, H, K, L, M, N, P, Q, R, S, T, V, W or Y | V |
| K74 | A, C, D, E, F, G, H, I, L, M, N, P, Q, R, S, T, V, W or Y | M |
| Q97 | A, C, D, E, F, G, H, I, K, L, M, N, P, R, S, T, V, W or Y | R |
| Q101 | A, C, D, E, F, G, H, I, K, L, M, N, P, R, S, T, V, W or Y | R |
| N113 | A, C, D, E, F, G, H, I, K, L, M, P, Q, R, S, T, V, W or Y | Y |
| T132 | A, C, D, E, F, G, H, I, K, L, M, N, P, Q, R, S, V, W or Y | S |
| K146 | A, C, D, E, F, G, H, I, L, M, N, P, Q, R, S, T, V, W or Y | Q |
| V148 | A, C, D, E, F, G, H, I, K, L, M, N, P, Q, R, S, T, W or Y | I |
| P170 | A, C, D, E, F, G, H, I, K, L, M, N, Q, R, S, T, V, W or Y | L |
| N173 | A, C, D, E, F, G, H, I, K, L, M, P, Q, R, S, T, V, W or Y | H, T |
| V181 | A, C, D, E, F, G, H, I, K, L, M, N, P, Q, R, S, T, W or Y | A, H, T |
| Q182 | A, C, D, E, F, G, H, I, K, L, M, N, P, R, S, T, V, W or Y | R |
| T185 | A, C, D, E, F, G, H, I, K, L, M, N, P, Q, R, S, V, W or Y | K |
| S186 | A, C, D, E, F, G, H, I, K, L, M, N, P, Q, R, T, V, W or Y | N |
| V187 | A, C, D, E, F, G, H, I, K, L, M, N, P, Q, R, S, T, W or Y | L, M |
| Q189 | A, C, D, E, F, G, H, I, K, L, M, N, P, R, S, T, V, W or Y | H |
| T201 | A, C, D, E, F, G, H, I, K, L, M, N, P, Q, R, S, V, W or Y | A, S, G |
| L207 | A, C, D, E, F, G, H, I, K, M, N, P, Q, R, S, T, V, W or Y | W, R, F, Y, S |
| A215 | C, D, E, F, G, H, I, K, L, M, N, P, Q, R, S, T, V, W or Y | T |
| Y216 | A, C, D, E, F, G, H, I, K, L, M, N, P, Q, R, S, T, V or | H |
| Y220 | A, C, D, E, F, G, H, I, K, L, M, N, P, Q, R, S, T, V or W | F |
| T252 | A, C, D, E, F, G, H, I, K, L, M, N, P, Q, R, S, V, W or Y | I |
| N255 | A, C, D, E, F, G, H, I, K, L, M, P, Q, R, S, T, V, W or Y | I |
| Q259 | A, C, D, E, F, G, H, I, K, L, M, N, P, R, S, T, V, W or Y | R |
| F274 | A, C, D, E, G, H, I, K, L, M, N, P, Q, R, S, T, V, W or Y | L, M |
| Q280 | A, C, D, E, F, G, H, I, K, L, M, N, P, R, S, T, V, W or Y | R, S, L |
| Q281 | A, C, D, E, F, G, H, I, K, L, M, N, P, R, S, T, V, W or Y | H |

TABLE 3B-continued

Amino-acid substitutions with respect to the wild type mannanase that have turned out beneficial in terms of thermostability, both by themselves and/or in combination with others.

| Wild type residue | Substituted by | Most Preferred |
|---|---|---|
| N282 | A, C, D, E, F, G, H, I, K, L, M, P, Q, R, S, T, V, W or Y | D |
| A313 | C, D, E, F, G, H, I, K, L, M, N, P, Q, R, S, T, V, W or Y | T |
| A316 | C, D, E, F, G, H, I, K, L, M, N, P, Q, R, S, T, V, W or Y | T |
| Q317 | A, C, D, E, F, G, H, I, K, L, M, N, P, R, S, T, V, W or Y | H |
| V325 | A, C, D, E, F, G, H, I, K, L, M, N, P, Q, R, S, T, W or Y | I |
| N331 | A, C, D, E, F, G, H, I, K, L, M, P, Q, R, S, T, V, W or Y | S |
| D341 | A, C, E, F, G, H, I, K, L, M, N, P, Q, R, S, T, V, W or Y | E |
| G345 | A, C, D, E, F, H, I, K, L, M, N, P, Q, R, S, T, V, W or Y | C |
| P351 | A, C, D, E, F, G, H, I, K, L, M, N, Q, R, S, T, V, W or Y | L |
| P352 | A, C, D, E, F, G, H, I, K, L, M, N, Q, R, S, T, V, W or Y | L |

In a preferred embodiment of the invention the mannanase variants are applied to an enzymatic processing of polymannose containing plant or microbial material such as, but not limited to, hemicellulose from soft- and hard-wood containing glucomannan, O-acetyl-galactoglucomannan, arabino-4-O-methylglucuronoxylan, arabinogalactan and others; polymannan-containing polysaccharides from algae, plant seeds such as ivory nut, green coffee bean and date; galactomannans from leguminoses such as guar-gum from *Cyanaposis tetragonolobus* or locust-bean-gum from *Ceratonia siliqua*; or glucomannans found in bulbs, roots, tubers or other plant tissues from different plant species.

A preferable product of enzymatic processing of polymannan-containing plant or microbial material is free mannose. Preferably, these processes are run at elevated temperatures to, e.g. increase reaction rates and/or avoid spoilage by microbial growth, providing temperature stable mannanase with an advantage.

Figure 3:
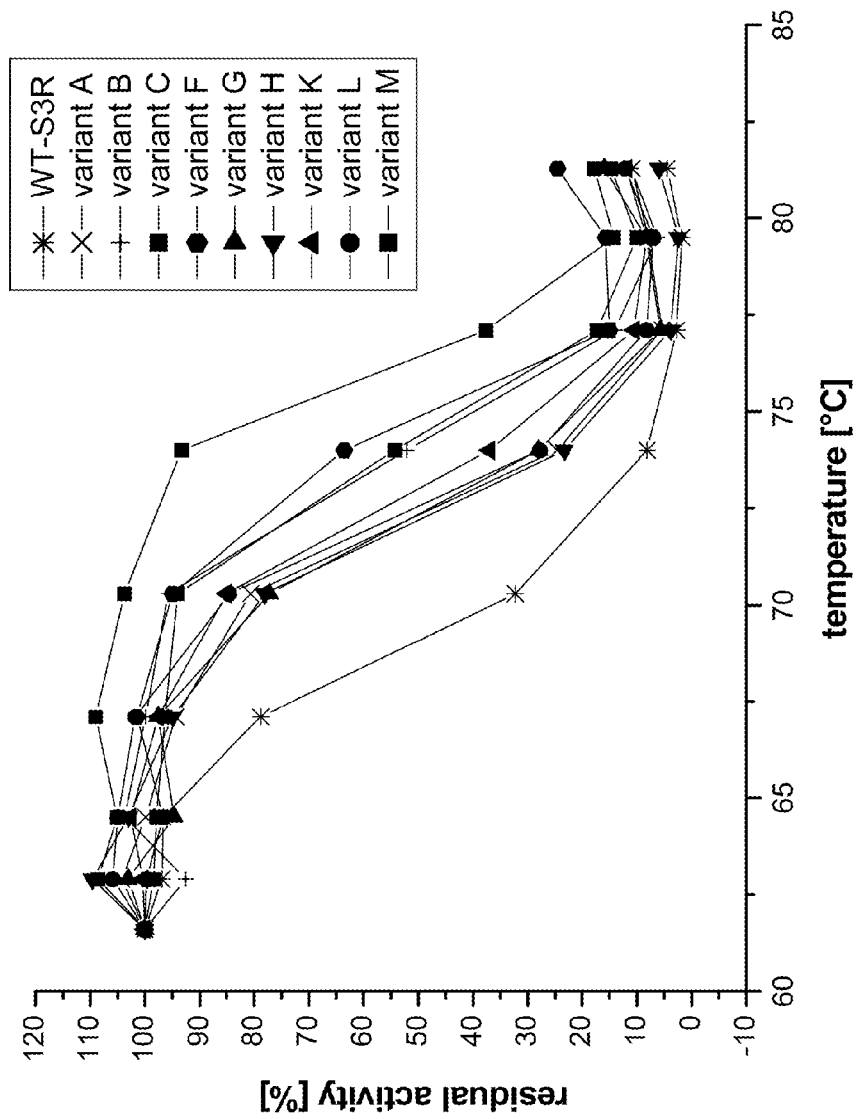
FIG. 3: Mannose yields after incubation of different mannanase variants with galactomannan substrate for 16 h at various temperatures, normalised to 63° C.

Activity on galactomannan substrate: In a preferable embodiment of the invention, when compared with wild-type mannanase the mannanase variants are characterised by a higher inactivation temperature in an enzymatic processing of polymannose-containing plant or microbial material at temperatures above the inactivation temperature of the wild-type mannanase in that process. In a more preferred embodiment the polymannose-containing plant or microbial material is galactomannan from carob, the incubation time is 16 h and the temperature is varied between 62° C. and 82° C. Specifically, FIG. 3 presents data for the release of mannose by treatment of galactomannan from carob with different mannanase variants at different temperatures after 16 hours treatment. Compared to the mannose yields at temperatures below 65° C., mannanase variants of the invention yield the same amounts of mannose at temperatures above 65° C., while the wild-type mannanase (including the S3R mannanase variant) have a reduced mannose production at temperatures above 65° C. This temperature-dependence is better expressed by the inactivation temperature, i.e. the temperature at which the normalised yield is 50% of the reference point at 62° C. Preferably, the inactivation temperature of the mannanase variant is >69° C., more preferably >70° C. or >72° C. or >74° C., or most preferably >76° C. Specific inactivation temperatures are given in Table 4 in conjunction with their respective mutations.

TABLE 4

Inactivation temperatures for mannose production from galactomannan (carob) of several mannanase variants with their respective amino-acid substitutions as compared to wild-type mannanase.

| variant | mutation/substitution | IT50 [° C.] |
|---|---|---|
| WT | — | 69 |
| variant A | F274L | 72 |
| variant B | L207F; F274L | 74 |
| variant C | T201S; Q280R; F274L | 76.1 |
| variant F | A215T; F274L; N282D | 74.2 |
| variant G | Y220F; F274L | 72.1 |
| variant H | V187M; F274L | 72 |
| variant K | V181A; F274L | 72.8 |
| variant L | V148I; F274L | 72.2 |
| variant M | N173H; F274L; N331S; | 74.1 |

Residual activity after incubation with PKE: In a further preferable embodiment of the invention, when compared with wild-type mannanase the mannanase variants are characterised by a higher residual activity in an enzymatic processing of polymannan-containing plant or microbial material at temperatures above the inactivation temperature of the wild-type mannanase in that process. In a more preferred embodiment of the invention the mannanase variants are applied to an enzymatic processing of palm kernel expeller substrate (PKE) at temperatures >60° C. for >24 hours. Specifically, in FIG. 4 residual activities of mannanase variants of the invention after a process time of 71 hours are given for process temperatures of 63° C., 67° C. and 70° C., respectively. Mannanases of the invention preferably have a residual activity of at least 20%, more preferably of at least 30%, 40%, 50%, 60%, 65% or at least 70%. In particular, mannanase variant derived from SEQ ID NO:1 by introducing the mutation F274L is characterised by a residual activity of at least 25%, mannanase variant derived from SEQ ID NO:1 by introducing the mutations L207F and F274L is characterised by a residual activity of at least 50%, mannanase variant derived from SEQ ID NO:1 by introducing the mutations T201S, Q280R and F274L is characterised by a residual activity of at least 65%.

Figure 5:
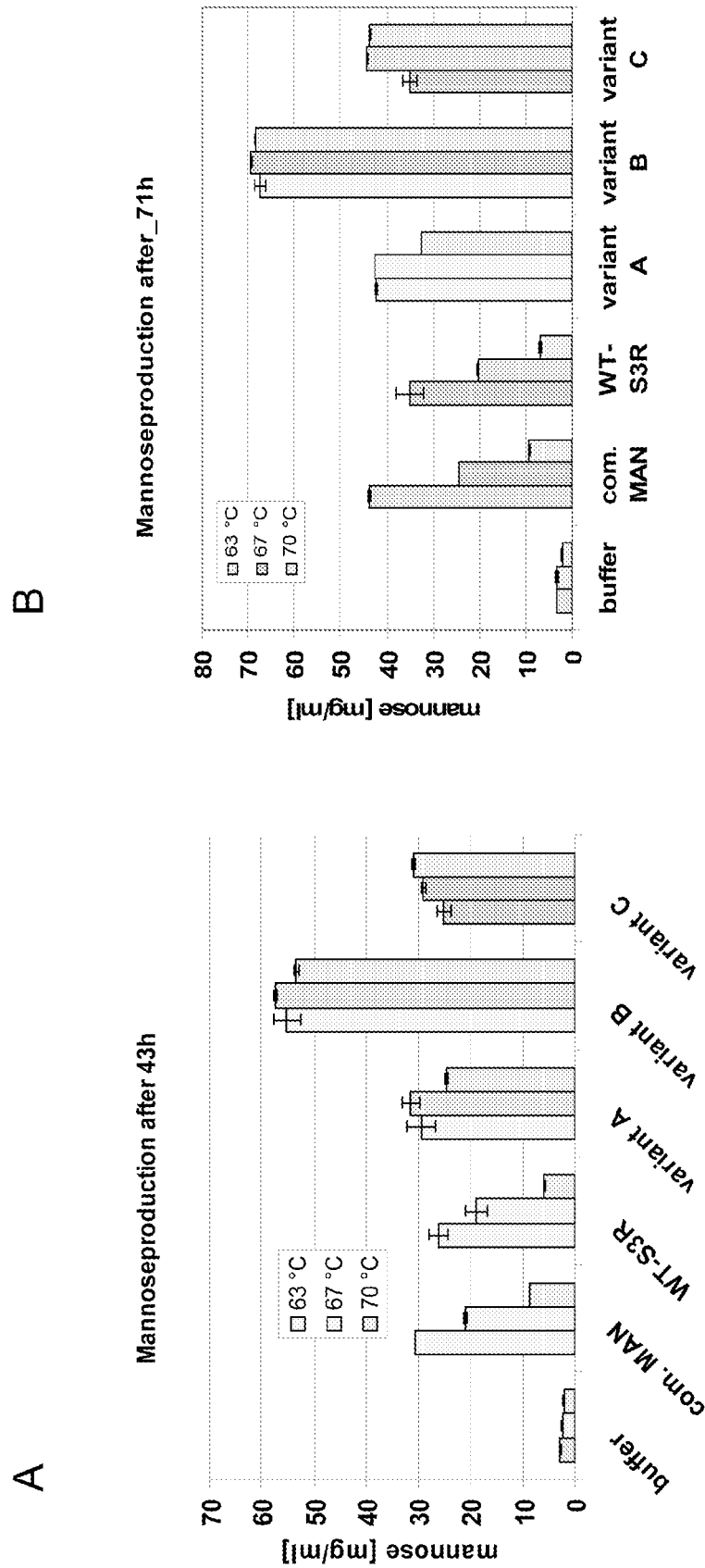
FIG. 5: Mannose yields after incubation of wild-type mannanase and different variants with PKE substrate at different temperatures and times.

Improved generation of mannose from PKE: In most technical applications the amount of enzyme is determined by the required turn-over under the particular process conditions, and for commercial reasons it is preferable to reduce the amount of enzyme as much as possible. When compared to wild-type mannanase, improved enzyme variants may provide an advantage with respect to either reduced enzyme amounts needed for the same product yield or a higher product yield when applying the same amount of enzyme. A preferred embodiment of the invention is related to the provision of enzyme variants that yield a higher amount of mannose and/or oligomannoses from polymannose-containing plant or microbial material such as PKE when compared to the same concentration of wild-type mannanase and/or yield the same amount of mannose and/or oligomannoses when applied at lower concentrations than the wild-type enzyme. In a particularly preferred embodiment the process is run at >60° C., e.g. 63° C., 67° C. or 70° C., and mannose yields determined after 43 h and 71 hours. Preferably, mannanase variants of the invention are characterised by a higher mannose yield compared to the wild-type mannanase by a factor of at least 1.1 or even more preferable by a factor of at least 1.3, 1.5, 1.7, 1.8, 1.9 or 2.0 when the process is run at 63° C. At a process temperature of 70° C. the mannanases are characterised by an improved yield by at least a factor of 2, or more preferably by a factor of >3, >4, >5, >6, >7, >8 or >9. Specifically, variant B (compare Tables 3, 4) provides an increased mannose yield by a factor of 10 at 70° C. and 71 hours process time (FIG. 5).

Mannose production at lower enzyme concentration: In a further aspect of this embodiment of the invention the enzyme variants yield at least the same amount of mannose and/or oligomannose than the wild-type when applied at lower concentrations than the wild-type enzyme. In a particular preferred embodiment the polymannose-containing plant or microbial material is PKE. Specifically, the same amount of mannose is obtained from PKE when the amount of enzyme variant is less than preferably 80%, or more preferably less than 60%, 40%, 30% or 20% of the wild-type variant (FIG. 6).

Improved pH/Pepsin stability: A further embodiment of the invention relates to the use of mannanase enzyme as a supplement to food or feed containing polymannose components. In this application mannanase is exposed to the harsh conditions of low pH and proteolysis in the human or animal gastro-intestinal tract. A preferred aspect of the invention reveals mannanase variants with improved stability at low pH and improved resistance against proteolytic inactivation (FIG. 6). Preferably, the mannanase is incubated at pH <5, more preferably at pH <4 and even more preferably at pH <3, e.g. pH 2.3. After incubation for different lengths of time and readjustment to a higher pH for activity determination, compared to the wild-type mannanase, the mannanase variants of the invention yield a higher residual activity as determined by normalising to the enzyme not incubated at pH 2.3. Preferably, after 160 min of incubation the mannanase variants yield at least 20% residual activity, or more preferably at least >40%, >50%, >60%, >70%, >80%, >90%, >95% or >99% of the reference activity. Specifically, the mannanase variant derived from SEQ ID NO:1 by introducing the substitution F274L yields at least 40% residual activity the mannanase variant derived from SEQ ID NO:1 by introducing the substitution F274L and L207F yields at least 70% residual activity and the mannanase variant derived from SEQ ID NO:1 by introducing the substitution F274L, T201S and Q280R yields at least 95% residual activity.

Figure 6:
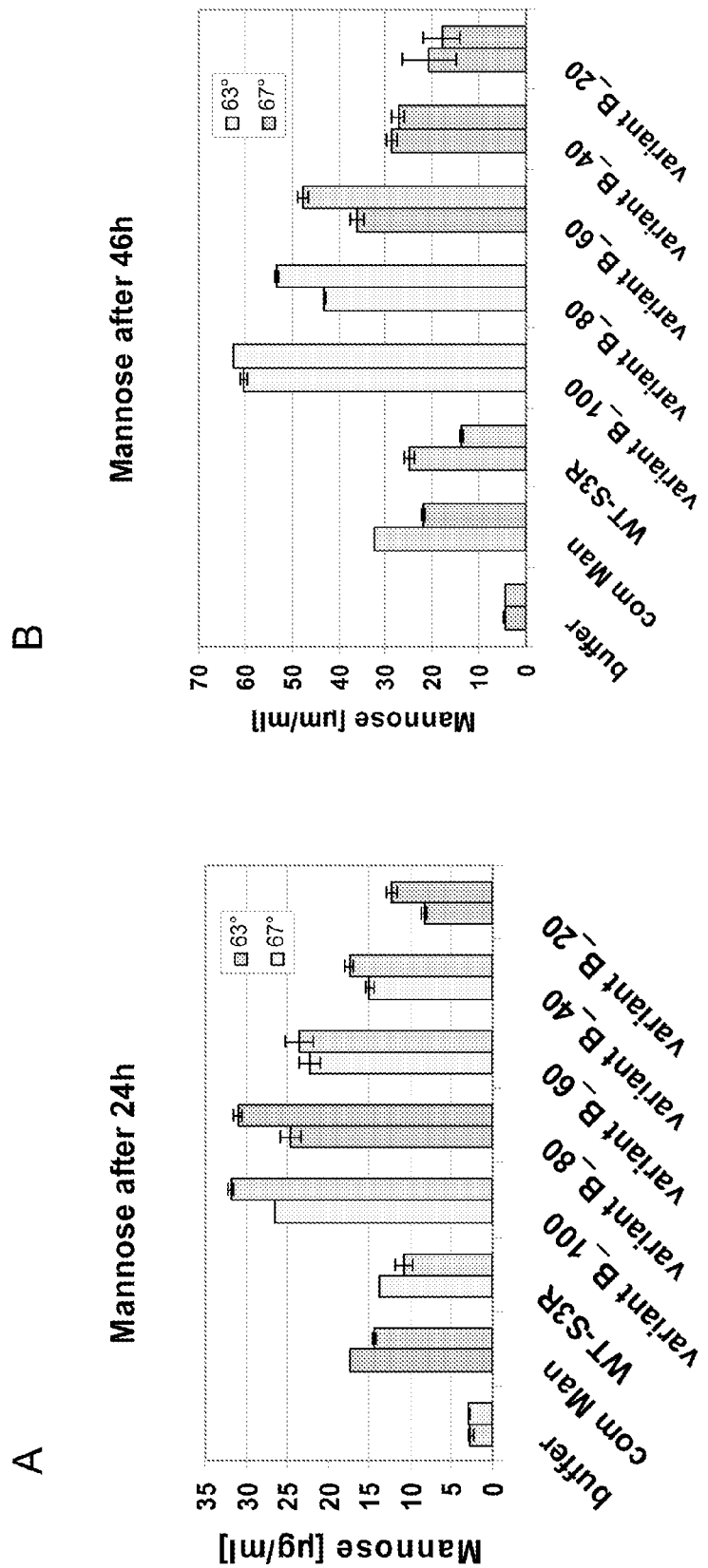
FIG. 6: Mannose yields after incubation of wild-type mannanase and different concentrations of variant B with PKE substrate at two temperatures.

Subjecting the mannanase variants simultaneously to low pH conditions and proteolytic digestion by a protease of the gastro-intestinal tract leads to stronger inactivation than by low pH alone (FIG. 6). Preferably the protease is pepsin and the pH is set at pH <5, more preferably at pH <4 and even more preferably at pH <3, e.g. pH 2.3. After incubation for different lengths of time and readjustment to a higher pH for activity determination, compared to the wild-type mannanase, the mannanase variants of the invention yield a higher residual activity as determined by normalising to the enzyme not exposed to low pH and pepsin. Preferably, after 80 min of incubation, the mannanase variants yield a residual activity of at least >20%, >40%, >50%, >60%, >70%, >75% or >80%. Specifically, the mannanase variant derived from SEQ ID NO:1 by introducing the substitution F274L yields at least 8% residual activity, the mannanase variant derived from SEQ ID NO:1 by introducing the substitution F274L and L207F (variant B) yields at least 30% residual activity, the mannanase variant derived from SEQ ID NO:1 by introducing the substitution F274L, T201S and Q280R (variant C) yields at least 80% residual activity, and the mannanase variant derived from SEQ ID NO:1 by introducing the substitution T201S, L207F and F274L (variant 31) yields at least 80% residual activity.

Improved Activity at Low pH.

Figure 8:
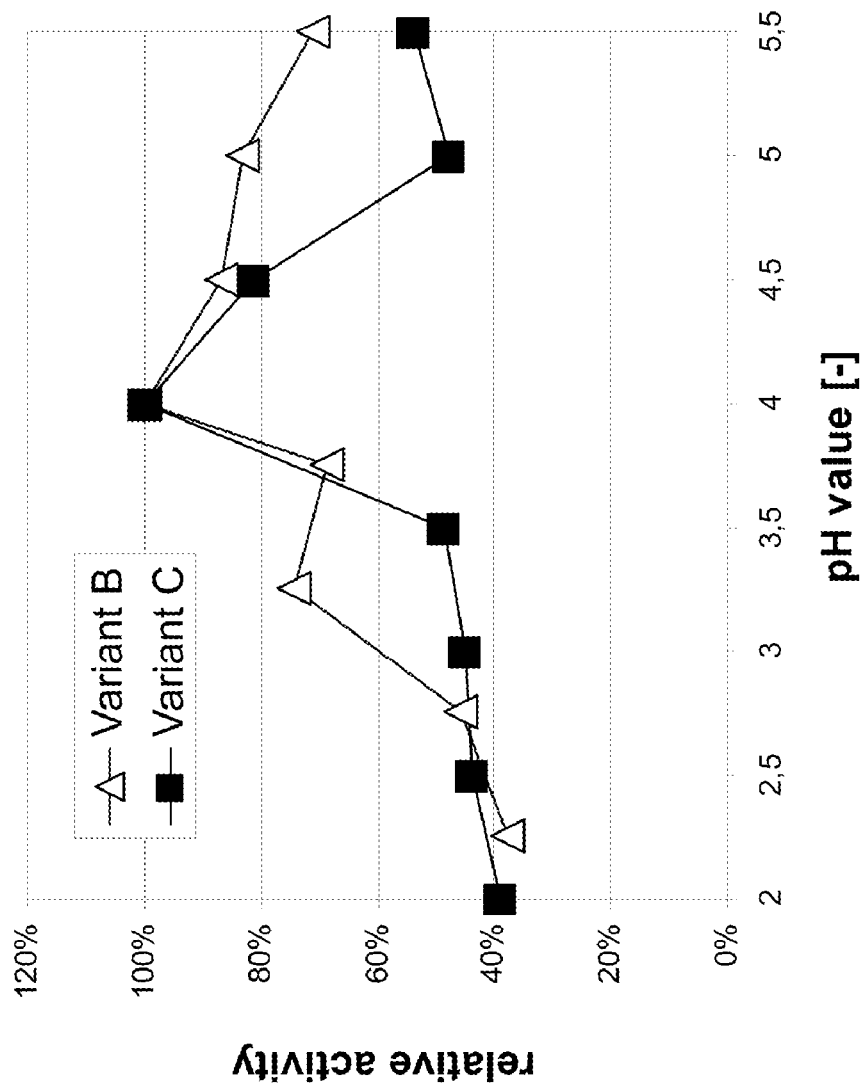
FIG. 8: Activity of different mannanase variants on PKE substrate at pH values below pH 5.5.

A further embodiment of the invention relates to the use of mannanase enzyme as a supplement to food or feed containing polymannose components (mannans, galactomannans, etc). In this application mannanase is exposed to the harsh conditions of low pH and proteolysis in the animal gastro-intestinal tract. A preferred aspect of the invention reveals mannanase variants with high activity at low pH (FIG. 8). Preferably, the mannanase is contacted with a polymannose containing substrate for different lengths of time at a pH below 5, more preferably at a pH below 4 and even more preferably at a pH below 3, e.g. pH 2.3. After completion of the reaction the activity is determined in comparison to a sample contacted with the polymannose containing substrate at optimal conditions. Preferably, after 240 min of incubation the mannanase variants yield at least 20% relative activity, more preferably at least >30%, >40%, >50%, >60%, >70%, >80%, >90%, >95% or >99% of the reference activity. Specifically, the mannanase variant (variant B) derived from SEQ ID NO:1 by introducing the substitution F274L and L207F yields at least 35% relative activity after incubation at a pH between pH 2 and pH 3, and the mannanase variant derived from SEQ ID NO:1 by introducing the substitution F274L, T201S and Q280R (variant C) yields at least 35% relative activity after incubation at a pH between pH 2 and pH 3.

Generation of mannanases: In a broad embodiment the invention provides methods of preparing mannanase enzyme variant(s).

In a preferred embodiment the method of preparing a mannanase enzyme variant comprises the following sequential steps:

a) Selecting at least one parent mannanase enzyme, wherein the at least one parent mannanase enzyme is selected from
i) a polypeptide comprising the amino acid sequence corresponding to a *Trichoderma reesei* mannanase, or a modified form, a homologous polypeptide, a variant, a functional equivalent or an effective fragment thereof, as described herein or ii) at least one mannanase enzyme variant as herein described;

b) Generating at least one mannanase variant by introducing at least one alteration of said parent mannanase enzyme which is an insertion, a deletion or a substitution or combination thereof of one or more amino acid residues in said parent mannanase enzyme to obtain at least one mannanase enzyme variant;

c) Screening at least one mannanase enzyme variant to identify an improved mannanase enzyme variant, which compared to the parent mannanase enzyme has improved property/properties selected from:
i. higher thermal stability and/or
ii. specific activity and/or
iii. proteolytic stability and/or
iv. stability at low pH-values and/or
v. high specific activity at low pH values.

d) Preparing said improved mannanase enzyme variant, preferably to produce an isolated and/or purified mannanase enzyme variant.

In a preferred embodiment, during step b) a population of mannanase enzyme variants is generated and in step c) at least a proportion of said population of mannanase enzyme variants is screened.

In a preferred embodiment step a) comprises subjecting a nucleic acid molecule encoding a parent mannanase enzyme to mutagenesis, and step b) comprises expressing the mutated nucleotide sequences obtained in step a) in a host cell, and step c) comprises screening of host cells, or extract(s) thereof, for an improved mannanase enzyme variant with said improved property/properties.

In a further embodiment after step c), and optionally d), the method further comprises at least one subsequent round of repeating steps a) to c), and optionally d) wherein, preferably, in said subsequent round(s), at least one parent mannanase enzyme of step a) is selected from said at least one mannanase enzyme variant and/or an improved mannanase variant prepared according to the method.

In a further preferable embodiment step c) comprises screening for host cells expressing an improved mannanase enzyme variant which compared to either i) said parent mannanase enzyme and/or ii) a polypeptide comprising SEQ ID NO:1 or a derivative or functional fragment thereof, has a thermal stability difference of at least 2° C.

In a further embodiment step c) comprises screening for host cells expressing an improved mannanase enzyme variant which compared to either i) said parent mannanase enzyme and/or ii) a polypeptide comprising SEQ ID NO:1 or a derivative or functional fragment thereof has a pepsin stability of at least 20%.

In a further embodiment step c) comprises screening for host cells expressing an improved mannanase enzyme variant which compared to either i) said parent mannanase enzyme and/or ii) a polypeptide comprising SEQ ID NO:1 or a derivative or functional fragment thereof has a specific activity ratio when compared to the mannanase encoded by SEQ ID NO:1 of at least 110%.

In a further embodiment step c) comprises screening for host cells expressing an improved mannanase enzyme variant which compared to either i) said parent mannanase enzyme and/or ii) a polypeptide comprising SEQ ID NO:1 or derivative or functional fragment thereof has a residual activity after incubation at low pH of at when compared to the mannanase encoded by SEQ ID NO:1 of at least 20%.

The invention also provides a method of preparing a mannanase enzyme variant, which method comprises:
a) Selecting a parent mannanase enzyme, wherein the parent mannanase enzyme is selected from
   i. a parent mannanase enzyme with at least 75% homology to SEQ ID NO:1 or a functional fragment thereof;
   ii. a parent mannanase enzyme derived from *Trichoderma reesei*;
   iii. at least one mannanase enzyme variant;
b) Making at least one alteration which is an insertion, a deletion or a substitution of one or more amino acid residues in the parent mannanase enzyme to obtain a mannanase enzyme variant;
c) Screening for a mannanase enzyme variant which compared to the parent mannanase enzyme has improved characteristics, as herein described, preferably selected from one or more of:
   i. higher thermal stability and/or
   ii. specific activity and/or
   iii. proteolytic stability and/or
   iv. stability at low pH-values; and/or
   v. high specific activity at low pH values;

d) Preparing the mannanase enzyme variant.

Optionally, at least steps a) to c) may be repeated in one or more subsequent (iterative) rounds. Therefore, it is envisaged that the parent mannanase enzyme is a mannanase enzyme variant prepared by previous rounds of the above method a) to c).

In a further embodiment the invention provides a method of preparing a mannanase variant, comprising the following steps:
(a) providing a parent mannanase enzyme, selected from
   (i) a mannanase enzyme with at least 75% homology to SEQ ID NO:1 or a functional fragment thereof;
   (ii) a mannanase enzyme derived from *Trichoderma reesei*;
   (iii) at least one mannanase enzyme variant;
(b) generating a population of mannanase variants by alteration of the parent mannanase, preferably, said alteration(s) is/are obtained through an insertion, deletion or substitution of at least one amino acid residue in the parent mannanase, or any combination thereof;
(c) screening of the population for a mannanase variant which compared to the parent mannanase enzyme has improved characteristics, as herein described, preferably selected from one or more of:
   (i) higher thermal stability and/or
   (ii) specific activity and/or
   (iii) proteolytic stability and/or
   (iv) stability at low pH-values; and/or
   (v) high specific activity at low pH values;
(d) selecting one or more mannanase variants from the population of mannanases;
(e) optionally repeating steps (a) to (c) cyclically, and preferably wherein mannanase variants selected in one cycle are used as first mannanases in the following cycle.

In a further embodiment, the invention provides a method of preparing a mannanase enzyme variant, which method comprises:
(a) providing a parent mannanase enzyme, selected from
   (i) a mannanase enzyme with at least 75% homology to SEQ ID NO:1 or a functional fragment thereof;
   (ii) a mannanase enzyme derived from *Trichoderma reesei*;
   (iii) at least one mannanase enzyme variant;
(b) expressing the mutated nucleic acid molecule obtained in step (a) in a host cell;
(c) screening of the population for a mannanase variant which compared to the parent mannanase enzyme has improved characteristics, as herein described, preferably selected from one or more of:
   (i) higher thermal stability and/or
   (ii) specific activity and/or
   (iii) proteolytic stability and/or
   (iv) stability at low pH-values; and/or
   (v) high specific activity at low pH values;
(d) Preparing the mannanase enzyme variant expressed by the host cell.

Optionally, steps a) to c), optionally including d) may be repeated in one or more subsequent (iterative) rounds.

In a further embodiment, the invention provides a method of preparing a mannanase variant, comprising the following steps:
(a) subjecting a nucleic acid molecule encoding a parent mannanase enzyme to mutagenesis to generate a population of altered nucleotide variants, wherein preferably said alteration(s) is/are obtained through an insertion, deletion or substitution of at least one amino acid residue in the parent mannanase, or any combination thereof, and wherein the parent mannanase enzyme is selected from
(i) a mannanase enzyme with at least 75% homology to SEQ ID NO:1 or a functional fragment thereof;
(ii) a mannanase enzyme derived from *Trichoderma reesei*;
(iii) at least one mannanase enzyme variant;
(b) expressing the population of nucleotide variants obtained in step (a) in a population of corresponding host cells;
(c) screening of the population for a mannanase variant which compared to the parent mannanase enzyme has improved characteristics, as herein described, preferably selected from one or more of:
(i) higher thermal stability and/or
(ii) specific activity and/or
(iii) proteolytic stability and/or
(iv) stability at low pH-values; and/or
(v) high specific activity at low pH values;
(d) selecting one or more mannanase variants from the population of mannanases;
(e) optionally repeating steps (a) to (c) cyclically, and preferably wherein mannanase variants selected in one cycle are used as first mannanases in the following cycle.

Where appropriate, in the above methods of preparing a mannanase enzyme variant, the said nucleic acid molecule is preferably a DNA sequence.

The nucleic acid molecule is preferably an isolated and/or purified nucleic acid molecule or nucleic acid molecule coding for the enzyme comprising the amino acid sequence corresponding to *Trichoderma reesei* mannanase, or a homologue thereof as herein described.

The mannanase parent is preferably selected from SEQ ID NO:1 or a derivative or functional fragment thereof, or a homologue of the *Trichoderma reesei* mannanase as disclosed in SEQ ID NO:1 as described herein.

In the above embodiments of the invention, which relate to methods of preparing mannanase enzyme variant the parent mannanase enzyme/nucleotide encoding the parent mannanase enzyme is preferably a wild type mannanase/wt mannanase encoding nucleotide.

However, in another embodiment the parent enzyme may be a variant prepared by previous rounds of mutagenesis, i.e. in one embodiment, the methods of preparing mannanase enzyme variants are iterative, wherein the steps a) to c) (optionally including step d)) as outlined above are repeated at least more than once. In such embodiments the mutagenesis method used in the first round of mutagenesis is preferably error prone PCR, more preferably error threshold PCR. Subsequent rounds may also be performed by error prone PCR, more preferably error threshold PCR, but may alternatively be performed by recombination based mutagenesis, wherein groups of at least two independent improved variants are identified in a first round of mutagenesis and are, during a second or subsequent round of mutagenesis recombined to give at least one recombinant variant, e.g. using family shuffling or recombinase chain reaction methods.

It will be apparent to the skilled person that alternative mutagenesis methods can also be used, including rational design, site scanning mutagenesis, or chemically/radiation induced mutagenesis.

In the above embodiments of the invention, which relate to methods of preparing a mannanase enzyme variant the mannanase enzyme variant is preferably screened for higher thermal stability.

In the above embodiments of the invention, which relate to methods of preparing a mannanase enzyme variant the mannanase enzyme variant is preferably screened for at least a single parameter, preferably selected from higher thermal stability, higher proteolytic stability, higher stability at low pH and higher specific activity, most preferably higher thermal stability.

Preferably, the screening for said first parameter is performed in at least a first round of mutagenesis comprising at least steps a) to c), wherein c) comprises at least the screening for said first parameter. This first round of mutagenesis can then be followed by further (iterative) rounds of mutagenesis and selection comprising steps a) to c) (optionally including d)) wherein the selection in said further rounds can be for the same selection parameter as used in step c) of the said first round, or alternatively for a different parameter.

During iterative rounds of the above methods of preparing a mannanase enzyme variant, preferably said first parameter is selected from higher thermal stability, higher proteolytic stability, higher stability at low pH and higher specific activity, most preferably higher thermal stability. Preferably, when a first round of mutagenesis has been performed to select variants with a higher thermal stability, during a subsequent (iterative) round(s) of mutagenesis comprising steps a) to c), said parameter is selected from higher thermal stability, higher proteolytic stability, higher stability at low pH and higher specific activity, most preferably higher proteolytic stability and higher specific activity.

In the above embodiments of the invention, which relate to methods of preparing a mannanase enzyme variant, the mannanase enzyme variant is preferably screened for higher thermal stability and higher proteolytic stability and higher specific activity in at least one round of mutagenesis (steps a to c), preferably more than one round, i.e. iterative rounds of selection.

The parent mannanase enzyme is preferably derived from *Trichoderma reesei* RUT-C30.

In methods of preparing a mannanase enzyme variant, which methods comprise subjecting a DNA sequence encoding a parent mannanase enzyme to mutagenesis, the DNA sequence encoding a parent mannanase enzyme is preferably subjected to random mutagenesis, more preferably error prone PCR, even more preferably error threshold PCR.

The preferred method for mutagenesis of a DNA sequence encoding a parent mannanase enzyme is error prone PCR, more preferably error threshold PCR. Other methods of mutagenesis may be used either in place of error prone/threshold PCR or in conjunction with error prone/threshold PCR. These methods are well known to any one skilled in the art.

The term "expression in a host cell" when used in the context of the embodiments which refer to 'a method of preparing a mannanase enzyme variant' is preferably defined as production of the mannanase enzyme variant in a living organism, organ or cell as herein defined. Preferable hosts are *Escherichia coli* K12; *Bacillus subtilis*; *Saccharomyces cerevisiae*.

However, it is considered that for the purpose of selection of the mannanase enzyme variants as herein described, such methods may employ in vitro methods of expression of mannanase enzyme variants, preferably for use in step (c) of said methods, which utilize the transcription and translation machinery isolated from one or more cells isolated from one or more living organism or viruses. Such in vitro production of variant mannanases of the invention can also be used for selecting preferred variant mannanases. In vitro expression can be suitably performed using standard techniques. For reference see 'In vitro Expression Guide' available from Promega Inc (Part# BR053).

Fusion proteins: It is also understood that the amino acid sequence revealed in SEQ ID NO:1 and derivatives thereof described herein for use according to the present invention may be produced as a N- and/or C-terminal fusion protein, for example to aid in extraction, detection and/or purification and/or to add functional properties to the mannanase molecule. The fusion protein partner may be any protein or peptide including any polypeptide sequence derived from the native host, any other naturally occurring amino-acid sequence as well as synthetic sequences. Examples of fusion protein partners include, but are not limited to, glutathione-S-transferase (GST), 6xHis, GAL4 (DNA binding and/or transcriptional activation domains), FLAG-, MYC-tags or other tags well known to anyone skilled in the art. It may also be convenient to include a proteolytic cleavage site between the fusion protein partner and the protein sequence of interest to allow removal of fusion protein sequences. Preferably, the fusion protein will not hinder the activity of the protein sequence of interest.

In a preferred embodiment of the invention the mannanase variants are fused to functional domains including leader peptides, propeptides, binding domains or catalytic domains. Examples for preferred leader sequences that provide the fusion protein with enhanced properties such as higher expression and/or secretion are detailed elsewhere in this application.

Binding domains may include, but are not limited to, carbohydrate-binding domains of various specificities, providing increased affinity to carbohydrate components present during the application of the mannanase. It is also envisioned that the fusion partner domain may comprise enzymatically active domains, such as activities supporting the action of the mannanase in producing the desired product by providing activity on one or more components of the substrate and/or any product of the mannanase catalytic reaction. Non-limiting examples of catalytic domains include: cellulases, hemicellulases such as xylanase, exo-mannanases, glucanases, arabinases, galactosidases, pectinases, and/or other activities such as proteases, lipases, acid phosphatases and/or others or functional fragments thereof.

Linkers: Fusion proteins may optionally be linked to the mannanase through a linker sequence comprised of preferably less than 100 amino acids, more preferably less than 50 amino acids, less than 30 amino acids or less than 20 amino acids. The linker may simply join the mannanase and the fusion domain without significantly affecting the properties of either component, or it may optionally have functional importance for the intended application due to its amino acid composition, structure and/or posttranslational modification occurring during expression in the native host or any suitable heterologous host. The source of the linker sequence may be from an amino acid sequence from any organism or any synthetic peptide sequence.

Additional proteins: The mannanases described herein for use according to the present invention may also be used in conjunction with one or more additional proteins of interest (POIs) or nucleotide sequences of interest (NOIs). Non-limiting examples of POIs include: hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or others. These include enzymes that, for example, modulate the viscosity of the substrate solution/suspension or increase the accessibility and/or solubility of the polymannose substrate. The NOI may even be an antisense sequence for any of those sequences. As described above, the POI may even be a fusion protein. The POI may even be fused to a secretion sequence.

Other sequences can also facilitate secretion or increase the yield of secreted POI. Such sequences could code for chaperone proteins as for example the product of *Aspergillus niger* cyp B gene described in UK patent application 9821198.0.

The NOI coding for POI may be engineered in order to alter their activity for a number of reasons, including but not limited to, alterations which modify the processing and/or expression of the expression product thereof. By way of further example, the NOI may also be modified to optimise expression in a particular host cell. Other sequence changes may be desired in order to introduce restriction enzyme recognition sites.

The NOI coding for the POI may include within it synthetic or modified nucleotides—such as methylphosphonate and phosphorothioate backbones.

The NOI coding for the POI may be modified to increase intracellular stability and half-life. Possible modifications include, but are not limited to, the addition of flanking sequences of the 5' and/or 3' ends of the molecule or the use of phosphorothioate or 2' O-methyl rather than phosphodiester linkages within the backbone of the molecule.

Expression of mannanase genes: In order to produce a mannanase enzyme, the DNA encoding the enzyme can be chemically synthesized from published sequences or obtained directly from host cells harbouring the gene (e.g., by cDNA library screening or PCR amplification). The mannanase gene can be included in an expression cassette and/or cloned into a suitable expression vector by standard molecular cloning techniques. Such expression cassettes or vectors often contain sequences that assist initiation and termination of transcription (e.g., promoters and terminators), and may contain selectable markers. Cassettes can also be comprised of plus or minus strand mRNA, and their expression may or may not include an amplification step before translation of the mRNA. The mannanase gene to be expressed can contain or not contain certain domains of the protein, such as polymer binding domains (e.g., carbohydrate binding domains) of various specificities. The expression cassette or vector can be introduced in a suitable expression host cell which will then express the corresponding mannanase gene. Particularly suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces*, *Staphylococcus* (e.g., *S. carnosus*), *Lactococcus* (e.g., *L. lactis*), lactic acid bacteria or *Bacillus* (*subtilis, megaterium, licheniformis*, etc.). Also particularly suitable are yeast expression hosts such as *Saccharomyces cerevisiae, Schizosaccharomyces pombe, Yarrowia lipolytica, Hansenula polymorpha, Kluyveromyces lactis* or *Pichia pastoris*. Especially suited are fungal expression hosts such as *Aspergillus niger, Chrysosporium lucknowense, Aspergillus* (e.g., *A. oryzae, A. niger, A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines, transgenic mammalian systems such as rabbit, goat or cattle, other eukaryotic hosts such as insect cells or viral expression systems such as bacteriophages like M13, T7 phage or Lambda, or viruses such as Baculovirus expression systems.

Promoters and/or signal sequences associated with any secreted proteins in any particular host are candidates for use in the heterologous production and secretion of mannanase genes in that host or other hosts. As an example, in filamentous fungal systems, the promoters that drive the genes for cellobiohydrolase I (cbh1), glucoamylase A (glaA), TAKA-amylase (amyA), xylanase (exlA), the gpd-promoter cbh1, cbhll, endoglucanase genes EGI-EGV, Cel61B, Cel74A, egl1-egl5, gpd promoter, Pgk1, pki1, EF-1alpha, tef1, "cDNA1" and hex1 are particularly suitable and can be derived from a number of different organisms, for example *A. niger, T. reesei, A. oryzae, A. awamori* and *A. nidulans*. That promoters and signal sequences can be improved by sequence optimization is known in the art and such improved signal sequences are especially suitable (see below). The mannanase gene was also recombinantly associated with a suitable homologous or heterologous signal sequence that leads to secretion of the mannanase enzyme into the extracellular (or periplasmic) space, thereby allowing direct detection of enzyme activity in the cell supernatant (or periplasmic space or lysate). Particularly suitable signal sequences for *Escherichia coli*, other Gram negative bacteria and other organisms known in the art include those that drive expression of the HlyA, DsbA, Pbp, PhoA, PelB, OmpA, OmpT or M13 phage GIll genes. For *Bacillus subtilis*, gram positive organisms and other organisms known in the art, particularly suitable signal sequences further include those that drive expression of the AprE, NprB, Mpr, AmyA, AmyE, Blac, SacB, and for *S. cerevisiae* or other yeast, include the killer toxin, Bar1, Suc2, Mating factor alpha, Inu1A or Ggplp signal sequence. Signal sequences can be cleaved by a number of signal peptidases, thus removing them from the rest of the expressed protein. The rest of the expressed protein can be expressed alone or as a fusion with other peptides, tags or proteins located at the protein's N- or C-terminus (e.g., 6xhis, HA or FLAG tags). Fusions can include tags, peptides or proteins that facilitate affinity purification or detection (e.g., 6xhis, HA, chitin binding protein, thioredoxin or FLAG tags), as well as those that facilitate expression, secretion or processing of the target mannanase. Processing sites can include enterokinase, STE13, Kex2 or other protease cleavage sites for cleavage in vivo or in vitro. Expression-increasing fusions can include part or all of a well expressed and/or a well secreted protein (e.g., fungal cellobiohydrolase, glucoamylase, amylase or xylanase proteins) or artificial peptides that increase protein production/secretion.

Mannanase genes are introduced into expression host cells by a number of transformation methods including, but not limited to, electroporation, lipid-assisted transformation or transfection ("lipofection"), chemically mediated transfection (e.g., CaCl and/or CaP), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the enzyme variants are expressed intracellularly. Optionally, after intracellular expression of the enzyme variants, or secretion into the periplasmic space using signal sequences such as those mentioned above, a permeabilisation or lysis step can be used to release the mannanase enzyme into the supernatant. The disruption of the membrane barrier can be effected by the use of mechanical means such as ultrasonic waves, pressure treatment (French press), cavitation or the use of membrane-digesting enzymes such as lysozyme or enzyme mixtures. As a further alternative, the genes encoding the mannanase enzyme are expressed cell-free by the use of a suitable cell-free expression system. For example, the S30 extract from *Escherichia coli* cells was used for this purpose or commercially available systems (e.g., CECF technology by Roche Applied Science, Inc.). In cell-free systems, the gene of interest was typically transcribed with the assistance of a promoter, but ligation to form a circular expression vector is optional. RNA can also be exogenously added or generated without transcription and translated in cell free systems. Configurations of expression constructs for in vitro expression and execution of all of the above expression systems are well within the ability of the skilled artisan.

The above methods of cloning and expression of the *Trichoderma reesei* mannanase gene are suitable both for industrial scale expression and for use in high throughput screens for the evaluation of mutated variants.

Generating mutated variants of the *Trichoderma reesei* mannanase gene or the alpha mating factor signal sequence: Mutated variants of genes can readily be created using a number of methods that are common within the art. These include, among others, mutagenic polymerase chain reaction (PCR) mutagenesis. The *Trichoderma reesei* mannanase gene was mutated using such methods and the mutagenic library was expressed in *S. cerevisiae* for screening. In order to best distinguish improved from unimproved variants in a high throughput screen, it was found advantageous to further increase the secretion into the culture medium of the *Trichoderma reesei* mannanase from this yeast host. This was accomplished by engineering the alpha mating factor yeast secretion signal peptide (SEQ ID NO:5) by random mutagenesis and screening for increased secreted mannanase activity. By this method, a signal sequence was found that improved secretion from *S. cerevisiae* and thereby improved the ability to screen variant mannanase libraries (see example 2).

Purification: As described above, the mannanase proteins can be expressed in a variety of expression systems and accordingly the appropriate down-stream processing and purification procedures have to be selected. The protein of interest can be secreted into the extracellular or periplasmic space or expressed intracellularly. In a preferred embodiment of the invention the mannanase variant is expressed in a microbial host and the protein is secreted into the periplasmic or extracellular space. Cells expressing the mannanase variants are preserved by methods well known to anyone skilled in the art, such as, but not limited, to cryo stocks. Cultures of the expressing organism are prepared at an appropriate volume with standard methods of fermentation. In a preferred embodiment, cultures for protein expression are inoculated from a cryo stock and the volume of the culture increased successively in the appropriate containers. In a preferred embodiment the cells are grown in a fermenter and optionally growth conditions such as pH, temperature, oxygen and/or nutrient supply are controlled. A first step of purification comprises the separation of cells from supernatant using one or more of several techniques, such as sedimentation, microfiltration, centrifugation, flocculation or other. In a preferred embodiment the method applied is microfiltration. In case of intracellular expression the cells are subjected to treatments that result in a release of the protein from the intracellular space. These treatments may comprise for example pressure, enzymatic, osmotic shock, freezing, ultrasonic or other treatment to produce a cellular extract which may or may not be subjected to further purification.

In a preferred embodiment of the invention the protein is secreted into the supernatant and an optional step of purification comprises the concentration of the supernatant by ultrafiltration. Further protein purification from the supernatant or concentrated supernatant may be performed with one or more of several methods comprising extraction or fractionation methods such as ammonium sulfate or ethanol or acid precipitation, or chromatographic methods including but not limited to ion-exchange, hydrophobic interaction, hydroxylapatite, size fractionation by gel-filtration, phosphocellulose or lectin chromatography and affinity chromatography or any combination thereof. In a more preferred method the affinity-tagged protein is purified by metal-chelate affinity chromatography to obtain a high purity protein. The preferred purification method yields a purity of the protein of >30%, in a more preferred method the purity is >50%, >60%, >70%, or >80%. In an even more preferred method the purity is >90%, in a yet more preferred method the purity is >95% and in a most preferred method the purity is >98%.

In another preferred embodiment of the invention the supernatant or the supernatant partially purified by ultrafiltration or the concentrated and/or diafiltrated supernatant is dried by any one of several technical methods such as, but not limited to, spray-drying, lyophilisation, down-draught evaporation, thin-layer evaporation, centrifugal evaporation, conveyer drying or any combination thereof.

In a further preferred embodiment of the invention the fermented cell-suspension including the expressed mannanase variants is dried as a whole using processes such as, but not limited to, fluidised bed drying, conveyer drying, spray drying or drum drying or any combination thereof.

Formulations: In general, compositions of the mannanase or any derivative described herein can be either liquid or dry. Liquid compositions may comprise the mannanase alone or in combination with other proteins or enzymes and may contain additives that support the stability and/or activity of the mannanase or other proteins or enzymes in the composition. These include but are not limited to glycerol, sorbitol, propylene glycol, salts, sugars, preservatives, pH-buffers and carbohydrates. Typically, the liquid composition is an aqueous or oil-based slurry, suspension or solution.

Dry compositions may be generated from any liquid composition including the fermentation supernatant or cell suspension or cell extract by spray-drying, lyophilisation, down-draught evaporation, thin-layer evaporation, centrifugal evaporation, conveyer drying or any combination thereof. The dry compositions may be granulates of the appropriate size to be compatible with the further downstream applications such as food or feed processing or to qualify as a component for foods or animal feed.

Before drying a bulking agent may be added to the liquid composition which, after drying, effectively enhances the properties of the dry composition such as providing a higher heat stability due to protection of the enzyme from environmental factors by the bulking reagent, better technical handling properties and others.

Once a dry preparation is obtained, agglomeration granulates may be prepared using agglomeration techniques, e.g. in a shear mixer during which a filler material and the enzyme are co-agglomerated to form granules. Absorption granulates are prepared by having cores of a carrier material to absorb or be coated with the enzyme. Typical filler materials include disodium sulphate, kaolin, talc, magnesium aluminium silicate and cellulose fibres. Optionally, binders such as dextrins are also included in agglomeration granulates. Typical carrier materials include starch, e.g. in form of cassaya, corn, potato, rice and wheat, or salts may be used.

Optionally granulates are coated with a coating mixture. Such a mixture comprises coating agents, preferably hydrophobic coating agents, such as hydrogenated palm oil and beef tallow, and, if desired, other additives such as calcium carbonate and kaolin.

In a particularly preferred embodiment the compositions comprising the mannanases of the invention are intended for applications in food and feed processing or as supplement to food and feed. In this case, mannanase compositions may additionally contain other substituents such as colouring agents, aroma compounds, stabilizers, vitamins, minerals, other feed or food enhancing enzymes and the like. This applies in particular to the so-called pre-mixes. Food additives according to this present invention may be combined with other food components to produce processed food products. Such other food components include one or more other, preferably thermostable, enzyme supplements, vitamin food additives and mineral food additives. The resulting, combined food additive, including possibly several different types of compounds can than be mixed in an appropriate amount with the other food components such as cereal or plant proteins to form a processed food product. Processing of these components into a food product can be performed using any of the currently available methods.

In a preferred embodiment of the invention the mannanase composition additionally comprises an effective amount of one or more feed or food enhancing enzymes, in particular selected from the group consisting of, but not limited to, hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or others.

Formulations of the mannanases of the invention are preferably used for processing and/or manufacturing of food or animal feed.

Technical applications: Envisioned is the use of the mannanase derivatives as food additives or digestive aids which promote the degradation of oligomannose containing food material, thus releasing potentially beneficial oligomannoses or derivatives thereof.

Another application in the field of food and feed processing is the production of manno-oligosaccharides as important prebiotics from PKE for feed and food. By the treatment of PKE or other galactomannan containing components with mannanase manno-oligosaccharides and D-mannose are produced. Manno-oligosaccharides are used as prebiotic components for feed and food: Manno-oligosaccharides promote the growth of probiotics (e.g. *Bifidobacteria* and *Lactobacillus* sp), inhibit the growth of enterobacteria *Salmonella*, neutralise the antinutritional properties of lectins and find applications in the pharmaceutical industry. Furthermore manno-oligosaccharides and especially mannose are suspected to be immune stimulating components in feed stuff.

Yet another application in the field of food and feed processing is the cleavage of mannan containing components in the cell wall of fruits for juice recovery improvement, e.g. by adding the said enzymes to pineapples, lemons, oranges, limes, grapefruits, prior to the squeezing procedure.

Another application in the field of food and feed processing is the use of the mannanase according to the present invention for yield improvement in palm kernel oil extraction. The oil content remaining in the palm kernel expeller is between 5-12% after pressing. This remainder can be further reduced by chemical extraction to about 3%. By application of a mannanase according to the invention, the release of the fat could be rapidly increased, thus providing an improved process (see example 18). Additionally the resulting palm kernel expeller would be of higher quality due to the reduced content of galactomannan fibres which are known to be antinutritive components in feed.

Yet another application in the field of food and feed processing is the delivery of D-mannose from PKE or other galactomannan containing components. Palm kernel meal contains about 20% mannose bound as galactomannan fibers. The treatment of PKE, copra or other galactomannan containing raw substances with mannanases causes the release of D-mannose (see examples). Mannose and its derivatives are ingredients used in food (e.g. low calorie dietetic food products), pharmaceuticals (mannose cures more than 90% of all urinary tract infections), cosmetics, textiles and in the manufacturing of polymers. Because of limited supply mannose is very expensive at present compared to other more common hexose sugars and its supply is scarce. D-mannose can also be used as a raw material for the production of mannitol. Mannitol itself is derived from Mannose via reduction with much higher yield and less by-products than from the conversion of fructose. Mannitol is a polyol widely used in food and pharmaceutical industries because of its unique functional properties: Mannitol is used as sweetener, for pharmaceutical formulations (chewable tablets and granulated powders), in the production of chewing-gum, as bodying, texturing and anti-caking agent for food, as osmoactive pharmaceutical and diabetic food component.

Furthermore, in the above context of food and feed processing the use of a mannanase according to the invention for the partial hydrolysis of galactomannans by incubation of guar gum or locust bean gum is provided. The resulting hydrolysates are used in food and brewery industry as texturing components and for pharmaceutical applications.

Production of sugars: The described mannanase enzymes in the present invention are in particular useful for the production of sugars or oligosaccharides from polymannose containing plant material such as palm kernel, coconut, konjac, locust bean gum, gum guar and soy beans. Preferred is plant material like palm kernel meal, palm kernel expellers, copra meal, copra pellets and soy bean hulls.

In a particular preferred embodiment the mannanase enzymes according to the present invention are applied for the production of mannose and mannopolymers such as mannobiose, mannotriose, mannotetraose, mannopentaose, mannohexaose, mannoheptaose, mannooctaose, mannononaose and higher polymers of mannose and/or derivatives thereof. Also preferred are galactosyl mannooligosaccharides thereof with different ratios between galactose and mannose ranging from 1 to 0.05.

In a further preferred embodiment of the present invention the sugars are composed of mannose and glucose and are referred to as glucomannans. These polyols might be composed of 2, 3, 4, 5, 6, 7, 8, 9 or more monomers of mannose and/or glucose with a mannose content of 1/15, 1/14, 1/13, 1/12, 1/11, 1/10, 1/9, 1/8, 1/7, 1/6, 1/5, 1/4, 1/3, 1/2, 1, 2/3, 3/4, 3/5, 4/5, 5/6, 2/7, 3/7, 4/7, 5/7, 6/7, 3/8, 5/8, 7/8, 2/9, 4/9, 3/10, 2/11, 4/11, 3/12, 2/13 or 1/14. Also particularly preferred are galactosyl glucomannooligosaccharides thereof with different ratios between galactose and mannose ranging from 1 to 0.05.

In a further preferred embodiment of the present invention the mannanase is used in combination with other carbohydrases like glucanase, and/or xylanase, and/or alpha-galactosidase and/or cellulase for the hydrolysis of the plant material in order to generate the sugars.

In a more preferred embodiment of the present invention the hydrolysis of the polymannose containing plant material leads to sugars exhibiting a prebiotic functionality. These sugars are generated to promote the growth of probiotics, bacteria that are known to support a healthy immune system. Examples of such bacteria are bifidobacteria. Known bifidoabteria are B. adolescensis, B. angulatum, B. animalis, B. asteroides, B. bifidum, B. bifidum, B. boum, B. breve, B. catenulatum, B. choerinum, B. coryneforme, B. cuniculi, B. dentium, B. gallicum, B. gallinarum, B. indicum, B. infantis, B. longum, B. magnum, B. merycicum, B. minimum, B. pseudocatenulatum, B. pseudolongum, B. pullorum, B. ruminantium, B. saeculare, B. scardovii, B. subtile, B. thermacidophilum and B. thermophilum.

Coffee extraction: The described mannanase enzymes according to the present invention are useful for the hydrolysis of galactomannan which is present in liquid coffee extracts. In a preferred embodiment of the invention the mannanase is used to inhibit the formation of gels as they occur during freeze drying of liquid coffee extracts. The decreased viscosity of the extract reduces the energy consumption during drying. In an even more preferred embodiment of the invention the mannanase enzymes are applied in an immobilized form which reduces the consumption of enzyme and prevents contamination of the coffee extract.

In this context, another interesting application is the use of mannanase enzymes according to the present invention for the production of mannose or manno-oligosaccharides from coffee waste, in order to receive higher value products. As described before mannanase releases mannose or oligosaccharides from coffee waste which are high value functional feed and food components. In the coffee beverage industry, spent coffee grounds are generally used as fuel or treated as an industrial waste). Roasted coffee contains 1.8-4.4% mannan. Therefore spent coffee grounds contain a large amount of β-mannan, which can be converted into mannooligosaccharides by enzymatic hydrolysis. Mannooligosaccharides obtained from coffee mannan are said to reduce serum lipid levels in humans (Jpn J food eng 6 (2005).

Animal feed: Several antinutritional factors limit the use of specific plant material in the preparation of animal feed and food for humans. Plant material containing oligomannans like mannan, galactomannan, glucomannan and galactoglucomannan is described to reduce the digestibility and absorption of nutritional compounds like minerals, vitamins, sugars and fats by the animals. The negative effects are in particular due to the high viscosity of the mannopolymers and to the ability of the mannopolymers to adsorb nutritional compounds. These effects can be eliminated/reduced through the use of mannopolymer degrading enzymes, namely mannanase enzymes which then allows a much higher proportion of mannopolymer containing cheap plant material in the feed and thereby a reduction of costs. Additionally, through the activity of the mannanase enzymes mannopolymers are broken down to monosaccharides which can be readily assimilated and provide additional energy.

In order to use an enzyme as an effective feed supplement for e.g. monogastric animals like poultry or swine it has to be stable in the stomach. This means it has to be stable at low pH (approx. pH 2-3) and additionally it has to be resistant against pepsin at this low pH. Furthermore such enzymes need to be active at low pH (approx. pH 3.0) to be effective in the stomach. The mannanase enzymes provided in the present invention fulfil all these criteria unlike other mannanase enzymes as for example the wild-type mannanase from Trichoderma reesei which is not stable at low pH, in particular not stable against pepsin at low pH. Therefore the mannanase enzymes provided in the present invention are especially well suited for feed applications in which the enzyme has to be active in the animal.

The mannanase enzymes according to the present invention are useful as additives to feed for monogastric animals such as poultry and swine, as well as for human food. The feed may however also be provided to ducks, geese, as well as bovine, canine, caprine, equine feline, as well as crustaceans and fish. The mannanase enzymes can also be used to pretreat the feed instead of adding it to the feed.

In a preferred embodiment of the invention the mannanase enzymes are added to feed for weanling pigs, nursery pigs, piglets, fattening pigs, growing pigs, finishing pigs, laying hens, broiler chicks, turkey.

In a further preferred embodiment of the invention the mannanase enzymes are additives to feed composed of plant material like palm kernel, coconut, konjac, locust bean gum, gum guar, soy beans, barley, oats, flax, wheat, corn, linseed, citrus pulp, cottonseed, groundnut, rapeseed, sunflower, peas, lupines and vitamins as well as minerals. In an even more preferred embodiment of the invention the mannanase enzymes are additives to feed partially composed of palm kernel meal, palm kernel expellers, copra meal, copra pellets and/or soy bean hulls.

In a further preferable embodiment of the invention the mannanase enzymes are used in combination with other enzymes selected from the group consisting of, but not limited to, phytases, alpha-galactosidases, beta-galactosidases, pectinases, xylanases, arabinoxylanases, proteases, beta-glucanases, cellulases, galactanases, endoglucanases, xylosidases, cutinases, lipases and/or phospholipases for the preparation of feed. The mannanase enzymes with or without additional enzymes can also be used in combination with minerals, vitamins and other typical feed supplements.

Since the mannanase enzymes according to the present invention are thermostable enzymes they can be subjected to heat without losing significant activity. Therefore the mannanase enzymes can be used in processes of producing pelleted feed in which heat is applied to the feed mixture before the pelleting step, as it is the case in most commercial pellet mills. The mannanase enzyme can be added to the other feed ingredients in advance to the pelleting step or after the pelleting step to the already formed feed pellets. Within the scope of the present invention the addition prior to the pelleting process is preferred.

In a further preferable embodiment of the present invention the mannanase enzymes are used in animal feed that is especially fed to animals under circumstances where no antibiotics are desired.

In an even more preferred embodiment the mannanase enzymes are used in animal feed partially composed of palm kernel meal, palm kernel expellers, copra meal, copra pellets and/or soy bean hulls. In a most preferred embodiment the mannanase enzymes are used in animal feed for broiler chicks that is partially composed of palm kernel meal, palm kernel expellers, copra meal, copra pellets and/or soy bean hulls.

Paper Pulp Industry: The mannanase enzymes according to the present invention are useful in the enzyme aided bleaching of paper pulps like chemical pulps, semi-chemical pulp, kraft pulps, mechanical pulps or pulps prepared by the sulfite method. The pulps might also be totally chlorine free pulps bleached with oxygen, ozone, peroxide or peroxyacids.

In a preferred embodiment of the present invention the mannanase enzymes are used for the enzyme aided bleaching of pulps produced by modified or continuous pulping methods that exhibit a low lignin contents.

In a further preferred embodiment of the present invention the mannanase enzymes in such applications can either be applied alone or preferably in combination with xylanase and/or endoglucanase and/or alpha-galactosidase and/or cellobiohydrolase enzymes.

Bleaching and/or Desizing agent in textile industry: The mannanase enzymes according to the present invention are as well useful for bleaching of non-cotton cellulosic fibers, yarn or fabric comprising flax, jute, ramie or linen by incubation of the fiber, yarn or fabric with a mannanase according to the present invention for a given time and under conditions suitable to produce a whitening of the fiber, yarn or fabric. The degradation of hemicellulose improves the bleaching process of the fabric.

In textile printing using a printing paste containing a dye and a biological polymer (e.g. guar gum) as thickener, removal of the thickener and excess dye is made much more efficient by washing the printed textile in the presence of mannanase. The enzymatic breakdown of thickener decreases process time as well as the amount of energy and water needed to achieve a satisfactory quality of the textile.

The mannanase enzymes according to the present invention are useful in desizing of fabrics made from e.g. synthetic fibers where often galactomannans like guar gum or locust bean gum are used as sizing agents.

Oil and gas well stimulation by hydraulic fracturing: The mannanase enzymes according to the present invention are useful in a method of hydraulic fracturing used in oil or gas well stimulation. Here the mannanase enzymes act as liquefying agents in a hydraulic fluid that is based on or composed of a mannopolymer and usually contains sand.

As the mannanase enzymes according to the present invention are thermostable enzymes they are preferably used in hydraulic fracturing applications that are performed at high temperatures.

In another preferred embodiment of the invention the liquefying activity of the mannanase enzymes in a hydraulic fracturing application is controlled (inhibited or promoted) by environmental conditions like pH and temperature.

Detergents: The mannanase enzymes according to the present invention can be used in detergent compositions in order to facilitate the removal of mannopolymer containing stains/soils. In a preferred embodiment of the present invention the mannanase enzymes are used in detergent compositions in combination with other enzymes from the group of amylases, cellulases, lipases, pectinases, protease and endoglucanases.

Removal of biofilms: The mannanase enzymes described in the present invention are useful for the removal of mannopolymer containing biofilms. Preferably, for such an application the mannanase enzymes are used in combination with detergents and/or other enzymes from the group of alpha-galactosidases, pectinases, xylanases, arabinoxylanases, proteases, beta-glucanases, cellulases, galactanases, endoglucanases, xylosidases, cutinases and lipases.

Delivery systems: The mannanase enzymes according to the present invention can be used for the targeted and/or time-dependent delivery of matter. This is achieved through the use of systems that are based on gels of mannopolymers that contain and transport the matter. The function of the mannanase enzyme in such a system is the controlled release of the matter by partial or complete degradation of the gel, due to a specific change in the environment of the gel, e.g. the pH and/or the temperature that activates the mannanase enzymes.

In a more preferred embodiment of the present invention the mannanase enzymes are used for the targeted delivery of a drug in a pharmaceutical application.

Processing of Renewable Resources:

Renewable resources, i.e. biomass substrates which are grown and harvested, like crops, straw, wood and wood products, are receiving more and more attention as they are suitable substrates for the production of biological fuels, i.e. solid, liquid, or gas fuel like Biodiesel, Biogas, Vegetable oil, Bioethanol, Biobutanol, BioHydrogen, Bio-Dimethyl ether, Biomethanol, BTL ("Biomass to liquid")-Fuel, GTL ("Gas to liquid")-Fuel, and the like. In $1^{st}$ generation biological fuels, the said plants have been converted using established methods from the food industry, i.e. they were squeezed in order to obtain vegetable oil or starch containing grain was converted to sugar and subsequently fermented with yeast in order to obtain Bioethanol. This means that the energy reservoirs (i.e. fat and/or starch) of the said plants were utilized exclusively. This led to poor energy yields, or poor production quantities of biofuel per acre. In $2^{nd}$ generation biological fuels, not only the energy reservoirs of the said plants are being used, but the approach tends to utilize the complete biomass of the plant. In this context, a mannanase according to the invention can be used to convert plant biomass containing hemicellulose into sugars, which can be metabolized by specific yeast (e.g. *Saccharomyces* sp.) or bacterial strains and other microorganisms in order to produce fermentation products. These fermentation products can be fuels like Bioethanol, Biobutanol but can also be building block molecules like 3-Hydroxy propionic acid, aspartic acid, xylitol and gluconic acid. For more building block molecules that can be derived from sugars see (Werpy and Petersen (2004) Top Value Added Chemicals from Biomass: Volume 1—Results of Screening for Potential Candidates from Sugars and Synthesis Gas. National Renewable Energy Laboratory Report NREL/TP-510-35523, FIG. 3 and Table 8).

Other potential uses comprise the catalytic processing of products which have been obtained from renewable resources with help of mannanases according to the invention. This comprises the processing of glucose and/or fructose, both obtained with help of a mannanse according to the invention, into 2,5-dimethylfuran, a heterocyclic compound which is supposed to have much better fuel properties than bioethanol, as it has a 40% greater energy density, is chemically stable and insoluble in water.

The said approaches draws large benefits from the improved properties of the mannanases according to the invention, particularly of the enhanced heat stability. This means that the respective biomass to sugar conversion can take place under high temperature conditions, which accelerates the respective processes and thus renders them economically more efficient.

In recent experiments of the inventors, palm-kernel expeller (PKE) substrates were used to feed yeast (*Saccharomyces cerevisiae*). The said substrates contain about 37% galactomannan. It turned out that PKE treated with two mannanases according to the invention (i.e., variant B, variant C and/or variant 31) lead to the release of a large amount of sugars, and thus resulted in an improved yeast growth in comparison to untreated PKE. This is a clear hint towards the above postulation, i.e. that the mannanases according to the invention may be a useful tool to enhance the yield in e.g. Bioethanol production out of renewable resources (see example 19).

All the said uses of a mannanase according to the invention have in common that these approaches draw substantial benefit from the improved properties of the mannanase according to the invention, particularly in terms of enhanced thermostability and enhanced resistance against low pH values and protease enzymes.

This is mainly due to the fact that most of the said uses take place in environments with unfavourable conditions, like in mammalian digestive tracts, where low pH values predominate, or at elevated temperatures which are be applied to speed up, facilitate and economically optimise hydrolysis processes like the conversion of renewable resources to sugars as described above.

The present invention is further described by the following Figures and Examples, which are, however, not to be construed as limiting the invention.

DETAILED DESCRIPTION OF THE FIGURES

FIG. 1: Thermostability of *Trichoderma reesei* mannanase and the 53R variant. The wild-type mannanase according to SEQ ID NO:1 and the S3R variant were compared with respect to their thermostability in the production of mannose from palm-kernel expeller substrate (A) and from galactomannan carob at different temperatures (B). It is demonstrated that within experimental error the two mannanases behave similarly and therefore the S3R mutation is concluded to have no effect on the properties which are subject to improvement for the enzyme variants revealed in this application.

FIG. 2: Thermostability of wild-type and variant mannanases in buffer. Samples of the different variants were incubated at the indicated temperatures for 45 min and the residual activity measured with AZCL-galactomannan normalised to activity at 25° C. The temperature where the residual activity equals 50% may be called IT50 and is summarized in Table 3. Variant C has an IT50 increased by 8° C. compared to wild-type mannanase.

FIG. 3: Activity of variants at different temperatures on galactomannan. Overall mannose yields after incubation of different mannanase variants with galactomannan substrate for 16 h at various temperatures were normalised to the mannose yield at 63° C. The decrease of mannose yield with temperature is basically due to thermal decay of the enzyme as demonstrated in FIG. 1. However, the relative mannose yields over temperature reflect a composite of thermostability and temperature optimum. This composite, however, is a relevant parameter for a technical process and demonstrates the superiority of the variants of the invention.

Figure 4:
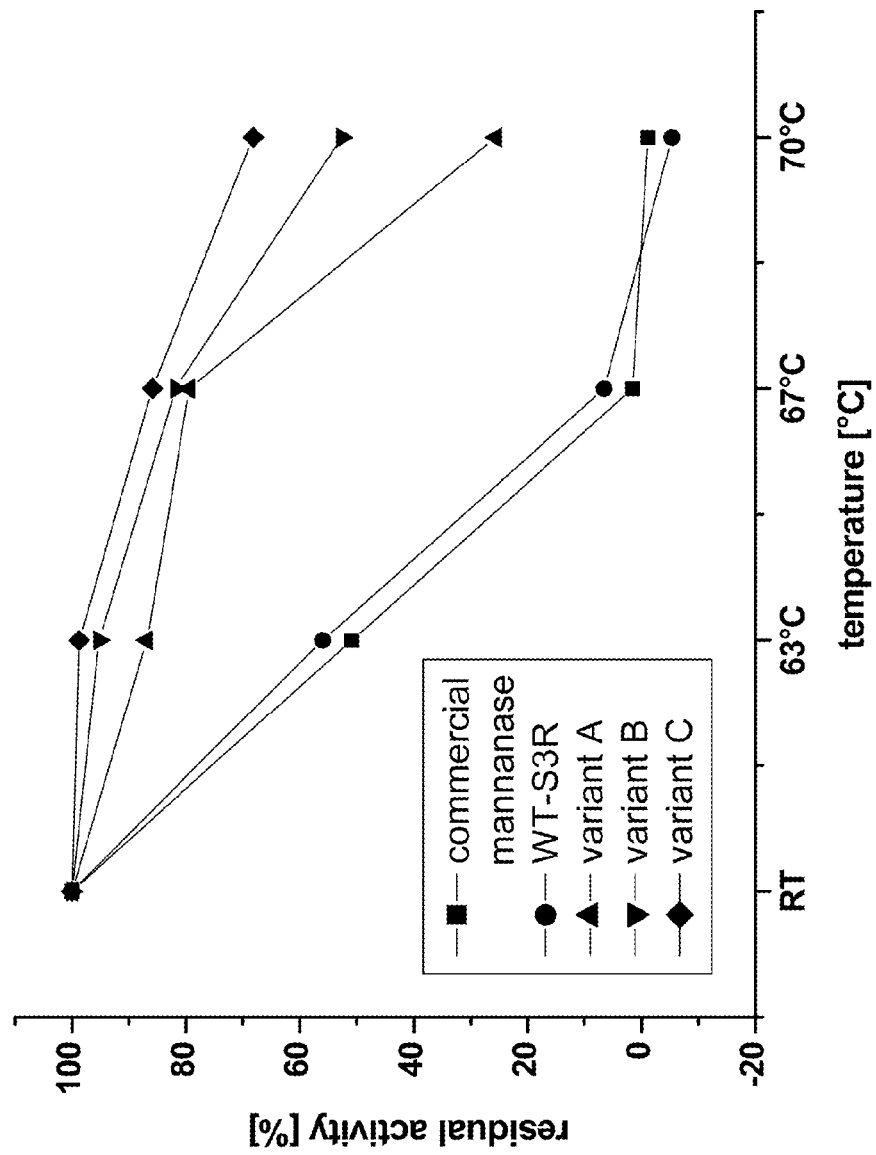
FIG. 4: Thermostability of wild-type mannanase and variants expressed as residual activity after incubation with Palm Kernel Expeller (PKE) substrate at different temperatures for 71 h.

FIG. 4: Thermostability of wild-type mannanase and variants. Different mannanases were evaluated for activity and residual activity on palm-kernel expeller substrate at different temperatures. The residual activity was measured after 71 h incubation at the indicated temperatures with AZCL-galactomannan. It is clearly seen that the residual activity of the commercial and the wild-type mannanase has decreased to 50% and basically 0% at 63° C. and 67° C., respectively, while the best mannanase variant shows >70% residual activity even at 70° C. This clearly demonstrates the increased thermostability of the variants.

FIG. 5: Mannose yields on PKE substrate. Palm kernel expeller has been incubated with different variants at different temperatures and times. The same amount of mannanase was used for each variant. It can clearly be seen that the total amount of mannose generated is highest for variant B which does not have the highest thermostability but a favourable combination of higher specific activity and increased thermostability. While for the wild-type the yield of mannose is drastically decreased with temperature it stays constant for variant B and is even slightly increased for variant C. This demonstrates the higher mannose yield and thermal stability of the variants on a technically relevant substrate.

FIG. 6: Mannose yields with different concentrations of variant B. The higher thermostability of the variant mannanase allows the process to run with lower amounts of enzyme, keeping the mannose yield constant. Similar mannose yields can be obtained with approximately 50% of variant B compared to wild-type, based on protein mass.

Figure 7:
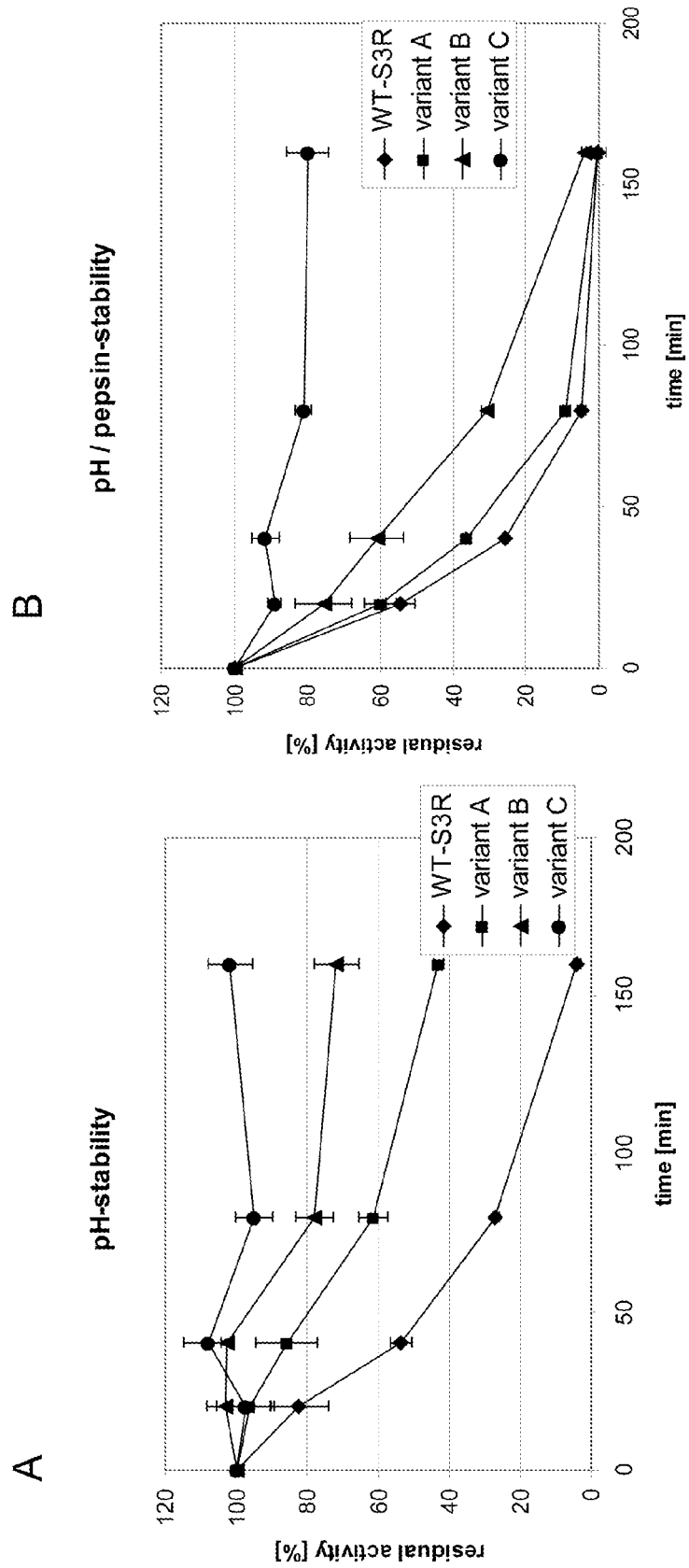
FIG. 7: Stability of different mannanase variants against incubation at pH2.3 and pepsin at pH2.3.

FIG. 7: Pepsin and pH-stability. The stability of different mannanase variants against incubation at pH 2.3 and pepsin at pH 2.3 was investigated. Residual activity is given as a function of incubation time. Clearly, the variants show an increased stability against low pH conditions. Variant C remains 100% active after 3 h incubation at pH 2.3 while the wild-type is basically inactive. A similar trend is seen for the proteolytic stability against pepsin. Again, variant C looses only 20% of its activity while all others are more susceptible to proteolytic degradation and pH-induced inactivation.

FIG. 8: pH activity profile. With the methods given in Example 15 the activity of variants B and C is determined at a range of pH values from pH 2 to pH 5.5. The variants show high activity at low pH conditions conferring high activity in the upper gastrointestinal tract of animals when used as a feed additive.

FIG. 9: Comparison of the release of mannose from guar gum, locust bean gum, and konjac glucomannan, all treated with a mannanase according to the invention (see Example 20).

EXAMPLES

In the following examples, materials and methods of the present invention are provided including the determination of catalytic properties of enzymes obtained by the method. It should be understood that these examples are for illustrative purpose only and are not to be construed as limiting this invention in any manner. All publications, patents, and patent applications cited herein are hereby incorporated by reference in their entirety for all purposes.

Example 1

Cloning of the *Trichoderma reesei* Mannanase Gene

Chromosomal DNA was isolated from *Trichoderma reesei* strain RutC30 after growth on YPD agar plates (20 g Peptone, 10 g Yeast Extract brought to 1 l with water, stirred, 20 g Agar; $1/10^{th}$ volume of 20% dextrose was added after autoclaving). About 10 mg of biomass was scraped from the plate, combined with 0.2 ml glass beads (0.5 mm diameter) and 500 µl of a 24:24:1 mixture of phenol:chloroform:isoamyl alcohol and vortexed 2-5 min, followed by centrifugation at 10000-15000×g. The supernatant was transferred to a new tube and ethanol precipitated. The pellet was resuspended in 20 µl water. The resulting DNA (2 microlitres) was used as template in a PCR reaction using Taq DNA polymerase and containing forward (SEQ ID NO:3) and reverse (SEQ ID NO:4) primers employing the following cycling parameters: 94° C., 2 min followed by 25 cycles of 94° C. 1 min, 50° C. 1 min and 72° C. 2 min followed by 5 min at 72° C. The resulting product was purified using the Qiagen MinElute kit, cut with restriction endonucleases Hind III and EcoRI, ligated into vector PUC19. Introns were removed by overlap extension PCR and the intron free gene was amplified with primers that add an XbaI site at the beginning of the open reading frame (SEQ ID NO:8; SEQ ID NO:9). The addition of the XbaI site changed the third amino acid of the mature protein from serine to arginine, which had no noticeable effect on protein phenotypic properties. The *S. cerevisiae* alpha mating factor signal sequence was fused with the first three codons of the modified mannanase gene using tailed primers by PCR amplification and ligated into vector pYES2 using HinDIII and XbaI. The ccdB cassette from vector pZErO-1 (Invitrogen) was then PCR amplified and cloned using XbaI and XhoI sites as a stuffer fragment into the resulting vector. This stuffer was replaced with the Mannanase gene or variant libraries of the mannanase gene using XbaI and XhoI to yield the final expression construct. The DNA sequence of the intron-free mannanase gene was confirmed using a commercial kit (GenomeLab DTCS Quick Start Kit, Beckman Coulter) and the CEQ 2000XL DNA Analysis System (Beckman Coulter).

Example 2

Generation of an Alpha Mating Factor Signal Sequence that Increases the Secretion of *Trichoderma reesei* Mannanase The alpha mating factor signal peptide DNA sequence (SEQ ID NO:5) from vector pPICZalphaA (Invitrogen) was amplified and mutated using a commercially available kit (GeneMorph® II Random Mutagenesis kit, Stratagene, Inc.). The resulting library of mutated signal sequences was cloned into vector pYES2 harbouring the *Trichoderma reesei* mannanase gene by standard cloning procedures and was transformed into E colas follows: XL1-blue was made competent for electroporation as follows. An isolated colony from a fresh plate was inoculated into 12 ml SOB medium (100 g Bactotryptone, 25 g yeast extract, 2.9 g NaCl, 0.9 g KCl, brought to 5 l with water) lacking antibiotics and shaken at 150 rpm over night at 37° C. A 2.5 ml volume of the culture was then transferred to each of four 1 l unfluted Erlenmeyer flasks containing 250 ml of SOB and cultured as above to an optical density at 600 nm of 0.6, followed by 15 min on ice. The following steps were carried out at 4 degrees centigrade. The bacterial cultures were separately centrifuged 10 min at 2800×g and the supernatant discarded. Bacterial pellets were resuspended in 250 ml 10% glycerol each, re-centrifuged as above and the supernatants discarded. Two pellets were resuspended in 250 ml 10% glycerol. The other two were treated identically. Both suspensions were re-centrifuged as above and the supernatants discarded. The cell pellets were suspended in their interstitial liquid and the volume was brought to 4.5-5.5 ml with 10% glycerol, aliquoted at 50 µl in cryovials and flash frozen in liquid nitrogen and stored at −80° C. For electroporations an aliquot of competent cells were thawed on ice, mixed with 1 µg DNA and transformed in a 2 mm gap cuvette at 2.5 kV. Immediately after electroporation, transformants were supplemented with 1 ml LB liquid medium and incubated for 1 h at 37° C. 10 µl of the culture were diluted in LB and tested for transformation efficiency by plating to solid LB agar containing 20 µg/ml neomycin. The remaining transformed culture was used to inoculate 100 ml liquid LB medium containing 20 µg/ml neomycin ("selective liquid medium"). After overnight cultivation, plasmid DNA was prepared by the Qiaprep Spin DNA Isolation Kit (Qiagen) and 1 µg of DNA used to transform *Saccharomyces* host strain BY4741 by the lithium acetate method (see example 5). This alpha mating factor variant library was then plated to SC-galactose plates [8.4 g Yeast Nitrogen Base (Becton-Dickinson); 1 g Complete Supplement Mixture—uracil (Bio101), brought to 1 l with water, stirred and warmed to 50° C. until dissolved, adjusted to pH 5.6 with 1 N NaOH; 1/8th volume of 40% galactose was added after autoclaving; for SC-galactose plates, 20 g agar was added before autoclaving for each 1 of final medium] containing 0.2% AZCL-galactomannan (Megazyme, Inc). Yeast colonies secreting increased amounts of the *Trichoderma reesei* mannanase were visible as having larger zones of solubilisation of the AZCL-galactomannan substrate. This screening resulted in specific candidates improved in mannanase secretion level. The best specific candidate colony was streaked to result in single colonies on SC-glucose solid medium [8.4 g Yeast Nitrogen Base (Becton-Dickinson); 1 g Complete Supplement Mixture—uracil (Bio101), brought to 1 l with water, stirred and warmed to 50 degrees centigrade until dissolved, adjusted to pH 5.6 with 1 N NaOH; ⅕th volume of 20% glucose was added after autoclaving; for SC-glucose plates, 20 g agar was added before autoclaving for each litre of final medium]. Plasmid DNA was prepared by Zymoprep kit (Zymo Research), transformed into *E. coli* and isolated by Qiaprep Spin DNA Isolation Kit (Qiagen). DNA sequencing reactions were generated using a commercial kit (GenomeLab DTCS Quick Start Kit, Beckman Coulter) and the improved signal sequence determined using the CEQ 2000XL DNA Analysis System (Beckman Coulter). The DNA sequence of the candidate improved signal sequence was determined by this method. The resulting DNA sequence of the improved alpha mating factor signal peptide (SEQ ID NO:6), through application of the standard genetic code for nuclear genes (see "The Genetic Code" in New England Biolabs Catalog and Technical Reference, 2003-2003), unambiguously determined the amino acid sequence of the encoded improved alpha mating factor signal peptide protein sequence (SEQ ID NO:7). This improved signal sequence was found to differ from the wild type alpha mating factor signal sequence by the following mutations: T25I, I66M, I70T, G79V. Removal of the mannanase gene from this construct resulted in a new cloning vector designated pYES21.3_19.

Example 3

Screening for and Selection of Mannanase Variants with Enhanced Thermostability

In order to identify enzyme variants having an improved thermostability, a screening approach based on a confocal fluorescence spectroscopy set-up as disclosed in WO 94/16313 was used. A cell suspension of a *Saccharomyces cerevisiae* library transformed with plasmids coding for the mannanase variants in culture medium was dispensed at a cfu-concentration ensuring that single cells were dispensed in each well of the microtiter plate. Cultures were grown 48 h at 30° C. and protein was secreted into the supernatant. Two volumes of a galactomannan suspension (0.1% galactomannan-carob, Megazyme, in 50 mM sodium acetate, pH 5.0) was added to one volume of culture and incubated at elevated temperatures >60° C. for 16 h. Mannose content was evaluated by adding one volume of assay containing all components for the enzymatic detection (Kit from Megazyme), incubation at room temperature for 1 hour and subjecting the samples to measurement by confocal fluorescence spectroscopy.

Variants with improved temperature stability yielded a higher fluorescent signal and were selected for the generation of further libraries. This cyclic process was repeated until the desired temperature stability was reached. In each successive round the incubation temperature was increased in order to increase the selective advantage of improved variants.

Example 4

Acquisition of Specific Mannanase Genes and Determination of DNA and Protein Sequence after Library Screening The screening of a library that contained a diverse population of candidate mannanase enzymes, each individually harboured on the expression plasmid, pYES21.3_19, resulted in specific candidates improved in the examined characteristics (e.g., thermostability, expression level, etc.). Since the individual members of the library were tested as individual cultures, the result of the screening process was the identification of specific cultures that express putatively improved mannanase genes. The best candidate culture was plated to result in single colonies on solid SC-glucose plates. A resulting isolated colony was inoculated into liquid SC-glucose medium, and plasmid DNA was prepared by Zymoprep kit (Zymo Research). The resulting plasmid DNA was transformed into *E. coli* strain XL1-blue using standard methods, amplified by cell growth in Luria-Bertani solid and liquid medium supplemented with 50 µg/ml ampicillin and isolated by a Qiagen kit. DNA sequencing reactions were generated using the resulting plasmid DNA with a commercial kit (GenomeLab DTCS Quick Start Kit, Beckman Coulter) and the improved mannanase gene sequence determined using the CEQ 2000XL DNA Analysis System (Beckman Coulter). The DNA sequence of a candidate improved mannanase gene was unambiguously determined by this method, and the resulting DNA sequence of the mannanase gene, through application of the standard genetic code for nuclear genes (see Sambrook, J. F; Fritsch, E. F.; Maniatis, T.; Cold Spring Harbor Laboratory Press, Second Edition, 1989, New York), unambiguously determined the amino acid sequence of the encoded mannanase protein.

Example 5

Transformation of *S. cerevisiae* by Lithium Acetate

Frozen stocks (cryostocks) were first generated as follows: A 15 ml preculture of BY4741 was generated in YPD in a 50 ml Erlenmeyer flask incubated at 30° C. and 150 rpm overnight. 10 ml of this culture were used to inoculate 100 ml pre-warmed YPD in a 500 ml Erlenmeyer flask incubated at 30° C. and 150 rpm until an optical density at 600 nm of 6-8 was reached. This culture was mixed with an equal volume of 30% glycerol and stored in 1.6 ml aliquots at −80° C.

Generation of competent cells: 50 ml YPD was inoculated to an initial optical density at 600 nm of 0.5 using cryostocks (above), or using a fresh overnight YPD preculture (above). The 50 ml culture was incubated at 30° C. at 150 rpm 2-4 h until an optical density at 600 nm of 1.0 was reached. The culture was then centrifuged at 1500×g at 20-25° C. for 5 min. The supernatant was discarded and the pellet was resuspended in 20 ml sterile water and centrifuged 5 min at 2500× g. The supernatant was discarded and the pellet resuspended in 1 ml water and transferred to a 2 ml centrifuge tube and re-centrifuged at 10000 to 15000×g for 10 s. The supernatant was discarded and the pellet resuspended and brought to 500 µl with 100 mM lithium acetate (about 2×10$^9$ cells/ml) and incubated 15 min at 30° C.

Transformation of competent cells: Carrier DNA was prepared by boiling 2.63 mg salmon sperm DNA per ml TE buffer (10 mM Tris HCl, 1 mM EDTA, pH 8.0) and stored at −20° C. The plasmid to be transformed (1 μg) was mixed with 38 μl carrier DNA in a 2 ml centrifuge tube and chilled on ice. 50 μl of vortexed competent cells were then mixed with the DNA and 300 μl PEG/LiAc (500 μl of 1 M lithium acetate; 500 μl of water and 4 ml 50% PEG 3350) added and mixed. The mixture was incubated at 30° C. for 30 min, then 42° C. for 20 min and centrifuged at 10000-15000×g for 10 s. The cell pellet was resuspended in 1 ml of YPD and incubated 2 h at 30° C. and 150 rpm, before plating to solid SC-glucose.

Example 6

Retransformation and Expression of Specific Mannanase Genes in Saccharomyces cerevisiae After confirmation of the correct DNA sequence, the isolated DNA was transformed into the Saccharomyces host strain, BY4741, by the lithium acetate method (see example 5). Transformed cultures were plated to SC-glucose solid medium and incubated at 30° C. Individual colonies were isolated on this solid medium. A resulting isolated colony was inoculated into a 15 ml test tube containing 2 ml SC-glucose which was agitated in a rotary shaker at 150 rpm and 30° C. overnight. From this culture, a 500 ml Erlenmeyer flask containing 100 ml of SC-glucose liquid medium was inoculated to 0.005 OD at 600 nm. The flask was agitated in a rotary shaker at 150 rpm and 30° C. overnight until the optical density at 600 nm was above 2. The culture was subjected to centrifugation and the cell pellet discarded. The desired improved mannanase was then tested or used directly as a culture supernatant and/or was optionally purified from the supernatant liquid and tested or used as a purified preparation. This process was found scalable to larger volumes. The third codon of the mature protein was reverted from an arginine to the original serine codon and was found to have no noticeable effect on protein phenotypic properties.

Example 7

Expression and Purification of Mannanase

S. cerevisiae clones harbouring the gene for β-mannanase are stored as cryo-cultures at −80 C.°, well known to anyone skilled in the art. A preculture in 100 ml of medium A (16.8 g/l yeast nitrogen base; 2 g/l CSM-URA; 4% galactose; 1% Casein hydrolysate) supplemented with 2% glucose and 20 μg/ml rifampicin were inoculated from a cryo stock and grown for 48 h at 30° C. in a 1 l flask. This culture served to inoculate a 1 l expression culture at a density of 100 mOD in expression medium (medium A+10 μg/ml rifampicin) in a 5 l flask. The culture was grown for 72 h at 30° C. Cells were removed by centrifugation and the supernatant subjected to a 40-fold concentration by ultrafiltration using a 5 kDa cut-off membrane (Vivaflow 200 module). The concentrate was subsequently diafiltrated with the same cut-off to effect a buffer exchange (50 mM $NaH_2PO_4$, 300 mM NaCl, pH 5.0) and concentrated to a final volume of 1/40 of the culture volume.

The concentrate was filtered through a 0.45 μm filter and the pH adjusted to 8.0 just before loading onto a metal affinity column (BD-Talon, BD-Bioscience; bed-volume 25 ml equilibrated with diafiltration buffer). The column was washed with several bed-volumes of diafiltration buffer pH 8.0 followed by three bed-volumes of 2% buffer B (buffer B: 50 mM $NaH_2PO_4$, 300 mM NaCl, 250 mM imidazole, pH 8.0). Mannanase was eluted with a gradient from 2% to 100% buffer B over five column volumes. Fractions were checked for activity with the AZCL-assay and pooled accordingly.

Example 8

Comparison of Trichoderma reesei Mannanase and the Variant S3R

The temperature stability and mannose production of Trichoderma reesei mannanase as shown in SEQ ID NO:1 was compared with the mannanase variant derived from SEQ ID NO:1 by introducing the substitution S3R (serine to alanine at position 3). In a first experiment, the substrate was palm kernel expeller sieved to obtain a grains of <45 μm which was suspended in buffer (100 mM sodium acetate pH 5.0, 0.1% TritonX100) at a concentration of 4% (w/v). Supernatant from Saccharomyces cerevisiae cultures expressing the mannanase enzymes was mixed 1 to 1 with substrate suspension and incubated at different temperatures for 24 h. Mannose concentrations were determined with a commercial kit (Megazyme) according to the instructions of the supplier. As seen in FIG. 1A, the mannose production of the two mannanases was identical within the error of the experiment. Similarly, in a second experiment the thermal stability of the mannanase enzymes was compared in a setup described in example 9, using galactomannan carob as a substrate. Results shown in FIG. 1B support the finding that the Trichoderma reesei wild-type mannanase according to SEQ ID NO:1 and the variant S3R have the same thermal stability.

Example 9

Enhanced Activity at Higher Reaction Temperatures on Galactomannan Substrate

Mannanases may be used to depolymerise poly-mannan carbohydrates present in a variety of plant or microbial material. These processes are preferably run at elevated temperatures providing thermostable enzymes with a selective advantage. The mannanase variants of the current invention are more thermostable than the Trichoderma reesei wild-type mannanase (including the S3R variant enzyme) as demonstrated in this example. Yeast clones expressing different mannanase variants were grown in a preculture in medium A (16.8 g/l yeast nitrogen base; 2 g/l CSM-URA; 4% galactose; 1% Casein hydrolysate) supplemented with 2% glucose and 20 μg/ml rifampicin. This culture served to inoculate an 250 μl expression culture in 96-deep-well plates at a density of 100 mOD in expression medium (medium A+10 μg/ml rifampicin) and were grown for 72 h at 30° C. Cells were removed by centrifugation. A stock solution of galactomannan substrate (galactomannan carob, low viscosity; Megazyme) was generated by suspending galactomannan at 10 g/l in 50 mM sodium acetate pH 5.0 buffer, autoclaving and filtering the solution through a 0.8 μm filter. 15 μl of yeast culture supernatant were mixed with 81 μl of 1% Galactomannan (1/10 dilution of stock solution in 100 mM sodium acetate pH 5.0) and incubated at various temperatures for 16 h.

The mannose content of the sample was determined using a commercial test kit from Megazyme according to the manufacturer's instructions. The assay is based on several coupled enzymatic reactions ultimately leading to the formation of fluorescent resorufin. Two volumes of sample (diluted 1/15 in 50 mM sodium acetate pH 5.0) were mixed with one volume of assay containing all reaction components. Fluorescence intensity was determined after 60 min incubation at 37° C. and mannose content of the samples calculated from a mannose calibration curve.

Example 10

Enhanced Mannose Production at Elevated Temperatures on Palm-Kernel Extract Substrate One of the preferred applications involves the depolymerisation of galactomannan in palm kernels for use as feed supplement. The substrate palm-kernel expeller (PKE) consists of ground palm kernels with a particle size distribution between roughly 10 μm and 1 mm. Optionally, the substrate may be sieved to obtain a more uniform particle size of, e.g. 45 μm.

400 mg of dry substrate is placed in a 1.5 ml plastic tube and 600 μl of a mannanase solution (100 μg/ml) is added. The slurry is mixed vigorously on a vortexer and placed in a thermoblock preheated to the desired temperature, e.g. 63° C., 67° C. or 70° C. Samples are taken at the indicated time points, centrifuged (30 min; 20,000 g; 4° C.) and ca. 130 μl of the fluidic phase taken and stored at −20° C. for further analysis.

The mannose content of the sample is determined using a commercial test kit from Megazyme according to the manufacturer's instructions. The assay is based on several coupled enzymatic reactions ultimately leading to the formation of fluorescent resorufin. Two volumes of sample are mixed with one volume of assay containing all reaction components. Fluorescence intensity is determined after 60 min incubation at 37° C. and mannose content of the samples calculated from a mannose calibration curve.

For HPLC determination of mannose and other sugar components the refractive index of the sample is determined and the sugar content calculated from a glucose calibration curve. Samples are diluted to 3% total sugar content with distilled water, centrifuged for 30 min at 20,000 g at 4° C. and subjected to HPLC-analysis using two aminex HPX-87C columns (300×7.8 mm) in series heated to 85° C. with a Carbo-C-Refill Cartridges as precolumn (Biorad) and water as solvent. The flow-rate was set to 0.6 ml/min and detection via refraction index change on a RID-10A (Shimadzu). Specific sugars are identified using authentic samples as standards.

Example 11

Residual Mannanase Activity after PKE Incubation

Residual mannanase activity was analysed with mannanase enzymes (as isolated in example 7) after incubation of PKE with different mannanase variants at several temperatures and times points. As substrate for activity determination AZCL-galactomannan-carob (Megazyme) was used. 100 mg of AZCL-galactomannan were suspended in 30 ml buffer A (50 mM NaAc pH 5.0; 10% Glycerine; 0.1% TritonX100), homogenised in a Dounce-homogeniser and diluted 1:3 in buffer A.

In a 96-deep-well microtiter plate 650 μl of substrate suspension were mixed with 50 μl sample or enzyme standard. After incubation for 30 min at 55° C. the plates were centrifuged at 4000 rpm for 1 min and supernatant transferred to a clear 96-well plate. Absorption was determined at 590 nm in a standard plate reader (Ultra, Tecan). By comparing samples before and after heat incubation residual activity was calculated.

Example 12

Mannose Production as Function of Enzyme Concentration

Enhanced thermostability allows a particular process to run at a lower enzyme concentration compared to a less thermostable enzyme as demonstrated in this example. The wild-type mannanase was used at 100 μg/ml while the thermostable mannanase variant was used at 100, 80, 60, 40 and 20 μg/ml, respectively, on PKE as a substrate. Temperatures were 63° C. and 67° C. Mannose concentration was determined as described using the commercial kit from Megazyme.

Example 13

Thermostability of Mannanase Variants in Buffer

The thermostability of mannanase variants of the invention was further tested by incubating samples at various temperatures prior to determination of residual activity. Four volumes of supernatant from yeast cultures expressing the mannanase variants was mixed with one volume of buffer (500 mM sodium acetate, pH 5.0) and incubated at temperatures ranging from 58° C. to 82° C. The activity was determined using AZCL-galactomannan as a substrate as described in example 11. Comparison of the activity against a sample kept at 25° C. allowed calculation of the residual activity after thermal incubation.

Example 14

Pepsin and pH-Stability

In one preferred embodiment of the invention, the variant mannanases are used as a feed supplement. Mannanase activity on polymannan-containing substrates included in the standard feed composition would release beneficial oligo-mannans and mannose with positive health effects for the animals. For this application mannanase variants would have to sustain the harsh conditions in the stomach, e.g. the low pH and proteases, respectively. The resistance to low pH conditions has been tested for different variants. Four volumes of a mannanase solution (50 μg/ml in 50 mM sodium acetate, pH 5.0) were mixed with 1 volume of 1 M glycine/HCl buffer pH 2.0 (final pH 2.3) and incubated at 37° C. At different time points aliquots were taken and the pH adjusted to 6.1 by adding 5 volumes of buffer A (100 mM NaCl, 200 mM sodium phosphate, pH 6.5).

Residual activity was measured by mixing one volume of sample with 13 volumes of 0.1% suspension of AZCL-galactomannan in 50 mM NaAc pH 5.0 and incubation at 50° C. for 20 min. After centrifugation the solubilized AZCL-galactomannan was measured as absorbance at 590 nm. Enzyme activity was quantitated by comparing to a standard with known enzyme concentrations and residual activity calculated by normalization to samples kept at pH 5.0.

Resistance to pepsin was measured as above but with pepsin included in the 1 M glycine/HCl buffer at a concentration of 5 mg/ml, yielding a final concentration of 1 mg/ml.

Example 15

Improved Activity at Low pH

As described in detail above, activity at low pH confers an advantage to mannanase enzymes in the application as a feed additive since polyose substrates are already metabolized under acidic conditions as present e.g. in the stomach of swine and in the crop and stomach of poultry. The activity profile of several variants has been tested at relevant pH-conditions, i.e. pH values below 6. Protein preparations of variant B and C were adjusted to different pH values by dilution in appropriate buffer systems (pH 2-3.5: 500 mM glycine buffer, pH 4-5.5: 250 mM sodium acetate buffer, detailed protocols for preparation of these buffers are known to the person skilled in the art) and incubated for 4 h at 37° C. with 40% dry substance of palm kerner expeller substrate containing polymannose substrate (see above). After completion of the reaction mannose concentration was determined by using a commercial mannose quantification kit from Megazyme according to the manufactures instructions. The assay is based on several coupled enzymatic reactions ultimately leading to the formation of fluorescent resorufin. Two volumes of sample are mixed with one volume of assay containing all reaction components. Fluorescence intensity is determined after 60 min incubation at 37° C., and mannose content of the samples is calculated from a mannose calibration curve. Data were corrected for small alterations of pH values in preparation of the protein solutions and background activity was measured by performing the testing described above with protein samples inactivated at 90° C. for 15 min to account for additional effects of buffer substances on the reaction. Background values are subtracted from the experimental results in the data given in FIG. 8. Variants B and C show high activity a low pH conditions conferring superior properties to the variants for application in feed for production of mannose from polymannose containing feedstocks in the upper gastrointestinal tract of animals.

Example 16

Pepsin/pH Stability 4 volumes of a mannanase solution were mixed with 1 volume of 1 M glycine/HCl buffer pH 2.5 with 1.25 mg/ml Pepsin and incubated at 37° C. for 1 h. The pH value of the incubation mixture is 2.65. Then 21 volumes of 0.86% galactomannan-solution in 190 mM sodium acetate buffer pH 5.5 were added and the reaction was incubated at 37° C. for 16 h. 2 volumes of the reaction mixture were mixed with 1 volume of mannose detection assay (as described) at 37° C. for 30 min. The fluorescence units were determined with excitation at 535 nm and emission at 595 nm using a fluorescence reader. The relative residual activities in % are determined in comparison to activity after incubation at pH 5.0. (see Table 5).

TABLE 5

Low pH/proteolytic stability, residual activity values determined at pH 2.65 in the presence/absence of 0.25 mg/ml Pepsin:

| variant | mutations | Residual activity | |
| --- | --- | --- | --- |
| | | pH2.65 w/o Pepsin | pH 2.65 + 0.25 mg/ml Pepsin |
| WT | — | 25 | 10 |
| variant B | L207F, F274L | 70 | 23 |
| variant C | T201S, Q280R, F274L | 90 | 84 |
| variant 31 | T201S, L207F, F274L | 100 | 87.6 |
| variant 16 | T201S | 98 | 96 |
| variant 8 | T201G | 57 | 27 |
| variant 9 | T201A | 69 | 44 |
| variant 18 | Q11H, P170L | 38 | 20 |

TABLE 5-continued

Low pH/proteolytic stability, residual activity values determined at pH 2.65 in the presence/absense of 0.25 mg/ml Pepsin:

| variant | mutations | Residual activity | |
| --- | --- | --- | --- |
| | | pH2.65 w/o Pepsin | pH 2.65 + 0.25 mg/ml Pepsin |
| variant 42 | N173H, V181T, T201S, L207W, F274L | 100 | 81 |

For low pH/proteolytic stability especially position T201 seems to be quite important. Other important positions are Q280 and L207. This means that all variants carrying a substitution in any of these residues represent particularly preferred embodiments of the present invention.

In this context, it is noteworthy that the variants shown in Table 5, besides featuring improved low pH/proteolytic stability, do all have improved temperature stability as well, as they are all mentioned in Table 3A. This means that the said variants are particularly preferred embodiments of the present invention.

Some of the said variants, i.e. variant B (amino acid sequence represented as SEQ ID NO 10) and variant C (amino acid sequence represented as SEQ ID NO 11), variant 16, variant 31 and variant 42 are even more preferred embodiments due to the highly improved properties, both in terms of temperature stability as well as in terms of low pH/proteolytic stability.

Example 17

Release of Mannose/Mannooligosaccharides from Coffee Grounds

Coffee ground was suspended 40% (w/v) in water or washed 10 times with water before suspending in water. The suspensions were incubated with 200 μg/ml mannanase variant B for 16 h at 50° C., 600 rpm. After treatment the samples were centrifuged and mannose content of the supernatants was determined in comparison to untreated samples with mannose assay as described above (see Table 6).

TABLE 6

Mannose yields of washed and unwashed coffee waste in comparison to untreated coffee waste

| Samples | Mannose (mg/ml) |
| --- | --- |
| coffee waste sample treated with variant B | 38.1 |
| unwashed coffee waste sample treated with variant B | 24.6 |

Example 18

Extraction of Oil from PKE

Dried PKE was suspended 33% (w/v) in 250 mM NaAc buffer pH 5.0. To this suspension either 100 μg/ml of variant B or C or no enzyme was added. Incubation was for 16 h at 50° C. Then the treated PKE was dried and the weight determined. Palm kernel oil was extracted in a soxhlet apparatus with n-hexane for 24 h. The solvent was removed and the oil content was determined by weighing (see Table 7).

TABLE 7

Oil yield of treated and untreated PKE

| sample | % oil (per g dry mass) |
|---|---|
| Untreated | 4.05 |
| Variant B treated | 4.36 |
| Variant C treated | 4.19 |

Example 19

Growth of Yeast in Broth with Supernatant of Mannanase Treated PKE

33% (w/v) PKE suspension in 250 mM NaAc buffer pH 5.0 was incubated +/−200 μg/ml variant B for 16 h at 50° C. After centrifugation 1 volume of the supernatants were added to yeast basis medium (4 vol Yb (4×), 4 vol CSM-U (4×), 1 vol Casein hydrolysate). The media were inoculated with S. cerevisiae and incubated for 72 h at 30° C. 160 rpm. The OD 600 nm was determined (see Table 8).

TABLE 8 yeast growth on untreated and treated PKE substrate

| sample | OD 600 nm |
|---|---|
| Without enzymatic treatment | 4.45 |
| With mannanase treatment | 5.6 |

The same experiment was repeated with washed PKE (10× vol water, PKE wash) and with PKE incubated for 16 h in 250 mM NaAc pH 5 and subsequent washing with water (PKE pretreated) before the enzymatic treatment (see Table 9).

TABLE 9

Yeast growth on an untreated and treated PKE substrate

| sample | OD 600 nm |
|---|---|
| PKE wash without mannanase | 3.4 |
| PKE wash with manna | 4.5 |
| PKE pretreated without mannanase | 3.6 |
| PKE pretreated with mannanase | 5.0 |

The results show that mannanase treatment of PKE releases sugars that can be utilised for the fermentative production of ethanol by S. cerevisiae.

Example 20

Release of Mannose from Guar Gum, Locust Bean Gum and Konjac Glucomannan

1% (w/v) suspensions of guar gum, locust bean gum and konjac glucomannan in water were incubated with 200 μg/ml variant B at 50° C. and 400 rpm for 16 h. After centrifugation the content of mannose in the supernatant was detected as described above (see FIG. 9).

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

SEQUENCE LISTING, FREE TEXT

SEQ ID NO 1: wild-type *Trichoderma reesei* mannanase/amino-acid
SEQ ID NO 2: wild-type *Trichoderma reesei* mannanase/DNA
SEQ ID NO 3: primer Mann5A forward fishing
SEQ ID NO 4: primer Mann5A reverse fishing
SEQ ID NO 5: wild type leader DNA
SEQ ID NO 6: improved leader DNA
SEQ ID NO 7: improved leader prot seq2
SEQ ID NO 8: forward primer for cloning intron-free PIN with leader into pYES2
SEQ ID NO 9: reverse primer for cloning intron-free PIN with leader into pYES2
SEQ ID NO 10: variant B mannanase
SEQ ID NO 11: variant C mannanase
SEQ ID NO 12: variant 31 mannanase
SEQ ID NO 13: variant 16 mannanase

---

The invention claimed is:

1. A modified β-mannanase having an amino acid sequence that is at least 90% homologous to SEQ ID NO:1, wherein said modified β-mannanase includes a modification by insertion, deletion and/or substitution of the amino acid residue corresponding to position 274 of SEQ ID NO:1.

2. The modified β-mannanase according to claim 1, wherein said modified β-mannanase further includes an amino acid substitution at one or more of the positions corresponding to SEQ ID NO:1 selected from the group consisting of 4, 7, 11, 13, 31, 41, 66, 70, 74, 97, 101, 113, 132, 146, 148, 170, 173, 181, 182, 185, 186, 187, 189, 201, 207, 215, 216, 220, 252, 255, 259, 280, 281, 282, 313, 316, 317, 325, 331, 341, 345, 351 and 352.

3. The modified β-mannanase according to claim 1, wherein the total number of amino acid insertions, deletions and substitutions corresponding to SEQ ID NO:1 is from 1 to 30.

4. The modified -mannanase according to claim 1, wherein said modified β-mannanase includes one or more amino acid substitutions corresponding to SEQ ID NO:1 as shown in the Table below:

| | |
|---|---|
| variant A | F274L |
| variant B | L207F; F274L |
| variant C | T201S; Q280R; F274L |
| variant F | A215T; F274L; N282D |
| variant G | Y220F; F274L |
| variant H | V187M; F274L |
| variant K | V181A; F274L |
| variant L | V148I; F274L |
| variant M | N173H; F274L; N331S; |
| variant 13 | F274M |
| variant 21 | N13D; F274L |
| variant 22 | F274L; Q280L |
| variant 23 | F274L; Q317H |
| variant 25 | L207F; F274M |
| variant 28 | F4Y; I70V; F274L |
| variant 29 | Q101R; F274L; Q281H |
| variant 30 | T201G; L207F; F274L |
| variant 31 | T201S; L207F; F274L |
| variant 32 | V181T; L207W; A215T; F274L |
| variant 34 | K74M; F274L; A313T; V325I |
| variant 35 | N173H; V181H; L207W; F274L |
| variant 36 | T201S; L207Y; F274L; Q280R |
| variant 37 | T201S; L207W; F274L; Q280R |
| variant 38 | T201S; L207R; F274L; Q280R |
| variant 39 | V181T; L207W; F274M; N331S; P352L |
| variant 40 | N173H; L207W; A215T; F274L; Q280R |
| variant 41 | V181H; L207W; A215T; F274L; N282D |
| variant 42 | N173H; V181T; T201S; L207W; F274L |
| variant 43 | N173H; V181H; L207W; A215T; F274L |
| variant 44 | V181H; L207W; A215T; F274L; Q280R; N282D |
| variant 45 | S66P; N173H; V181H; A215T; F274L; Q280S; N282D |
| variant 46 | N173H; V181T; L207W; A215T; F274L; Q280R; N282D. |

5. The modified β-mannanase according to claim 1, wherein said amino acid residue corresponding to position 274 of SEQ ID NO:1 is A, C, G, H, I, L, M, V, W or Y.

6. The modified β-mannanase according to claim 1, wherein said amino acid residue corresponding to position 274 of SEQ ID NO:1 is L.

7. The modified β-mannanase according to claim 1, wherein said amino acid corresponding to position 274 of SEQ ID NO:1 is selected from the group consisting of F274L and F274M, and wherein the modified β-mannanase further comprises one or more substitutions corresponding to SEQ ID NO:1 selected from the group consisting of F4Y, I7V, Q11R, Q11H, N13D, F31Y, T41I, S66P, I70V, K74M, Q97R, Q101R, N113Y, T132S, K146Q, V148I, P170L, N173H, N173T, V181A, V181H, V181T, Q182R, T185K, S186N, V187M, V187L, Q189H, T201S, T201A, T201G, L207F, L207W, L207R, L207S, L207Y, A215T, Y216H, Y220F, T252I, N255I, Q259R, Q280R, Q280S, Q280L, Q281H, N282D, A313T, A316T, Q317H, V325I, D341E, G345C, P351L, P352L and N331S.

8. The modified β-mannanase according to claim 4, wherein said modified β-mannanase has increased thermostability as compared to SEQ ID NO:1.

9. The modified β-mannanase according to claim 1, wherein said modified β-mannanase includes one or more substitutions corresponding to SEQ ID NO:1 as shown in the Table below:

| | |
|---|---|
| variant B | L207F, F274L |
| variant C | T201S, Q280R, F274L |
| variant 31 | T201S, L207F, F274L |
| variant 42 | N173H, V181T, T201S, L207W, F274L | and wherein the said mannanase has increased stability at acidic pH values and/or resistance to protease degradation as compared to SEQ ID NO:1.

10. A composition comprising the modified β-mannanase according to claim 1.

11. The modified β-mannanase according to claim 1, wherein the total number of insertions, deletions and substitutions corresponding to SEQ ID NO:1 is from 1 to 10.

12. The modified β-mannanase according to claim 1, wherein the total number of insertions, deletions and substitutions corresponding to SEQ ID NO:1 is from 1 to 5.

13. The modified β-mannanase according to claim 1 further comprising one or more amino acid substitutions at a position corresponding to SEQ ID NO:1 as shown in the Table below:

| Wild type residue | Substituted by |
|---|---|
| F4 | A, C, D, E, G, H, I, K, L, M, N, P, Q, R, S, T, V, W or Y |
| I7 | A, C, D, E, F, G, H, K, L, M, N, P, Q, R, S, T, V, W or Y |
| Q11 | A, C, D, E, F, G, H, I, K, L, M, N, P, R, S, T, V, W or Y |
| N13 | A, C, D, E, F, G, H, I, K, L, M, P, Q, R, S, T, V, W or Y |
| F31 | A, C, D, E, G, H, I, K, L, M, N, P, Q, R, S, T, V, W or Y |
| T41 | A, C, D, E, F, G, H, I, K, L, M, N, P, Q, R, S, V, W or Y |
| S66 | A, C, D, E, F, G, H, I, K, L, M, N, P, Q, R, T, V, W or Y |
| I70 | A, C, D, E, F, G, H, K, L, M, N, P, Q, R, S, T, V, W or Y |
| K74 | A, C, D, E, F, G, H, I, L, M, N, P, Q, R, S, T, V, W or Y |
| Q97 | A, C, D, E, F, G, H, I, K, L, M, N, P, R, S, T, V, W or Y |
| Q101 | A, C, D, E, F, G, H, I, K, L, M, N, P, R, S, T, V, W or Y |
| N113 | A, C, D, E, F, G, H, I, K, L, M, P, Q, R, S, T, V, W or Y |
| T132 | A, C, D, E, F, G, H, I, K, L, M, N, P, Q, R, S, V, W or Y |
| K146 | A, C, D, E, F, G, H, I, L, M, N, P, Q, R, S, T, V, W or Y |
| V148 | A, C, D, E, F, G, H, I, K, L, M, N, P, Q, R, S, T, W or Y |
| P170 | A, C, D, E, F, G, H, I, K, L, M, N, Q, R, S, T, V, W or Y |
| N173 | A, C, D, E, F, G, H, I, K, L, M, P, Q, R, S, T, V, W or Y |
| V181 | A, C, D, E, F, G, H, I, K, L, M, N, P, Q, R, S, T, W or Y |
| Q182 | A, C, D, E, F, G, H, I, K, L, M, N, P, R, S, T, V, W or Y |
| T185 | A, C, D, E, F, G, H, I, K, L, M, N, P, Q, R, S, V, W or Y |
| S186 | A, C, D, E, F, G, H, I, K, L, M, N, P, Q, R, T, V, W or Y |
| V187 | A, C, D, E, F, G, H, I, K, L, M, N, P, Q, R, S, T, W or Y |
| Q189 | A, C, D, E, F, G, H, I, K, L, M, N, P, R, S, T, V, W or Y |
| T201 | A, C, D, E, F, G, H, I, K, L, M, N, P, Q, R, S, V, W or Y |
| L207 | A, C, D, E, F, G, H, I, K, M, N, P, Q, R, S, T, V, W or Y |
| A215 | C, D, E, F, G, H, I, K, L, M, N, P, Q, R, S, T, V, W or Y |
| Y216 | A, C, D, E, F, G, H, I, K, L, M, N, P, Q, R, S, T, V or |
| Y220 | A, C, D, E, F, G, H, I, K, L, M, N, P, Q, R, S, T, V or W |

-continued

| Wild type residue | Substituted by |
|---|---|
| T252 | A, C, D, E, F, G, H, I, K, L, M, N, P, Q, R, S, V, W or Y |
| N255 | A, C, D, E, F, G, H, I, K, L, M, P, Q, R, S, T, V, W or Y |
| Q259 | A, C, D, E, F, G, H, I, K, L, M, N, P, R, S, T, V, W or Y |
| Q280 | A, C, D, E, F, G, H, I, K, L, M, N, P, R, S, T, V, W or Y |
| Q281 | A, C, D, E, F, G, H, I, K, L, M, N, P, R, S, T, V, W or Y |
| N282 | A, C, D, E, F, G, H, I, K, L, M, P, Q, R, S, T, V, W or Y |
| A313 | C, D, E, F, G, H, I, K, L, M, N, P, Q, R, S, T, V, W or Y |
| A316 | C, D, E, F, G, H, I, K, L, M, N, P, Q, R, S, T, V, W or Y |
| Q317 | A, C, D, E, F, G, H, I, K, L, M, N, P, R, S, T, V, W or Y |
| V325 | A, C, D, E, F, G, H, I, K, L, M, N, P, Q, R, S, T, W or Y |
| N331 | A, C, D, E, F, G, H, I, K, L, M, P, Q, R, S, T, V, W or Y |
| D341 | A, C, E, F, G, H, I, K, L, M, N, P, Q, R, S, T, V, W or Y |
| G345 | A, C, D, E, F, H, I, K, L, M, N, P, Q, R, S, T, V, W or Y |
| P351 | A, C, D, E, F, G, H, I, K, L, M, N, Q, R, S, T, V, W or Y |
| P352 | A, C, D, E, F, G, H, I, K, L, M, N, Q, R, S, T, V, W or Y. |

14. The modified β-mannanase according to claim 1, further comprising one or more amino acid substitutions corresponding to a residue in SEQ ID NO:1 selected from the group consisting of:
(i) the amino acid N173 is substituted by A, C, D, G, H, S, P, Q, T or V;
(ii) the amino acid V181 is substituted by A, C, F, G, H, I, L, M, W or Y;
(iii) the amino acid V148 is substituted by A, C, F, G, H, I, L, M, W or Y;
(iv) the amino acid V187 is substituted by A, C, F, G, H, I, L, M, W or Y;
(v) the amino acid T201 is substituted by A, C, H, N, P, Q, S, V or Y;
(vi) the amino acid L207 is substituted by A, C, F, G, H, I, M, V, W or Y;
(vii) the amino acid A215 is substituted by C, F, G, H, I, L, M, T, V, W or Y;
(viii) the amino acid Y220 is substituted by A, F, H, I, L, M, N, P, V, or W;
(ix) the amino acid Q280 is substituted by C, D, E, H, K, N, R, S, T or Y;
(x) the amino acid N282 is substituted by C, D, E, H, K, Q, R, S, T or Y; and
(xi) the amino acid N331 is substituted by C, D, E, H, K, Q, R, S, T or Y.

15. The modified β-mannanase according to claim 1, further comprising one or more amino acid substitutions corresponding to a residue in SEQ ID NO:1 selected from the group consisting of:
(i) the amino acid N173 is substituted by A, C, H, S, T or V;
(ii) the amino acid V181 is substituted by A, I, L or M;
(iii) the amino acid V148 is substituted by A, I, or L;
(iv) the amino acid V187 is substituted by A, I, L or M;
(v) the amino acid T201 is substituted by A, C, N, Q, S or V;

(vi) the amino acid L207 is substituted by A, F, G, H, I or V;
(vii) the amino acid A215 is substituted by C, F, G, H, I, L or T;
(viii) the amino acid Y220 is substituted by F, H, W or Y;
(ix) the amino acid Q280 is substituted by C, H, N, S, or T;
(x) the amino acid N282 is substituted by C, D, H, Q, S or T; and
(xi) the amino acid N331 is substituted by C, H, Q, S or T.

16. The modified β-mannanase according to claim 1, further comprising one or more amino acid substitutions corresponding to a residue in SEQ ID NO:1 selected from the group consisting of:
(i) the amino acid N173 is substituted by H;
(ii) the amino acid V181 is substituted by A;
(iii) the amino acid V148 is substituted by I;
(iv) the amino acid V187 is substituted by M;
(v) the amino acid T201 is substituted by S;
(vi) the amino acid L207 is substituted by F;
(vii) the amino acid A215 is substituted by T;
(viii) the amino acid Y220 is substituted by F;
(ix) the amino acid Q280 is substituted by R;
(x) the amino acid N282 is substituted by D; and
(xi) the amino acid N331 is substituted by S.

17. The modified β-mannanase according to claim 1, wherein the modified mannanase comprises one or more of the combinations of substitutions corresponding to residues in SEQ ID NO:1 selected from the group consisting of F274L/A215T, F274L/N282D, F274L/A215T/N282D, F274L/Y220F, F274L/V187M, F274L/V181A, F274L/V148I, F274L/N173H, F274L/N331S, F274L/N173H/N331S, F274L/L207F, F274L/T201S, F274L/Q280R, N13D/F274L, F274L/Q280L, F274L/Q317H, L207F/F274M, F4Y/I70V/F274L, Q101R/F274L/Q281H, T201G/L207F/F274L, T201S/L207F/F274L, V181T/L207W/A215T/F274L, K74M/F274L/A313T/V325I, N173H/V181H/L207W/F274L, T201S/L207Y/F274L/Q280R, T201S/L207W/F274L/Q280R, T201S/L207R/F274L/Q280R, V181T/L207W/F274M/N331S/P352L, N173H/L207W/A215T/F274L/Q280R, V181H/L207W/A215T/F274L/N282D, N173H/V181T/T201S/L207W/F274L, N173H/V181H/L207W/A215T/F274L, V181H/L207W/A215T/F274L/Q280R/N282D, S66P/N173H/V181H/A215T/F274L/Q280S/N282D, N173H/V181T/L207W/A215T/F274L/Q280R/N282D and F274L/T201S/Q280R.

18. The modified β-mannanase according to claim 1, wherein the modified mannanase has the sequence shown in SEQ ID NOs: 10 (variant B), 11 (variant C) or 12 (variant 31).

19. The modified β-mannanase of claim 1, wherein said modified β-mannanase includes one or more amino acid substitutions corresponding to amino acid residue in SEQ ID NO:1 selected from the group consisting of:
(i) the amino acid N173 is substituted by A, C, D, E, F, G, H, I, K, L, M, P, Q, R, S, T, V, W or Y;
(ii) the amino acid V181 is substituted by A, C, D, E, F, G, H, I, K, L, M, N, P, Q, R, S, T, W or Y;
(iii) the amino acid V148 is substituted by A, C, D, E, F, G, H, I, K, L, M, N, P, Q, R, S, T, W or Y;
(iv) the amino acid V187 is substituted by A, C, D, E, F, G, H, I, K, L, M, N, P, Q, R, S, T, W or Y;
(v) the amino acid T201 is substituted by A, C, D, E, F, G, H, I, K, L, M, N, P, Q, R, S, V, W or Y;
(vi) the amino acid L207 is substituted by A, C, D, E, F, G, H, I, K, M, N, P, Q, R, S, T, V, W or Y;
(vii) the amino acid A215 is substituted by C, D, E, F, G, H, I, K, L, M, N, P, Q, R, S, T, V, W or Y;
(viii) the amino acid Y220 is substituted by A, C, D, E, F, G, H, I, K, L, M, N, P, Q, R, S, T, V or W;

(ix) the amino acid Q280 is substituted by A, C, D, E, F, G, H, I, K, L, M, N, P, R, S, T, V, W or Y;
(x) the amino acid N282 is substituted by A, C, D, E, F, G, H, I, K, L, M, P, Q, R, S, T, V, W or Y; and
(xi) the amino acid N331 is substituted by A, C, D, E, F, G, H, I, K, L, M, P, Q, R, S, T, V, W or Y.

* * * * *